US008399692B2

(12) United States Patent
Krafft et al.

(10) Patent No.: US 8,399,692 B2
(45) Date of Patent: Mar. 19, 2013

(54) EPICHLOROHYDRIN, MANUFACTURING PROCESS AND USE

(75) Inventors: Philippe Krafft, Rhode Saint Genese (BE); Patrick Gilbeau, Braine-le-Comte (BE); Dominique Balthasart, Brussels (BE); Noel Boulos, Houston, TX (US)

(73) Assignee: Solvay (Societe Anonyme), Brussels (BE)

( * ) Notice: Subject to any disclaimer, the term of this patent is extended or adjusted under 35 U.S.C. 154(b) by 370 days.

(21) Appl. No.: 12/663,749

(22) PCT Filed: Jun. 11, 2008

(86) PCT No.: PCT/EP2008/057247
§ 371 (c)(1),
(2), (4) Date: Dec. 9, 2009

(87) PCT Pub. No.: WO2008/152045
PCT Pub. Date: Dec. 18, 2008

(65) Prior Publication Data
US 2010/0168379 A1  Jul. 1, 2010

Related U.S. Application Data

(60) Provisional application No. 61/013,672, filed on Dec. 14, 2007, provisional application No. 61/007,661, filed on Dec. 14, 2007.

(30) Foreign Application Priority Data

Jun. 12, 2007 (FR) ..................................... 07 55696
Sep. 21, 2007 (FR) ..................................... 07 57751

(51) Int. Cl.
*C07D 301/12* (2006.01)
(52) U.S. Cl. ......... 549/518; 549/516; 549/524; 549/525
(58) Field of Classification Search .................. 549/518, 549/516, 524, 525
See application file for complete search history.

(56) References Cited

U.S. PATENT DOCUMENTS

| | | |
|---|---|---|
| 280,893 A | 7/1883 | Baujard |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Herman |
| 2,811,227 A | 10/1957 | O'Connor |
| 2,829,124 A | 4/1958 | Napravnik et at |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,879,180 A | 4/1975 | Hutgens et al. |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,294,776 A | 10/1981 | Hardy et al. |
| 4,309,394 A | 1/1982 | Hudson |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,560,812 A | 12/1985 | Blytas |
| 4,595,469 A | 6/1986 | Foller |
| 4,599,178 A | 7/1986 | Blytas |
| 4,609,751 A | 9/1986 | Hajjar |
| 4,634,784 A | 1/1987 | Nagato et al. |
| 4,655,879 A | 4/1987 | Brockmann et al. |
| 4,935,220 A | 6/1990 | Schneider et al. |
| 4,960,953 A | 10/1990 | Jakobson et al. |
| 4,973,763 A | 11/1990 | Jakobson et al. |

(Continued)

FOREIGN PATENT DOCUMENTS

| | | |
|---|---|---|
| BE | 422877 | 8/1937 |
| CN | 1296003 A | 5/2001 |

(Continued)

OTHER PUBLICATIONS

RD 436093, RD, Aug. 10, 2000, Akzo Nobel.

(Continued)

*Primary Examiner* — Gregory Listvoyb
(74) *Attorney, Agent, or Firm* — Oblon, Spivak, McClelland, Maier & Neustadt, L.L.P.

(57) ABSTRACT

Product containing epichlorohydrin, wherein the amount of trichloropropane is of less than 0.01 g of trichloropropane per kg of product, a process for manufacturing the product and its use in various applications.

12 Claims, 9 Drawing Sheets

U.S. PATENT DOCUMENTS

| | | | |
|---|---|---|---|
| 4,990,695 | A | 2/1991 | Buenemann et al. |
| 5,041,688 | A | 8/1991 | Jakobson et al. |
| 5,169,964 | A * | 12/1992 | Jakobson et al. ............ 549/541 |
| 5,200,163 | A | 4/1993 | Henkelmann et al. |
| 5,278,260 | A | 1/1994 | Schaffner et al. |
| 5,286,354 | A | 2/1994 | Bard et al. |
| 5,344,945 | A | 9/1994 | Grunchard |
| 5,359,094 | A | 10/1994 | Teles et al. |
| 5,393,428 | A | 2/1995 | Dilla et al. |
| 5,445,741 | A | 8/1995 | Dilla et al. |
| 5,478,472 | A | 12/1995 | Dilla et al. |
| 5,486,627 | A | 1/1996 | Quarderer et al. |
| 5,567,359 | A | 10/1996 | Cassidy et al. |
| 5,578,740 | A | 11/1996 | Au et al. |
| 5,679,839 | A | 10/1997 | Armand et al. |
| 5,710,350 | A | 1/1998 | Jeromin et al. |
| 5,731,476 | A | 3/1998 | Shawl et al. |
| 5,744,655 | A | 4/1998 | Thomas et al. |
| 5,779,915 | A | 7/1998 | Becker et al. |
| 5,908,946 | A | 6/1999 | Stern et al. |
| 5,993,974 | A | 11/1999 | Fukushima et al. |
| 6,024,839 | A | 2/2000 | Schufeldt |
| 6,103,092 | A | 8/2000 | Silva |
| 6,111,153 | A | 8/2000 | Crow et al. |
| 6,142,458 | A | 11/2000 | Howk |
| 6,177,599 | B1 | 1/2001 | Cowfer et al. |
| 6,270,682 | B1 | 8/2001 | Santen et al. |
| 6,288,248 | B1 * | 9/2001 | Strebelle et al. ............ 549/518 |
| 6,288,287 | B2 | 9/2001 | Ueoka et al. |
| 6,350,888 | B1 | 2/2002 | Strebelle et al. |
| 6,350,922 | B1 | 2/2002 | Vosejpka et al. |
| 6,521,794 | B2 | 2/2003 | Hirota |
| 6,719,957 | B2 | 4/2004 | Brady, Jr. et al. |
| 6,740,633 | B2 | 5/2004 | Norenberg et al. |
| 6,806,396 | B2 | 10/2004 | Gelblum et al. |
| 6,831,201 | B2 | 12/2004 | Katsuura et al. |
| 7,126,032 | B1 | 10/2006 | Aiken |
| 7,128,890 | B2 | 10/2006 | Ollivier |
| 865,727 | A1 | 9/2007 | Queneau |
| 7,557,253 | B2 | 7/2009 | Gilbeau |
| 7,584,629 | B2 | 9/2009 | Sohn et al. |
| 7,615,670 | B2 | 11/2009 | Gilbeau |
| 2001/0014763 | A1 | 8/2001 | Ueoka et al. |
| 2003/0209490 | A1 | 11/2003 | Camp et al. |
| 2004/0016411 | A1 | 1/2004 | Joyce et al. |
| 2004/0024244 | A1 | 2/2004 | Walsdorff et al. |
| 2004/0047781 | A1 | 3/2004 | Becenel |
| 2004/0150123 | A1 | 8/2004 | Strofer et al. |
| 2004/0179987 | A1 | 9/2004 | Oku et al. |
| 2004/0232007 | A1 | 11/2004 | Carson et al. |
| 2005/0115901 | A1 | 6/2005 | Heuser et al. |
| 2005/0261509 | A1 | 11/2005 | Delfort et al. |
| 2006/0052272 | A1 | 3/2006 | Meli et al. |
| 2006/0079433 | A1 | 4/2006 | Hecht et al. |
| 2006/0123842 | A1 | 6/2006 | Sohn et al. |
| 2007/0112224 | A1 | 5/2007 | Krafft et al. |
| 2007/0293707 | A1 | 12/2007 | Wolfert et al. |
| 2008/0053836 | A1 | 3/2008 | Bulan et al. |
| 2008/0146753 | A1 | 6/2008 | Woike et al. |
| 2008/0154050 | A1 | 6/2008 | Gilbeau |
| 2008/0161613 | A1 | 7/2008 | Krafft et al. |
| 2008/0194847 | A1 | 8/2008 | Krafft et al. |
| 2008/0194849 | A1 | 8/2008 | Krafft et al. |
| 2008/0194851 | A1 | 8/2008 | Gilbeau |
| 2008/0200642 | A1 | 8/2008 | Krafft |
| 2008/0200701 | A1 | 8/2008 | Krafft et al. |
| 2008/0207930 | A1 | 8/2008 | Gilbeau et al. |
| 2008/0214848 | A1 | 9/2008 | Krafft et al. |
| 2008/0281132 | A1 | 11/2008 | Krafft et al. |
| 2009/0022653 | A1 | 1/2009 | Strebelle et al. |
| 2009/0131631 | A1 | 5/2009 | Krafft et al. |
| 2009/0173636 | A1 | 7/2009 | Ooms et al. |
| 2009/0198041 | A1 | 8/2009 | Krafft et al. |
| 2009/0270588 | A1 | 10/2009 | Krafft et al. |
| 2009/0275726 | A1 | 11/2009 | Krafft et al. |
| 2010/0029959 | A1 | 2/2010 | Fan et al. |
| 2010/0032617 | A1 | 2/2010 | Gilbeau et al. |
| 2010/0105862 | A1 | 4/2010 | Krafft et al. |
| 2010/0105964 | A1 | 4/2010 | Krafft et al. |
| 2011/0028683 | A1 | 2/2011 | Gilbeau et al. |
| 2011/0152545 | A1 | 6/2011 | Balthasart et al. |
| 2011/0166369 | A1 | 7/2011 | Krafft et al. |
| 2011/0237773 | A1 | 9/2011 | Gilbeau |

FOREIGN PATENT DOCUMENTS

| | | |
|---|---|---|
| CN | 101041421 | 9/2007 |
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |
| DE | 3721003 C1 | 12/1988 |
| DE | 43 02 306 | 8/1994 |
| DE | 4335311 A1 | 4/1995 |
| DE | 10203914 C1 | 10/2003 |
| DE | 10254709 A1 | 6/2004 |
| EP | 0 296 341 | 12/1988 |
| EP | 0347618 A2 | 12/1989 |
| EP | 0358255 A1 | 3/1990 |
| EP | 0421379 A1 | 4/1991 |
| EP | 0 452 265 | 10/1991 |
| EP | 0518765 A1 | 12/1992 |
| EP | 0522382 A1 | 1/1993 |
| EP | 0535949 B1 | 4/1993 |
| EP | 0561441 A1 | 9/1993 |
| EP | 0563720 A1 | 10/1993 |
| EP | 0568389 A1 | 11/1993 |
| EP | 0582201 A2 | 2/1994 |
| EP | 0 618 170 | 10/1994 |
| EP | 0 916 624 | 5/1999 |
| EP | 0919551 A1 | 6/1999 |
| EP | 0 774 450 | 2/2000 |
| EP | 1059278 A2 | 12/2000 |
| EP | 1106237 A1 | 6/2001 |
| EP | 1153887 A2 | 11/2001 |
| EP | 1163946 A1 | 12/2001 |
| EP | 1231189 A1 | 8/2002 |
| EP | 1298154 A1 | 4/2003 |
| EP | 1411027 A1 | 4/2004 |
| EP | 1752435 A1 | 2/2007 |
| EP | 1752436 A1 | 2/2007 |
| EP | 1760060 A1 | 3/2007 |
| EP | 1762556 A1 | 3/2007 |
| EP | 1770081 A1 | 4/2007 |
| EP | 1772446 A1 | 4/2007 |
| EP | 1775278 A1 | 4/2007 |
| EP | 2085364 | 8/2009 |
| FR | 1 306 231 | 10/1961 |
| FR | 1 417 388 | 10/1964 |
| FR | 1476073 A | 4/1967 |
| FR | 1 577 792 | 8/1968 |
| FR | 2151107 | 4/1973 |
| FR | 2180138 | 5/1973 |
| FR | 2 217 372 | 2/1974 |
| FR | 2565229 A1 | 12/1985 |
| FR | 2752242 A1 | 2/1998 |
| FR | 2862644 A1 | 5/2005 |
| FR | 2868419 A1 | 10/2005 |
| FR | 2869612 A1 | 11/2005 |
| FR | 2869613 A1 | 11/2005 |
| FR | 2872504 A1 | 1/2006 |
| FR | 2881732 A1 | 8/2006 |
| FR | 2885903 A1 | 11/2006 |
| FR | 2 917 411 | 12/2006 |
| FR | 2 912 743 | 8/2008 |
| FR | 2913683 | 9/2008 |
| FR | 2913683 A1 | 9/2008 |
| FR | 2918058 A1 | 1/2009 |

| | | | | | | |
|---|---|---|---|---|---|---|
| FR | 2925045 A1 | 6/2009 | | PL | 162910 | 1/1994 |
| FR | 2929611 A1 | 10/2009 | | SU | 123153 | 1/1959 |
| FR | 2935699 A1 | 3/2010 | | SU | 1125226 | 11/1984 |
| FR | 2935968 A1 | 3/2010 | | SU | 1159716 | 6/1985 |
| GB | 14767 A | 0/1914 | | SU | 1685969 | 10/1991 |
| GB | 406345 | 8/1932 | | WO | WO 95/14639 | 6/1995 |
| GB | 404938 A | 1/1934 | | WO | WO 96/07617 | 3/1996 |
| GB | 467481 A | 6/1937 | | WO | WO 96/15980 | 5/1996 |
| GB | 541357 A | 11/1941 | | WO | WO 97/48667 | 12/1997 |
| GB | 679536 A | 9/1952 | | WO | WO 98/37024 | 8/1998 |
| GB | 702143 A | 1/1954 | | WO | WO 99/14208 | 3/1999 |
| GB | 736641 A | 9/1955 | | WO | WO 9932397 A1 | 7/1999 |
| GB | 799567 A | 8/1958 | | WO | WO 0024674 A1 | 5/2000 |
| GB | 1046521 | 1/1964 | | WO | WO 0141919 A1 | 6/2001 |
| GB | 984446 A | 2/1965 | | WO | WO 0186220 A2 | 11/2001 |
| GB | 984633 A | 3/1965 | | WO | WO 02/26672 A2 | 4/2002 |
| GB | 1083594 A | 9/1967 | | WO | WO 02/059536 | 8/2002 |
| GB | 1286893 A | 8/1972 | | WO | WO 03/064357 | 8/2003 |
| GB | 1387668 A | 3/1975 | | WO | WO 2004/056758 | 7/2004 |
| GB | 1 493 538 | 4/1975 | | WO | WO 2005021476 A1 | 3/2005 |
| GB | 1414976 A | 11/1975 | | WO | WO 2005054167 A1 | 6/2005 |
| GB | 2173496 A | 10/1986 | | WO | WO 2005/097722 | 10/2005 |
| GB | 2336584 A | 10/1999 | | WO | WO 2005/115954 | 12/2005 |
| HU | 2002-003023 | 3/2004 | | WO | WO 2005/116004 | 12/2005 |
| JP | 3927230 B2 | 11/1939 | | WO | WO 2006020234 A1 | 2/2006 |
| JP | 50-062909 | 5/1975 | | WO | WO 2006/100311 A2 | 9/2006 |
| JP | 51021635 B | 7/1976 | | WO | WO 2006/100312 A2 | 9/2006 |
| JP | 55041858 A | 3/1980 | | WO | WO 2006/100313 A2 | 9/2006 |
| JP | 5629572 | 3/1981 | | WO | WO 2006/100314 A1 | 9/2006 |
| JP | 5699432 | 8/1981 | | WO | WO 2006/100315 A2 | 9/2006 |
| JP | 56-155009 | 12/1981 | | WO | WO 2006/100316 A1 | 9/2006 |
| JP | 60-258171 | 12/1985 | | WO | WO 2006/100317 A1 | 9/2006 |
| JP | 61-044833 | 3/1986 | | WO | WO 2006/100318 A2 | 9/2006 |
| JP | 61 112066 A | 5/1986 | | WO | WO 2006/100319 A1 | 9/2006 |
| JP | 61-140532 | 6/1986 | | WO | WO 2006/100320 A2 | 9/2006 |
| JP | 61-236749 | 10/1986 | | WO | WO 2006/106153 A2 | 10/2006 |
| JP | 62242638 A | 10/1987 | | WO | WO 2006/106154 A1 | 10/2006 |
| JP | 63195288 A | 8/1988 | | WO | WO 2006/106155 A2 | 10/2006 |
| JP | 2-137704 | 5/1990 | | WO | WO 2007/054505 A2 | 5/2007 |
| JP | 03014527 A | 1/1991 | | WO | WO2007/144335 | 12/2007 |
| JP | 3223267 A | 10/1991 | | WO | WO 2008/101866 | 8/2008 |
| JP | 03223267 A | 10/1991 | | WO | WO2008/107468 | 9/2008 |
| JP | 04089440 A | 3/1992 | | WO | WO 2008/110588 | 9/2008 |
| JP | 04-217637 | 8/1992 | | WO | WO2008/145729 | 12/2008 |
| JP | 06-009589 | 1/1994 | | WO | WO 2008/147473 | 12/2008 |
| JP | 625196 B2 | 4/1994 | | WO | WO 2008/152043 | 12/2008 |
| JP | 06184024 A | 7/1994 | | WO | WO 2008/152044 | 12/2008 |
| JP | 6321852 A | 11/1994 | | WO | WO 2009/000773 | 12/2008 |
| JP | 08-003087 | 1/1996 | | WO | WO 2009/016149 A2 | 2/2009 |
| JP | 859593 | 3/1996 | | WO | WO 2009026212 A1 | 2/2009 |
| JP | 09-2999953 | 11/1997 | | WO | WO2009/043796 A1 | 4/2009 |
| JP | 10139700 A | 5/1998 | | WO | WO 2009/077528 | 6/2009 |
| JP | 10-218810 | 8/1998 | | WO | WO 2009/077528 A1 | 6/2009 |
| JP | 1998218810 A | 8/1998 | | WO | WO 2009/095429 A1 | 8/2009 |
| JP | 20000344692 A | 12/2000 | | WO | WO 2009/121853 | 10/2009 |
| JP | 2001-037469 | 2/2001 | | WO | WO2009/121853 A1 | 10/2009 |
| JP | 2001-213827 A | 8/2001 | | WO | WO 2010/029039 | 3/2010 |
| JP | 2001-261308 | 9/2001 | | WO | WO 2010/029039 A1 | 3/2010 |
| JP | 2001-1261581 A | 9/2001 | | WO | WO 2010/029153 | 3/2010 |
| JP | 2001-276572 | 10/2001 | | WO | WO 2010/029153 A1 | 3/2010 |
| JP | 2002-02033 A2 | 1/2002 | | WO | WO 2010/066660 | 6/2010 |
| JP | 20020038195 A | 2/2002 | | | | |
| JP | 20020265986 A | 9/2002 | | | | |
| JP | 2002-363153 A | 12/2002 | | | | |
| JP | 2003-89680 A | 3/2003 | | | | |
| JP | 2003081891 A | 3/2003 | | | | |
| JP | 2003-183191 | 7/2003 | | | | |
| JP | 2003-206473 | 7/2003 | | | | |
| JP | 2004-518102 | 6/2004 | | | | |
| JP | 2004-216246 | 8/2004 | | | | |
| JP | 2005007841 A2 | 1/2005 | | | | |
| JP | 2005097177 A2 | 4/2005 | | | | |
| JP | 2005-513064 | 5/2005 | | | | |
| JP | 2007-008898 | 1/2007 | | | | |
| JP | 2009-263338 | 11/2009 | | | | |
| KR | 900006513 | 11/1987 | | | | |
| KR | 1019920003099 B1 | 4/1992 | | | | |
| KR | 10-514819 B1 | 9/2005 | | | | |
| PL | 136598 | 3/1986 | | | | |

OTHER PUBLICATIONS

Ullmann's Encyclopedia of Industrial Chemistry, 2005, "pH Measurement and Control", Wiley-VCH GmbH & Co. KGaA, Weinheim, 10.1002/14356007.e19_e01: pp. 1-31 (32 pgs).

Ma Zengxin et al, "recovery of Polyglycerol from residues of Synthetic Glycerol" Riyong Huaxue Gongye, 1997, 4, 21023 (English Abstract only).

Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.

Production and Prospect of the World Natural Glycerol by Zhu Shiyong, Cereals and Oils, vol. 1. 1997, pp. 33-38 (No English Translation).

Vinnolit; Vinnolit receives EU grant for water recycling project: Press Release, 2008: http://www.vinnolit.de/vinnolit.nsf/id/EN_Vinnolit_receives_EU_grant_for_water_recycling_project_.

N.W. Ziels, Journal of American Oil Chemists' Society, Nov. 1956, vol. 33, pp. 556-565.

Perry's Chemical Engineers Handbook, Sixth Edition. McGraw Hill Inc., (1984) Section 18.

Vol. 83: Unit Operations II of Ullmann's Encyclopedia of Industrial Chemistry, Fifth Completely Revised Edition, Published by VCH, 1988.

W. Giger et al., "14C/12C-Ratios in Organic Matter and Hydrocarbons Extracted from Dated Lake Sediments." Nuclear Instruments and Methods in Physics Research B5 (1984), 394-397. XP-002631954.

Jurgen O. Metzger, "Fats and Oils as Renewable Feedstock for Chemistry," Eur. J. Lipid Sci. Technol. (2009), 111, 865-876. XP-002631953.

Bruce M. Bell, "Glycerin as a Renewable Feedstock for Epichlorohydrin Production. The GTE Process," Clean-Soil, Air, Water, vol. 36, No. 8, (2008) pp. 657-661. XP-002631952.

Horsley, Lee H.—"Azeotropic Data—III", The Dow Chemical Co., Midland, MI, American Chemical Society 1973; pp. 1-4; 4 pgs.

Suzawa, Yoshikazu, et al—"Incineration System for Waste Liquid Containing Chlorinated Organic Compounds", Chemical Aparatuses, 1981, vol. 23, No. 11; 34 pgs; Translation in English provided.

D'Alonzo, R.P., et al—"Glyceride Composition of Processed Fats and Oils as Determined by Glass Capillary Gas Chromatography", Journal of American Oil Chemists' Society, 1982, vol. 59, No. 7, pp. 292-295; 4 pgs.

Chemical Engineering Handbook, $6^{th}$ Revised Edition, 2001, pp. 1-36; 56 pgs; Translation in English provided.

"Electrolytic cell test for electrolysis of epoxy sewage salt to prepare chlor-alkali", Process Equipment Department of Research Institute of Chloro-Alkali, Shengyang Chemical Plant, Liaoning Chemical Industry, Issue n°2, pp. 32-37, published Dec. 31, 1981; 17 pgs; Translation in English provided.

Chengxin, Ren, et al—"Analysis on the Composition of the Byproduct During the Manufacturing Process of S-Epichlorohydrin by GC-MS", Chemical Analysis and Meterage, 2003, vol. 12, Issue No. 3, pp. 25-26; 6 pgs; Translation in English provided.

Encyclopedia of Chemical Technology, vol. 5, Nov. 1993; 6 pgs; Translation in English provided.

"Manufacture and use of epoxy resin", edited by Shanghai Resin Factory, published by China Petrochemical Press, First Edition, Oct. 1974; 16 pgs; Translation in English provided.

Gilman, Henry, et al—"Organic synthesis", Part 1, published by Scientific Publishing, 1957 (with abstract); 4 pgs.

Handbook of Chemical Products, Heavy Organic Chemicals, Second edition, published by Chemical Industry Press, Jan. 1995; 13 pgs; Translation in English provided.

Kiseleva, R. A., et al—"Study of the Interaction of Dibasic Acids with Glycerol", J. App. Chem. USSR, 1971, vol. 44, pp. 2086-2090; 5 pgs.

Handbook of Corrosion Data and Material Selection, published by Chemical Industry Press, edited by Jingyi Zuo, Yu Zuo; First edition, Oct. 1995, 5 pgs; Translation in English provided.

Handbook of Azeotropic Mixture, edited by Information Department of Comprehensive Scientific Technology Research Institution of Fushun City, 1993; 8 pgs; Translation in English provided.

"Industry Chemical Reaction and Application", published by Chinese Scientific Technology University Press, 1999; 4 pgs; Translation in English provided.

"Epoxy resin", published by Shanghai People's Publishing House, 1971; Translation in English provided; 21 pgs.

Boschan, Robert, et al—"The Role of Neighboring Groups in Replacement Reactions. XXI. Front-side Participation of Acetoxy Group. Catalytic Effect of Acetic Acid on the Reaction of Glycols with Hydrogen Chloride", Journal of the American Chemical Society, 1956, vol. 78, pp. 4921-4925; 5 pgs.

Encyclopedia for Chinese Adult Education, 1994, p. 623; 10 pgs; Translation in English provided.

Medium and Long-term Opportunities and Risks of the Biotechnological Production of Bulk Chemicals from renewable Resources—The Potential of White Technology—The BREW project—Final Report—prepared under the European Commission GRXTH Programme (DG Research) Ulrecht, Sep. 2006 (pp. 29-31).

Ullmann's Encyclopedia Industrial Chemistry, $5^{th}$ Ed. vol. A6 (1988) pp. 401-477.

Polymer Science Dictionary, M.S.M., Elsevier Applied Chemistry, London & New York, 1989 p. 86.

Perry's Chemical Engineers' Handbook, $6^{th}$ Edition, Section 21, pp. 21-55.

E. Milchert et al., "Installation for the Recovery of Dichloropropanols and Epichlorohydrin from the Waste Water in Epichlorohydrin Production", Pol. J. Appl. Chem., vol. 41, p. 113-118 (1997).

Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V;—2005 p. 81/-8/5., vol. 5.

Klaus Weissermel, et al., "Industrial Organic Chemistry," ($3^{rd}$ Completely Revised Edition); VCH 1997. p. 93-98.

Klaus Weissermel, et al., "Industrial Organic Chemistry," ($3^{rd}$ Completely Revised Edition); VCH 1997. p. 276-277.

Klaus Weissermel, et al., "Industrial Organic Chemistry," ($3^{rd}$ Completely Revised Edition); VCH 1997. p. 347-355.

Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).

M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/ English Abstract.

Herman A. Bruson, et al., "Thermal Decomposition of Glyceryl Carbonates," Journal of the American Chemical Society, vol. 74, Apr. 1952 pp. 2100-2101.

Perry's Chemical Engineers Handbook 7th Ed., 11th Section, 1997, pp. 11.1-11.118 (submitted into two parts).

Perry's Chemical Engineers Handbook 7th Ed., 13th Section, 1997, pp. 13.1-13.108.

Perry's Chemical Engineers Handbook 7th Ed., 15th Section, 1997, pp. 15.1-15.47.

Ullmann's Encyclopedia of Industrial Chemistry 5th Ed., vol. A23, 1993, pp. 635-636.

Ullmann's Encyclopedia of Industrial Chemistry 5th Ed., vol. A13, 1989, p. 289.

Ullmann's Encyclopedia of Industrial Chemistry 5th Ed., vol. A11, 1988, pp. 354-360.

Attached Application No. FR 06.05325 filed Jun. 14, 2006 by Solvay S.A.—priority document to EP2007/55742 published as WO 2007/144335 (attached herein) 17 pgs.

Attached Application No. FR 07.53863 filed Mar. 15, 2007 by Solvay S.A. and published as FR2913683, 19 pgs (attached herein)—priority document to EP2007/55742 published as WO2007/144335 29 pgs (attached herein).

Gibson, "The preparation, properties, and uses of glycerol derivatives, Part III. The Chlorohydrins", 1931, Chemistry and Industry, Chemical Society, pp. 949-975.

Carre et al, 1931, "La transformation des alcools polyatomiques en mono-et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.

Fauconner, 1888, "Preparation de l'epichlorhydrine", Bull. Soc. Chim. FR, No. 50, pp. 212-214 (with enclosed translation in English).

Ullmann's Encyclopedia of Industrial Chemistry, "Industrially important epoxides", 1987, Fifth Completely Revised Edition, vol. A9, pp. 539-540.

Bonner et al, "The composition of constant boiling hydrochloric acid at pressures of 50 to 1220 millimeters", 1930, Journal of American Chemical Society, vol. 52, pp. 633-635.

Muskof et al, "Epoxy Resins" in Ullmann's Encyclopedia of Industrial Chemistry, 1987, 5th Ed., vol. A9, pp. 547-563.

Novelli, A., "The preparation of mono-and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.
Rudnenko, EV, et al., 1988, Lakokrasochnye Materially i 1kh Primenenie, 4 69-71 (CA Summary) XP 002465276, 1 pg.
Kirk-Othmer Encyclopedia of Chemical Technology, 1978, 3rd Ed., vol. 4, Blood, Coagulants and Anticoagulants to Cardiovascular Agents. p. 847-848.
Jeffrey Lutje Spelberg, et al, A Tandem Enzyme Reaction to Produce Optically Active Halohydrins, Epoxides and Diols, Tetrahedron: Asymmetry, Elsevier Science Publishers, vol. 10, No. 15, 1999, pp. 2863-2870.
Oleoline.com. Glycerine Market report, Sep. 10, 2003, No. 62, 31 pgs.
Notification Under Act. No. 100/2001, Coll. As Amended by Act No. 93/2004, Coll. To the extent of Annex No. 4 (SPOLEK) Nov. 30, 2004, 80 pgs.
Documentation Under Act. No. 100/2001 Coll. As Amended by Act. No. 93/2004 Coll in the scope of appendix No. 4 (SPOLEK) Jan. 11, 2005, 86 pgs.
K. Weissermel & H.J. Arpe, Industrial Organic Chemistry, Third, Completely Revised Edition, VCH, 1997, pp. 149 & 275.
Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & Sons, Inc.
Ullmann's Encyclopedia of Industrial Chemistry, Fifth, Completely Revised Edition, 1988, vol. A13, pp. 292-293.
The Merck Index, Eleventh Edition, 1989, pp. 759-760.
Ullmann's Encyclopedia of Industrial Chemistry, Fifth completely Revised Edition, vol. A1, 1985, pp. 427-429.
Ullmann's Encyclopedia of Industrial Chemistry, Fifth Completely Revised Edition, vol. A6, 1986, pp. 240-252.
Hancock, E.G., Propylene and its Industrial Derivatives, 1973, pp. 298-332.
K. Weissermel & H.J. Arpe, Industrial Organic Chemistry, Third, Completely Revised Edition, VCH 1997, pp. 149-163.
K. Weissermel & H.J. Arpe, in Industrial Organic Chemistry, Third, Completely Revised Edition, VCH 1997, pp. 275-276.
Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and similar passages but retrieved from the English Fifth Edition of the Book, 1987).
Perry's Chemical Engineers' Handbook, Sixth Edition, Robert H. Perry, Don Green, 1984, Section 21-64 to 21-68.
Iwanami et al, Dictionary of Physics and Chemistry, Third Edition, Ryo Midorikawa /Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.
Kirk Othmer Encyclopedia of Chemical Technology, Third Edition, vol. 12, 1980, pp. 1002-1005.
Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.
Product Brochure of De Dietrich Company, Apr. 1996, pp. 3, 8 and 9 w/English translation of p. 8, left column, column lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
Catalogue of Nittetu Chemical Engineering Ltd. (Published in Mar. 1994).
12093 Chemicals, The Chemical Daily Co., Ltd. (Published on Jan. 22, 1993) with attached English translation of relevant excerpts, 24 pgs.
Chemicals Guide, Chemical Daily Co., Ltd. (Published on Jun. 15, 1990) with attached English translation of relevant excerpts.
[Unknown Author], Kirk Othmer Encyclopedia of Chemical Technology—vol. 2, p. 156, John Wiley and Sons, 1992.
U.S. Appl. No. 12/681,083, filed Mar. 31, 2010, Bobet, et al.
J.B. Conant, et al, "Glycerol a,y-dichlorohydrin", Organic Syntheses Coll., 1941, vol. 1, p. 292-294 (5 pp.).
Gilman H., Organic Synthesis, Section 1, pp. 234-235 (no date)—attached English translation only.
Industrial Chemical Encyclopedia 5, p. 457 (no date)—attached English translation only.
"Epoxy resins", p. 36-46, by Shangai Resin Plant, Shangai People's Press, 1971—attached English translation only.
Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.
"Rainwater Harvesting and Utilization" (United Nations Environment Program) Mar. 2002; XP003003726; Internet Citation extracted online on Jan. 1, 2006: URL:http://www.unep.or.ip/letc/ Publication—4 pp.
Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.
Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.
Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.
Laine, D.F. et al. "The destruction of organic pollutants under mild reaction conditions; A review" Michochemical Journal, vol. 85, No. 2, 2007 pp. 183-193; available online Aug. 17, 2006; 12 pp.
U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.
U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 11/915,046, filed Nov. 20, 2007, Krafft, et al.
U.S. Appl. No. 60/734,636, filed Nov. 8, 2005.
U.S. Appl. No. 11/915,088, filed Nov. 20, 2007, Krafft, et al.
U.S. Appl. No. 60/560,676, Apr. 8, 2004, Gilbeau, et al. et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Boulos, et al.
U.S. Appl. No. 12/600,018, filed Nov. 13, 2009, Borremans.
U.S. Appl. No. 12/663,753, filed Dec. 9, 2009, Krafft, et al.
U.S. Appl. No. 12/663,887, filed Dec. 10, 2009, Krafft, et al.
U.S. Appl. No. 12/663,744, filed Dec. 9, 2009, Boulos, et al.
New Experimental Chemical Course 1, Basic Operation I, Section 4, Separation and Purification, pp. 251-252, Issued Sep. 20, 1975 (with English Translation).
Copyright Mar. 1992, Advanced Organic Chemistry, $4^{th}$ Ed., pp. 889, 908 and 937.

Yong, K.C., et al., "Refining of Crude Glycerine Recovered from Glycerol Residue by Simple Vacuum Distillation," Journal of Oil Palm Research, vol. 13, N°. 2, Dec. 2001, pp. 39-44.

Friedel et Silva, Bulletin de la Société Chimique de Paris, Année 1873, 1er semestre—Nouvelle Série—Tome XIX, p. 98.

I.S. Neuberg, Biochemische Zeitshrift, 1930, vol. 221, pp. 492-493.

F. Krausz Ann. De Chimie, 12e série, t. 4 Nov.-Dec. 1949, pp. 811-931.

Glycerin : An overview, Soap and Detergent Association. Copyright 1990 by the Soap and Detergent Association.

Chemical and Engineering News, 1948, 26 (38), pp. 2770-2771.

Fairbourn et al., "The Partial Esterification of Polyhydric Alcohols. Part XII. The Function of Ethylene-oxide Rings," J. Chem. Soc. 1932, pp. 1965-1972, Received, Apr. 6, 1932.

Clarke et al., Organic Syntheses, Coll., vol. 1, p. 233, (1941); vol. 3, p. 47, (1923).

Braun, Organic Syntheses, Coll., vol. 2, p. 256, (1943); vol. 6, p. 30, (1936).

Conant et al. Organic Syntheses, Coll., vol. 1, p. 292, (1941); vol. 2, p. 29, (1922).

Bull. Soc. Chim. Fr. (1943), 10, pp. 52-58, with English Translation.

Schröder et al. "Glycerol as a By-Product of Biodiesel Production in Diets for Ruminants," Institute of Animal Nutrition, Physiology and Metabolism, University of Kiel, 24098 Kiel.

"Chemical Properties and Derivatives of Glycerol", (1965), published by Glycerine Producers' Association in New York, pp. 1-20.

G.W. Busby and D.E. Gosvenor, "The Purification of Glycerin by Ion-Exchange," The Journal of the American Oil Chemists' Society, vol. 29, N°. 8, pp. 318-320 (1952).

L.L. Lamborn, "Modern Soaps, Candles and Glycerin," D. Van NOstrand Company, London, third edition 1918, pp. 542-550, 573-574.

G. Knothe, "Historical perspectives on vegetable oil-based diesel fuels", Inform, vol. 12, Nov. 2001. pp. 1103-1107.

U. Schuchardt et al., "Transesterification of Vegetable Oils: a Review," J. Braz. Chem. Soc., vol. 9, N°. 1, 199-210, 1998.

S. Claude, "Research of new outlets for glycerol—recent developemnts in France," Fett/Lipid 101 (1999), Nr. 3, S 101-104.

C.B. Prakash,"A critical review of Biodiesel as a Transportation Fuel in Canada," for the Transportation Systems Branch Air Pollution Prevention Directorate Enviornment Canada, Mar. 25, 1998, pp. 1-104.

H. Fukuda et al., "Biodiesel Fuel Production by transesterification of Oils", Journal of Bioscience and Bioengineering, vol. 92, No. 5, pp. 405-416 (2001).

Encyclopedia of Experimental Chemistry I, Basic Operation I, edited by The Chemical Society of Japan, Maruzen Co., Ltd., Nov. 5, 1990, 4th Edition, pp. 161 to 165 and 184 to 191 (no English translation available.

Encyclopedia of Chemistry 3, edited by Editorial Committee of Encyclopedia of Chemistry, Kyoritsu Shuppan Co., Ltd., Sep. 30, 1960, 1st Edition, 1st printing, pp. 312 and 313 (no English translation available).

Clarke et al., Org Synth., Coll. vol. 1, p. 233-234, 1964.

Braun, Org. Synth., Coll., vol. 2, p. 256-259, 1957.

Kirk Othmer Encyclopedia of Chemical Technology, 3rd Edition, vol. 9, pp. 267-289, 1980.

\* cited by examiner

I.

II.

III.

IV.

V.

XIII

EPICHLOROHYDRIN, MANUFACTURING PROCESS AND USE

CROSS-REFERENCE TO RELATED APPLICATIONS

The present patent application is a U.S. national stage application under 35 U.S.C. §371 of International Application No. PCT/EP2008/057247 filed Jun. 11, 2008, which claims the benefit of the French Patent applications No. FR 07/55696 filed on Jun. 12, 2007, No. FR 07/57751 filed on Sep. 21, 2007, of the U.S. Provisional Patent Application No. 61/013,672 filed on Dec. 14, 2007 and of the U.S. Provisional Patent Application No. 61/007,661 filed on Dec. 14, 2007, the content of all of these applications being incorporated herein by reference for all purposes.

The present invention relates to an epichlorohydrin-based product, to a process for the manufacture and purification thereof and to the use of the product in various manufactures.

Epichlorohydrin is a reaction intermediate in the manufacture of epoxy resins, synthetic elastomeres, glycidyl ethers, polyamide resins, etc. (Ullmann's Encyclopedia of Industrial Chemistry, Fifth Edition, Vol. A9, p. 539). The epichlorohydrin can be manufactured, for instance, by dehydrochlorination of dichloropropanol derived from hypochlorination of allyl chloride. The epichlorohydrin thus obtained is not suitable for certain applications.

The object of the present invention is to provide a product containing epichlorohydrin which does not have these disadvantages.

The invention hence relates to a product containing epichlorohydrin and trichloropropane, wherein the amount of trichloropropane is of less than 0.01 g of trichloropropane per kg of product.

One of the essential characteristics of the invention resides in the low amount of trichloropropane present in the epichlorohydrin product. The presence of trichloropropane amongst other halogenated hydrocarbons in epichlorohydrin have indeed proven troublesome in some of the applications, such as for example, in manufacturing epoxy resins intended for the electrical component and printed circuit industry. Some halogenated hydrocarbons, among which trichloropropane, for instance are or are suspected to be carcinogenic, are suspected to have development toxicity, reproductive toxicity, cardiologic toxicity, endocrine toxicity, immunotoxicity and toxicity to the liver, the kidneys, the nerves, the respiratory tract and to the skin. They can remain in the final products and possibly degrade with a concomitant deterioration of the properties of the final products. They can exhibit or degrade in compounds exhibiting some toxicity leading to safety issues especially when the final products are intended to be in contact with food and drink. Moreover, they can accumulate in and contaminate industrial waters such as wastewaters for instance or water containing pulp that is recycled in the pulp and paper industry. In the latter case, their higher concentration can increase contamination of the paper made using the recycled water.

The epichlorohydrin content in the product is generally greater than 900 g of epichlorohydrin per kg of product, preferably at least 950 g/kg, more preferably at least 990 g/kg and most particularly preferably at least 999 g/kg.

The trichloropropane in the product according to the invention is present, in an amount of generally less than or equal to 0.008 g/kg of product, often of less than or equal to 0.006 g/kg, frequently of less than or equal to 0.004 g/kg, commonly of less than or equal to 0.002 g/kg, in many cases of less than or equal to 0.001 g/kg, and particularly of less than or equal to 0.0005 g/kg. That content is usually of at least 0.001 mg/kg.

The trichloropropane may be selected from any isomer of trichloropropane, alone or in combination, and the content of TCPa in the product according to the invention refers to the sum of all the isomers.

The trichloropropane can be selected from 1,2,3-trichloropropane, 1,1,1-trichloropropane, 1,1,3-trichloropropane, 1,1,2-trichloropropane and any mixtures of at least two of them. The trichloropropane is often 1,1,1-trichloropropane.

The product according to the invention may contain in addition to trichloropropane and epichlorohydrin, at least one halogenated hydrocarbon different from trichloropropane. That halogenated hydrocarbon can be chosen from chloropropene, trichloropropene, chloropropanol, chloropropenol, dichloropropene, dichloropropane, dichloropropanol, monochloropropanediol, chloroethers, monochlorobenzene, and any mixture of at least two of them.

The content of that halogenated hydrocarbon in the product is usually of less than 1 g/kg of product, commonly less than or equal to 0.8 g/kg of product, usually less than or equal to 0.6 g/kg, in many cases less than or equal to 0.5 g/kg, often less than or equal to 0.4 g/kg, frequently less than or equal to 0.2 g/kg, more often less than or equal to 0.1 g/kg, more frequently less than or equal to 0.05 g/kg, in particular less than or equal to 0.01 g/kg, and specifically less than or equal to 0.001 g/kg. This content is generally greater than or equal to 0.001 mg/kg.

The halogenated hydrocarbon may be an aliphatic or an aromatic halogenated hydrocarbon, optionally containing oxygen, preferably an aliphatic halogenated hydrocarbon, such as:

chloropropene, often 2-chloro-1-propene, frequently 1-chloro-1-propene cis, usually 1-chloro-1-propene trans, specifically 3-chloro-1-propene, and any mixture of at least two of them chloropropane, often 2-chloropropane, frequently 1-chloropropane, and any mixture of at least two of them chloromethane, often dichloromethane, frequently trichloromethane, usually tetrachloromethane, and any mixture of at least two of them dichloroethane, often 1,2-dichloroethane, chloroethanol, often 2-chloroethanol, trichloropropene, often 1,3,3-trichloro-1-propene-cis, frequently 1,3,3-trichloro-1-propene-trans, usually 1,2,3-trichloropropene-cis, specifically 1,2,3-trichloropropene-trans, and any mixture of at least two of them chloropropanol, often 3-chloro-1-propanol, chloropropenol, often 2-chloro-2-propen-1-ol, frequently 3-chloro-2-propene-1-ol cis and specifically 3-chloro-2-propene-1-ol trans, and any mixture of at least two of them dichloropropene, often cis-1,3-dichloropropene, frequently trans-1,3-dichloropropene, usually 3,3-dichloro-1-propene, frequently 2,3-dichloro-1-propene, usually 1,3-dichloro-1-propene-cis, specifically 1,3-dichloro-1-propene-trans, and any mixture of at least two of them, dichloropropane, preferably 1,3-dichloropropane, 1,2-dichloropropane, 2,2-dichloropropane, and any mixture thereof dichloropropanol, often-1,3-dichloropropan-2-ol, 2,3-dichloropropan-1-ol, and mixtures thereof, monochloropropanediol, often 3-chloro-1,2-propanediol, frequently 2-chloro-1,3-propanediol, and mixtures thereof, and chloroethers, preferably chosen from chloroethers of crude
formula: $C_6H_{10}Cl_2O_2$, $C_6H_{12}Cl_2O$, $C_6H_9Cl_3O_2$, $C_6H_{11}Cl_3O_2$, and mixtures of at least two of them,
of crude formula $C_4H_7ClO_2$, $C_6H_9Cl_3$, $C_6H_9Cl_3O_2$, $C_9H_{17}Cl_3O_4$, $C_9H_{15}Cl_5O$, $C_3H_3Cl_3$, and mixtures of at least two of them
dichloroepoxypropane.

Haloketones and epichlorohydrin are not considered to be halogenated hydrocarbons.

Aromatic halogenated hydrocarbons comprise at least one ring of aromatic nature and a halogen atom. The halogen atom is preferably directly attached to the aromatic ring. The halogen may be chosen from fluorine, chlorine, bromine, iodine and mixtures thereof. Chlorine is preferred. The aromatic ring may be mononuclear or polynuclear, and is preferably mononuclear. The aromatic halogenated hydrocarbons may be chosen from mono-, di-, tri-, tetra-, penta- and hexachloro-benzenes and/or naphthalenes. Monochlorobenzene is particularly preferred.

Without wishing to be tied to one theoretical explanation, it is believed that monochlorobenzene may come from the process for manufacturing epichlorohydrin, in particular when this is obtained by dehydrochlorination of dichloropropanol. More specifically, it is believed that monochlorobenzene may be present in the dichloropropanol, in particular when this is obtained by a process for chlorinating glycerol using a chlorinating agent containing hydrogen chloride. More specifically still, it is believed that chlorobenzene may be present in the hydrogen chloride, in particular when this comes from another manufacturing process, such as the manufacture of isocyanates, diisocyanates or polyisocyanates, such as for example 4,4-methylenediphenyl diisocyanate (MDI) or toluene diisocyanate (TDI) or hexamethylene-1,6-diisocyanate (HDI).

The product according to the invention can contain chloropropene, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The chloropropene may be selected from 2-chloro-1-propene, 1-chloro-1-propene cis, 1-chloro-1-propene trans, 3-chloro-1-propene, and any mixture of at least two of them.

The product according to the invention can contain trichloropropene, in an amount a content usually less than or equal to 0.8 g/kg of product, generally less than or equal to 0.6 g/kg, commonly less than or equal to 0.5 g/kg, in many cases less than or equal to 0.4 g/kg, often less than or equal to 0.2 g/kg, frequently less than or equal to 0.1 g/kg, particularly less than or equal to 0.05 g/kg, specifically less than than or equal to 0.01 g/kg. A content of less than or equal to 0.001 g/kg gives good results. That content is usually of at least 0.001 mg/kg. The trichloropropene may be selected from 1,3,3-trichloro-1-propene-cis, 1,3,3-trichloro-1-propene-trans, 1,2,3-trichloropropene-cis, specifically 1,2,3-trichloropropene-trans and any mixtures of at least two of them.

The product according to the invention can contain chloropropenol, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The chloropropenol may be selected from 2-chloro-2-propen-1-ol, 3-chloro-2-propene-1-ol cis, 3-chloro-2-propene-1-ol trans and any mixtures of at least two of them.

The product according to the invention may contain dichloropropene, in a content a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The dichloropropene may be selected from 3,3-dichloro-1-propene, 2,3-dichloro-1-propene, 1,3-dichloro-1-propene-cis, 1,3-dichloro-1-propene-trans, and any mixtures of at least two of them.

The product according to the invention can contain dichloropropane, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The dichloropropane may be selected from 1,3-dichloropropane, 1,2-dichloropropane, 2,2-dichloropropane, and any mixture of at least two of them.

The product according to the invention can contain dichloropropanol, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The dichloropropanol may be selected from 1,3-dichloropropan-2-ol, 2,3-dichloropropan-1-ol and any mixtures thereof.

The product according to the invention can contain monochloropropanediol, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The monochloropropanediol may be selected from 3-chloro-1,2-propanediol, 2-chloro-1,3-propanediol and any mixtures thereof.

The product according to the invention usually can contain chloroethers in in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The chloroethers may be selected from chloroethers of crude formula $C_6H_{10}Cl_2O_2$, $C_6H_{12}Cl_2O$, $C_6H_9Cl_3O_2$, $C_6H_{11}Cl_3O_2$, and any mixtures thereof.

The product according to the invention usually contains chlorobenzene, often monochlorobenzene, in an amount in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg.

The product according to the invention may also contain in addition, compounds which are not halogenated hydrocarbons such as defined above, such as for example:
- aldehydes, like acetaldehyde, acrolein, isobutanal, isopentanal
- alkyl glycidyl ether, like methyl glycidyl ether,
- ketones, like acetone, chloroacetone, cyclopentanone, 2-butanone, cyclohexanone, 2-methyl-2-cyclopentene-1-one, 3,5-dimethyl-2-cyclohexene-1-one ketone of crude formula $C_5H_{10}O$, $C_6H_{12}O$,
- aliphatic alcohols, like isopropanol, allyl alcohol, glycerol,
- aromatic alcohols like phenol
- hydroxyketones like hydroxyacetone and
- epoxides different from epichlorohydrin, like propylene oxide, 1,2-epoxyhexane, glycidol,
- hydrocarbons like methylcyclopentane, ethylbenzene, compounds of crude formula $C_6H_{10}O$, $C_7H_{10}O$, $C_7H_{14}O_2$, $C_6H_8O_2$, $C_9H_{10}O_2$.

The product according to the invention can contain at least one aldehyde, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The aldehyde may be selected from acetaldehyde, acrolein, isobutanal, isopentanal and any mixtures of at least two of them.

The product according to the invention can contain acrolein in an amount usually of less than 0.07 g/kg of product, generally at most 0.01 g/kg commmonly at most 0.005 g/kg. This content is usually at least 0.001 g/kg.

The product according to the invention can contain at least one alkyl glycidyl ether, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The alkyl glycidyl ether may be selected from methyl-, ethyl-, propyl-, butyl glycidyl ethers, and any mixtures of at least two of them.

The product according to the invention can contain methyl glycidyl ether in an amount usually of at most 0.5 g/kg of product, generally at most 0.1 g/kg and commonly at most 0.05 g/kg. This content is usually of at least 0.001 g/kg.

The product according to the invention can contain ketones, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The ketones may be selected from acetone, chloroacetone, 2-butanone, cyclopentanone, cyclohexanone, 2-methyl-2-cyclopentene-1-one, 3,5-dimethyl-2-cyclohexene-1-one, ketones of crude formula $C_5H_{10}O$, $C_6H_{12}O$, and any mixtures of at least two of them.

The product according to the invention can contain cyclopentanone in an amount usually higher than or equal to 0.001 mg/kg, generally higher than or equal to 0.01 mg/kg, commonly higher than or equal to 0.1 mg/kg and in many cases higher than or equal to 0.001 g/kg. That content is usually lower than or equal to 0.5 g/kg, generally lower than or equal to 0.3 g/kg, commonly lower than or equal to 0.1 g/kg, in many cases lower than or equal to 0.05 g/kg, often lower than or equal to 0.01 g/kg and particularly lower than or equal to 0.005 g/kg. That content is usually higher than or equal to 0.001 mg/kg, generally higher than or equal to 0.01 mg/kg, commmponly higher than or equal to 0.1 mg/kg, in many cases higher than or equal to 0.5 mg/kg and in particular higher than or equal to 1 mg/kg The product according to the invention can contain chloroacetone in an amount usually of less than 0.05 g/kg of product, generally at most 0.03 g/kg and commonly at most 0.01 g/kg. This content is usually at least 0.001 g/kg The product according to the invention can contain aliphatic alcohols, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The aliphatic alcohols may be selected from isopropanol, allyl alcohol, glycerol, and any mixtures of at least two of them.

The product according to the invention can contain hydroxyketones, in a content in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The hydroxyketone is often hydroxyacetone.

The product according to the invention can contain epoxides different from epichlorohydrin, in a content usually less than or equal to 0.8 g/kg of product, generally less than or equal to 0.6 g/kg, in many cases less than or equal to 0.5 g/kg, often less than or equal to 0.4 g/kg, commonly less than or equal to 0.2 g/kg, advantageously less than or equal to 0.1 g/kg, particularly less than or equal to 0.05 g/kg, specifically less than or equal to 0.01 g/kg. Values less than or equal to 0.001 g/kg give good results. That content is usually of at least 0.001 mg/kg. The epoxide may be selected from propylene oxide, 1,2-epoxyhexane, glycidol, and any mixtures of at least two of them.

The product according to the invention can contain glycidol in an amount usually of at most 0.5 g/kg of product, generally of at most 0.2 g/kg, frequently of at most 0.10 g/kg of product, commonly of at most 0.05 g/kg of product, often of at most 0.01 g/kg and frequently of at most 0.005 g/kg.

The product according to the invention usually contains glycerol, hydroxyacetone and glycidol, of which the sum of the contents is usually less than 0.1 g/kg of product, commonly at most 0.01 g/kg and generally at most 0.005 g/kg. This content is usually at least 0.001 g/kg.

The invention also relates to a process for manufacturing a product containing epichlorohydrin, wherein the amount of trichloropropane is of less than 0.01 g of trichloropropane per kg of product, comprising the following steps:

a) in a liquid reaction medium, a mixture of dichloropropanol containing 1,3-dichloro-2-propanol and 2,3-dichloro-1-propanol, in which the 1,3-dichloro-2-propanol content is at least 10 wt %, is reacted with at least one basic compound in order to form epichlorohydrin and at least one salt; and b) at least one part of the liquid reaction medium from step a) is subjected to a settling operation in which a first fraction containing most of the epichlorohydrin which was contained in the part of the reaction medium from step a) before the settling operation is separated from a second fraction containing most of the salt which was contained in the part of the reaction medium from step a) before the settling operation; and c) the first fraction separated in step b) is subjected to at least one supplementary treatment chosen from dilution, concentration, evaporation, distillation, stripping, liquid/liquid extraction and adsorption operations, alone or in combination.

In the rest of the document the expression "dichloropropanol" will be used to denote the dichloropropanol mixture.

The expression "most of" is understood to mean "half and more than half of", i.e. 50% by weight or more than 50% by weight.

The halogenated hydrocarbons may especially be produced during the various steps of the dichloropropanol manufacturing process.

The dichloropropanol from step a) of the process according to the invention may be produced, for example, by chlorination of glycerol and/or by hypochlorination of allyl chloride, the allyl chloride being itself produced by chlorination of propylene. The glycerol may be obtained from oil or grease of plant or animal origin. Oil-producing plant or crops are for example corn, cashew nut, oat, palm, lupine, rubber seed, kenaf, calendula, cotton, hemp, soybean, coffee, linseed, hazelnut, euphorbia, pumpkin seed, coriander, mustard, camelina, sesame, crambe, safflower, buffalo gourd, rice, tung oil tree, sunflower, cocoa, peanut, opium poppy, rapeseed, olive tree, piassaya, gopher plant, castor bean, bacuri, pecan, jojoba, babassu palm, jatropha, e.g. jatropha Curcas L., Chinese tallow or *Tridica Sebifera* L., macadamia nut, brazil nut, avocado, coconut, oiticia, buriti palm, pequi, macauba palm and oil palm. Oil-producing algae are for example *Neochloris oleoabundans, Scenedesmus dimorphus, Euglena gracilis, Phaeodactylum tricornutum, Pleurochrysis carterae, Prymnesium parvum, Tetraselmis chui, Tetraselmis suecica, Isochrysis galbana, Nannochloropsis salina, Nannochloris atomus Butcher, Nannochloris maculata Butcher, Nannochloropsis gaditana Lubian*, and *Nannochloropsis oculata*, Algal strains such as *Botryococcus braunii, Botryococcus, Dunaliella tertiolecta, Nannochloris* sp., *Spirulina* species, Chlorophyceae (green algae) and Bacilliarophy (diatom algae). Methyl glycidyl ether may come from glycerol methyl ethers which are impurities of a glycerol obtained by transesterification of fats or oils of animal or vegetable origin, as described in Patent Applications FR 06/05325 and FR 07/53863 filed in the name of Solvay SA, the contents of which are incorporated herein by reference. The haloketones such as, for example, chloroacetone may be generated in the dichloropropanol manufacturing process by chlorination of glycerol and/or during step a) of the process according to the invention.

Steps a) and b) of the process used to manufacture the product according to the invention may be carried out under conditions such as those described in Applications FR 07/53375 and FR 07/55448 filed in the name of Solvay SA.

The liquid reaction medium from step a) may especially contain an organic solvent, such as trichloropropane for example.

The dichloropropanol used in step a) can be fed to step a) as an aqueous composition, as an organic composition or a mixture thereof.

The dichloropropanol content of the aqueous composition is usually higher than or equal to 1 g/kg, often higher than or equal to 10 g/kg, frequently higher than or equal to 50 g/kg and particularly higher than or equal to 90 g/kg. That content is generally lower than or equal to 500 g/kg, usually lower than or equal to 200 g/kg, often lower than or equal to 150 g/kg, frequently lower than or equal to 120 g/kg and particularly lower than or equal to 110 g/kg. A content of 100 g/kg is convenient.

The dichloropropanol content of the organic composition is usually higher than or equal to 500 g/kg, often higher than or equal to 750 g/kg, frequently higher than or equal to 800 g/kg and particularly higher than or equal to 850 g/kg. that content is usually lower than or equal to 999 g/kg, often lower than or equal to 950 g/kg, frequently lower than or equal to 900 g/kg and particularly lower than or equal to 880 g/kg. A content of 870 g/kg is convenient.

In a particular embodiment, the mixture of dichloropropanol used in step a) of the process according to the invention can contain at least one chloro alkoxy propanol, as described in U.S. P 61/007,661 of SOLVAY SA. The content of chloro alkoxy propanol in the dichloropropanol is usually lower than or equal to 0.2 g/kg, generally lower than or equal to 0.1 g/kg, often lower than or equal to 0.06 g/kg and frequently lower than or equal to 0.04 g/kg. This content is usually higher than or equal to 0.001 g/kg.

The chloro alkoxy propanol is often a chloro methoxy propanol. The chloro methoxy propanol can be selected from 2-chloro-3-methoxy-1-propanol, 1-chloro-3-methoxy-2-propanol, 3-chloro-2-methoxy-1-propanol, and any mixture of at least two of them.

Steps a) to c) of the process for obtaining the product according to the invention may independently be carried out in continuous or batch mode. It is preferred to carry out steps a) to c) in continuous mode.

In the process according to the invention, the reaction from step a) may be carried out in one or more reaction zones, preferably in at least two reaction zones, more preferably in at least three reaction zones and more particularly preferably at least four reaction zones. The reaction zones may be composed of volumes assembled in a single jacket or volumes in separate jackets. In the case where the volumes are assembled in a single jacket, the reaction zones may be positioned horizontally or vertically with respect to one another. In the case where the zones are positioned horizontally with respect to one another, the transfer from one zone to another may take place by gravity or by forced circulation. In the case of circulation by gravity, the transfer may be carried out with or without settling in one or in several channels. Transfer in a single channel without settling is preferred. In the case where the zones are assembled vertically, the transfer from one zone to another may take place by gravity or by forced circulation. Transfer by gravity is preferred. The implementation of step a) in a mechanically stirred column that is subdivided by perforated dividing plates is particularly preferred. The stirring may be carried out by any known means, for example by rotation of a spindle in the liquid medium or by pulsing of the flow. Columns stirred by rotation of a spindle are particularly preferred. These reaction zones may be placed in any configuration, in series, in parallel or some in series and others in parallel.

In the process according to the invention, the reaction zones may be supplied independently of one another with dichloropropanol, with the basic compound, with water or with at least two of these compounds. When several reaction zones are in series, it is preferred to supply the major part of the basic compound to the first reaction zone of the series.

The expression "reaction zones" is understood to mean zones where all the compounds needed for the reaction from step a) are found, namely dichloropropanol, the basic compound and an optional reaction solvent.

In the process for manufacturing the epichlorohydrin-based product according to the invention, the dichloropropanol may be dichoropropanol extrinsic to the process according to the invention, recycled dichloropropanol or a mixture of the two, such as has been defined before in Applications FR 07/53375 and FR 07/55448 filed in the name of Solvay SA. The expression "recycled dichloropropanol" is understood to mean dichloropropanol which has been separated in a step subsequent to step b) in the process according to the invention and which has then been recycled to step a) of said process. The term "extrinsic dichloropropanol" is understood to mean dichloropropanol which has not been recycled in the process according to the invention.

The temperature, pressure, reaction time and residence time may have different values in the various reaction zones, such as defined in Applications FR 07/53375 and FR 07/55448 filed in the name of Solvay SA.

The ratio of the 2,3-dichloro-1-propanol content to the 1,3-dichloro-2-propanol content in the dichloropropanol may be different depending on the reaction zone to which the dichloropropanol is supplied. This ratio may be such as described in Applications FR 07/53375 and FR 07/55448 filed in the name of Solvay SA.

The molar ratio of dichloropropanol to the basic compound may be different depending on the reaction zone to which these compounds are supplied. This ratio may be such as described in Applications FR 07/53375 and FR 07/55448 filed in the name of Solvay SA.

The basic compound may be an organic or inorganic basic compound. Organic basic compounds are for example amines, phosphines and ammonium, phosphonium or arsonium hydroxides. Inorganic basic compounds are preferred. The expression "inorganic compounds" is understood to mean compounds which do not contain a carbon-hydrogen bond. The inorganic basic compound may be chosen from alkali and alkaline-earth metal oxides, hydroxides, carbonates, hydrogencarbonates, phosphates, hydrogenphosphates and borates, and mixtures thereof. Alkali and alkaline-earth metal oxides and hydroxides are preferred. Different basic compounds may be used in the various reaction zones where the reaction of step a) is carried out.

Generally, the temperature, reaction time or residence time and the molar ratio of dichloropropanol to the basic compound are higher in the reaction zones where the 2,3-dichloro-1-propanol/1,3-dichloro-2-propanol ratio is higher.

Step a) may be followed by an operation for neutralizing the excess basic compound.

It is possible to combine step a) or part of step a) with step b) in a common device compartmentalized into various reaction and settling zones.

The first fraction separated in step b) may have a composition such as that described for the first fraction separated in step b) of the epichlorohydrin manufacturing process which is the subject of Patent Applications FR 07/53375 and 075/55448 in the name of Solvay SA, of which the content is incorporated here by reference.

The first fraction separated in step b) may contain, besides epichlorohydrin and trichloropropane, other organic compounds such as, for example, halogenated hydrocarbons other than trichloropropane, chloroacetone and methyl glycidyl ether, glycerol, hydroxyacetone, glycidol, acetaldehyde, acrolein, acetone, ethylene oxide, propylene oxide and 2-butanone. These compounds may come from the dichloropropanol manufacturing process and/or be formed during the reaction between dichloropropanol and the basic compound during step a) of the process according to the invention.

The first fraction separated in step b) generally contains at least 100 g of epichlorohydrin/kg of first fraction, preferably at least 200 g/kg, even more preferably at least 300 g/kg, still more preferably at least 400 g/kg, more particularly preferably at least 500 g/kg, even more particularly preferably at least 600 g/kg, still more particularly preferably at least 700 g/kg, most particularly preferably at least 800 g/kg and very most particularly preferably at least 850 g/kg. The epichlorohydrin content of the first fraction separated is generally at most 900 g/kg. The epichlorohydrin content of the first fraction separated depends, for example, on the use of an organic solvent and/or on an incomplete conversion of the mixture of 1,3-dichloro-2-propanol and 2,3-dichloro-1-propanol.

The first fraction separated in step b) generally contains at most 2 g of chloroacetone/kg of first fraction and usually at most 0.3 g/kg, commonly at most 0.1 g/kg, and particularly preferably at most 0.05 g/kg. The chloroacetone content is generally at least 0.005 g/kg.

The first fraction separated in step b) generally contains at most 5 g of acrolein/kg of first fraction, usually at most 0.3 g/kg and commonly at most 0.1 g/kg. The acrolein content is generally at least 0.07 g/kg.

The first fraction separated in step b) generally contains at most 20 g of chloroethers/kg of first fraction, usually at most 5 g/kg, commonly at most 2 g/kg, and particularly preferably at most 1 g/kg. The content of chloroethers is generally at least 0.5 g/kg.

Chloroethers are compounds of which the molecule comprises at least one chlorine atom and at least one oxygen atom, this oxygen atom being bonded to two carbon atoms. Epichlorohydrin is not considered here as a chloroether. These chloroethers preferably contain six carbon atoms. These chloroethers preferably contain two, sometimes three, chlorine atoms. These chloroethers preferably contain two oxygen atoms. These chloroethers are preferably chosen from compounds of crude chemical formula: $C_6H_{10}Cl_2O_2$, $C_6H_{12}Cl_2O$, $C_6H_9Cl_3O_2$, $C_6H_{11}Cl_3O_2$, and mixtures of at least two of them.

The first fraction separated in step b) contains generally at most 10 g of chloroether of crude formula $C_6H_{10}Cl_2O_2$/kg of first fraction, usually at most g/kg, commonly at most 0.5 g/kg, and particularly preferably at most 0.1 g/kg. The content of this chloroether is generally at least 0.05 g/kg.

The first fraction separated in step b) contains generally at most 5 g of chloroether of crude formula $C_6H_{12}Cl_2O$/kg of first fraction, usually at most 2 g/kg, commonly at most 0.5 g/kg, and particularly preferably at most 0.1 g/kg. The content of this chloroether is generally at least 0.05 g/kg.

The first fraction separated in step b) contains generally at most 5 g of chloroether of crude formula $C_6H_9Cl_3O_2$/kg of first fraction, usually at most 2 g/kg, commonly at most 0.5 g/kg, and particularly preferably at most 0.1 g/kg. The content of this chloroether is generally at least 0.02 g/kg.

The first fraction separated in step b) contains generally at most 5 g of chloroether of crude formula $C_6H_{11}Cl_3O_2$/kg of first fraction, usually at most 2 g/kg, commonly at most 1 g/kg, and particularly preferably at most 0.6 g/kg. The content of this chloroether is generally at least 0.5 g/kg.

The first fraction separated in step b) generally contains other organic compounds such as, for example, 1,3-dichloro-2-propanol, 2,3-dichloro-1-propanol and mixtures thereof. The sum of the contents of these dichloropropanols is generally less than or equal to 900 g/kg of first fraction, usually less than or equal to 800 g/kg, commonly less than or equal to 700 g/kg, in many cases less than or equal to 500 g/kg, often less than or equal to 300 g/kg and frequently less than or equal to 200 g/kg. The sum of the contents of these dichloropropanols is generally at least 90 g/kg.

The first fraction separated in step b) generally contains other organic compounds in addition to the epichlorohydrin, chloroacetone, acrolein, chloroethers and dichloropropanols.

The latter may come from the dichloropropanol manufacturing process and/or be formed during the reaction between dichloropropanol and the basic compound during step a) of the process according to the invention. Examples of these compounds are glycerol, 3-chloro-1,2-propanediol, 2-chloro-1,3-propanediol, and mixtures thereof, hydroxyacetone, glycidol, methyl glycidyl ether, 1,2,3-trichloropropane, cis- and trans-1,3-dichloropropenes, 1,3-dichloropropane and 2-chloro-2-propen-1-ol.

The sum of the contents of glycerol, hydroxyacetone and glycidol is generally at most 100 g/kg of first fraction, usually at most 50 g/kg, commonly at most 30 g/kg, in particular at most 10 g/kg and specifically at most 1 g/kg. The sum of these contents is generally at least 0.1 g/kg.

The sum of the contents of 3-chloro-1,2-propanediol and 2-chloro-1,3-propanediol is generally at most 5 g/kg of first fraction, usually at most 3 g/kg, and commonly at most 1 g/kg. This sum is generally at least 0.5 g/kg.

The methyl glycidyl ether content is generally at most 5 g/kg of first fraction, usually at most 3 g/kg, and commonly at most 1 g/kg. This content is generally at least 0.005 g/kg.

The 1,2,3-trichloropropane content is generally at most 10 g/kg of first fraction, usually at most 5 g/kg, commonly at most 3 g/kg and particularly preferably at most 1 g/kg. This content is generally at least 0.0001 g/kg.

The sum of the contents of cis- and trans-1,3-dichloropropenes is generally at most 2 g/kg of first fraction, usually at most 1 g/kg, and commonly at most 0.1 g/kg. This sum is generally at least 0.01 g/kg.

The 1,3-dichloropropane content is generally at most 2 g/kg of first fraction, usually at most 1 g/kg, and commonly at most 0.5 g/kg. This content is generally at least 0.001 g/kg.

The 2-chloro-2-propen-1-ol content is generally at most 2 g/kg of first fraction, usually at most 1 g/kg, and commonly at most 0.5 g/kg. This content is generally at least 0.01 g/kg.

The first fraction separated in step b) generally contains water and inorganic compounds such as the basic compound and the salt.

The water content is generally at most 90 g/kg of first fraction, usually at most 80 g/kg, commonly at most 50 g/kg, often at most 30 g/kg and frequently at most 15 g/kg. The water content is generally at least 1 g/kg of first fraction.

The salt content is generally at most 10 g/kg of first fraction, commonly at most 5 g/kg, usually at most 2 g/kg, often at most 0.1 g/kg and frequently at most 0.015 g/kg. This salt content is generally at least 0.01 g/kg.

The proportion of salt present in the part of the liquid reaction medium from step a) before the settling step b) which is found in the first fraction separated in step b) is generally at most 25%, preferably at most 10% and more preferably at most 5%.

The salts are preferably chosen from alkali or alkaline-earth metal chlorides, sulphates, hydrogensulphates, hydroxides, carbonates, hydrogencarbonates, phosphates, hydrogenphosphates and borates, and mixtures thereof. Alkali and alkaline-earth metal chlorides are preferred. Calcium chloride and sodium chloride are more preferred. Sodium chloride is the most preferred salt.

The first fraction separated in step b) may also contain an acid compound. The acid compound may be chosen from monobasic and polybasic, organic and inorganic acids and mixtures thereof. Polybasic acids may be found in variously protonated forms. Inorganic acids are preferred. The expression "inorganic acid" is understood to mean acids of which the molecule does not contain a carbon-hydrogen bond, such as hydrogen chloride, carbonic acid and its acid salts, sulphuric acid and its acid salts, phosphoric acid and its acid salts and boric acid and its acid salts. Hydrogen chloride is preferred. This acid may be added to the part of the reaction medium from step a) as described in Application FR 07/53375 filed in the name Solvay SA.

The second fraction separated in step b) may have a composition such as that described for the second fraction separated in step b) of the epichlorohydrin manufacturing process which is the subject of Patent Applications FR 07/53375 and 07/55448 in the name of Solvay SA, of which the content is incorporated here by reference.

Among the supplementary treatments from step c), the liquid/liquid extraction, adsorption and distillation operations, alone or in combination, are preferred and the liquid/liquid extraction and distillation operations, alone or in combination, are particularly preferred.

In a first embodiment of step c) of the process for manufacturing the product according to the invention, the treatment from step c) comprises at least one liquid/liquid extraction operation for the first fraction separated in step b).

The extraction operation may be carried out cocurrently or countercurrently.

The cocurrent operation is generally carried out in at least one stirred reactor, followed by a settling tank. The countercurrent operation is generally carried out in at least one extraction column. Various type of reactors, settling tanks and extraction columns may be used, such as those described in "Perry's Chemical Engineers' Handbook", Sixth Edition, section 21, pp. 21, 55 and following".

The extraction solvent may be an organic composition or an aqueous composition.

The extraction solvent is often an aqueous composition. Besides water, the aqueous composition may contain other compounds such as salts and/or basic compounds and/or acid compounds such as defined above and/or dichloropropanol. Frequently, the aqueous composition is essentially composed of water, particularly demineralised water.

After the extraction, a first part containing most of the epichlorohydrin which was contained in the first fraction before the extraction operation, and a second part containing most of the extraction solvent, are separated.

The proportion of epichlorohydrin present in the first fraction separated at the end of the settling step b) of the process according to the invention before the liquid/liquid extraction operation from step c), and which is found in the first part separated in step c), is preferably at least 80%, more preferably at least 90% and even more preferably at least 95%. These proportions are more particularly obtained when the extraction solvent is an aqueous composition.

The epichlorohydrin content of the first part separated in step c) is generally greater than 900 g of epichlorohydrin per kg of first part, preferably greater than or equal to 950 g/kg, more preferably greater than or equal to 990 g/kg and most particularly preferably greater than or equal to 999 g/kg. These contents are more particularly obtained when the extraction solvent is an aqueous composition.

The water content of the first part is generally less than or equal to 150 g of water per kg of first part, usually less than or equal to 100 g/kg, commonly less than or equal to 10 g/kg and particularly less than 1 g/kg.

These contents are more particularly obtained when the extraction solvent is an aqueous composition.

The content of organic extraction solvent from the first part separated in step c) is generally less than or equal to 100 g per kg of first part, usually less than or equal to 50 g/kg and particularly less than or equal to 1 g/kg.

The first part obtained at the end of the liquid/liquid extraction treatment from step c) may constitute the product according to the invention, in particular when the extraction solvent is water. This first part preferably constitutes the product according to the invention.

The first part separated in step c) may be subjected to subsequent treatments such as, for example, distillation, evaporation or stripping operations.

The second part separated in step c) generally contains the basic compound used in step a) of the process and/or the acid compound added before the settling step b) and/or the salt used and/or formed in step a) of the process, in particular when the extraction solvent is an aqueous composition.

The proportion of basic compound present in the first fraction separated at the end of the settling step b) of the process according to the invention before the liquid/liquid extraction operation from step c), and which is found in the second part separated in step c), is generally at least 80%, preferably at least 90% and more preferably at least 95%.

The proportion of salt present in the first fraction separated at the end of the settling step b) of the process according to the invention before the liquid/liquid extraction operation from step c), and which is found in the second part separated in step c), is generally at least 80%, preferably at least 90% and more preferably at least 95%.

These proportions are more particularly obtained when the extraction solvent is an aqueous composition.

The second part separated in step c) may be partially or completely recycled to step a), and/or after step a) and before step b) of the process. That second part is often recycled after step a) and before step b), frequently in the operation for neutralizing the excess basic compound after step a).

The second part separated in step c) may be subjected to a stripping, evaporation or distillation operation that makes it possible to recover the epichlorohydrin dissolved in this part.

In a second embodiment of step c) of the process for manufacturing the product according to the invention, in step c) the first fraction separated in step b) is subjected to a treatment which comprises at least one distillation operation, preferably at least two distillation operations and more preferably at least two distillation operations of which at least one is an operation for drying by azeotropic distillation. This treatment preferably comprises at least two distillation operations and more preferably at least four distillation operations and most particularly preferably at least six distillation operations in addition to the azeotropic distillation drying operation.

The expression "distillation operation" is understood to mean the separation of a mixture into two fractions of different compositions by a series of evaporation and condensation operations interconnected countercurrently and carried out in a specific device or in one part of a specific device. In the case where the separation of a mixture into N fractions of different compositions is carried out in a single physical jacket, it is considered that this corresponds to N−1 distillations.

The operation for drying by azeotropic, preferably heteroazeotropic, distillation with removal of an aqueous phase and of an organic phase, preferably with removal of an aqueous phase, may be carried out before the other distillation operations. The azeotropic distillation drying operation may be carried out after one or more of the other distillation operations.

In this second embodiment, after the treatment from step c), two portions are obtained.

In this second embodiment, the proportion of epichlorohydrin present in the first fraction separated at the end of the settling step b) of the process according to the invention before the treatment from step c), and which is found in the first portion separated in step c), is generally at least 80%, preferably at least 90% and more preferably at least 95%.

In this second embodiment, the proportion of dichloropropanol present in the first fraction separated at the end of the settling step b) of the process according to the invention before the treatment from step c), and which is found in the second portion separated in step c), is generally at least 80%, preferably at least 90% and more preferably at least 95%.

In this second embodiment, the first portion obtained at the end of the distillation operations of the treatment from step c) may constitute the product according to the invention. This first portion preferably constitutes the product according to the invention.

In this second embodiment, the second portion may be partially or completely recycled to step a) of the process to obtain the product according to the invention.

In a third embodiment of step c) of the process for manufacturing the product according to the invention, in step c) the first fraction separated in step b) is subjected to a treatment which comprises at least one adsorption operation and at least one distillation operation, and preferably at least three distillation operations and more preferably at least five distillation operations.

The expression "distillation operation" is understood to mean the separation of a mixture into two fractions having different compositions by a series of evaporation and condensation operations interconnected countercurrently and carried out in a specific device or in one part of a specific device. In the case where the separation of a mixture into N fractions of different compositions is carried out in a single physical jacket, it is considered that this corresponds to N−1 distillations.

In this third embodiment, the adsorption operation may be carried out before the distillation operations. The adsorption operation may be carried out after one or more distillation operations. The object of the adsorption operation is generally to reduce the water content of the fractions treated. The adsorbants generally used are adsorbants such as molecular sieves 3A, 4A and 5A.

In this third embodiment, after the treatment from step c), two cuts are obtained.

In this third embodiment, the proportion of epichlorohydrin present in the first fraction separated at the end of the settling step b) of the process according to the invention before the treatment from step c), and which is found in the first cut separated in step c), is generally at least 80%, preferably at least 90% and more preferably at least 95%.

In this third embodiment, the proportion of dichloropropanol present in the first fraction separated at the end of the settling step b) of the process according to the invention before the treatment from step c), and which is found in the second cut separated in step c), is generally at least 80%, preferably at least 90% and more preferably at least 95%.

In this third embodiment, separated at the end of the treatments described in the second and third embodiments is epichlorohydrin, of which the water content is generally less than 0.5 g of water per kg of epichlorohydrin, usually less than or equal to 0.1 g/kg and commonly less than or equal to 0.05 g/kg. In this epichlorohydrin, the content of organic compounds having a boiling point under a pressure of 1 bar absolute less than or equal to the boiling point of epichlorohydrin is generally less than or equal to 0.3 g of these compounds per kg of epichlorohydrin, usually less than or equal to 0.2 g/kg and commonly less than or equal to 0.1 g/kg. These compounds are, for example, acrolein, methyl glycidyl ether and chloroacetone. In this epichlorohydrin, the content of organic compounds having a boiling point under a pressure of 1 bar absolute greater than or equal to the boiling point of epichlorohydrin is generally less than or equal to 0.7 g of these compounds per kg of epichlorohydrin, usually less than or equal to 0.5 g/kg and commonly less than or equal to 0.3 g/kg. These compounds are, for example, 2-chloro-2-propen-1-ol, dichloropropene, dichloropropane, hydroxyacetone, trichloropropane, glycidol, dichloropropanol, monochloropropanediol, glycerol and chloroethers such as mentioned above.

In this third embodiment, the first cut obtained at the end of the treatment from step c) may constitute the product according to the invention. This first portion preferably constitutes the product according to the invention In a fourth embodiment of step c) of the process for manufacturing the product according to the invention, which is preferred, the first and second embodiments are combined and in one preferred variant, initially, the first fraction separated in step b) is subjected to at least one liquid/liquid extraction operation with an aqueous composition and in which a first part containing most of the epichlorohydrin which was contained in the first fraction before the extraction operation is separated, and this first part is subjected to at least one treatment which comprises at least one operation for drying by azeotropic distillation and at least one distillation operation.

In this fourth embodiment, after the treatment from step c), two cuts are obtained.

In this fourth embodiment, the proportion of epichlorohydrin present in the first fraction separated at the end of the settling step b) of the process according to the invention before the treatment from step c), and which is found in the first cut separated in step c), is generally at least 80%, preferably at least 90% and more preferably at least 95%.

In this fourth embodiment, the proportion of dichloropropanol present in the first fraction separated at the end of the settling step b) of the process according to the invention before the treatment from step c), and which is found in the second cut separated in step c), is generally at least 80%, preferably at least 90% and more preferably at least 95%.

In this fourth embodiment, separated at the end of the treatment from step c) is epichloroydrin, of which the water content is generally less than 0.5 g of water per kg of epichlorohydrin, usually less than or equal to 0.1 g/kg and commonly less than or equal to 0.05 g/kg. In this epichlorohydrin, the content of organic compounds having a boiling point under a pressure of 1 bar absolute less than or equal to the boiling point of epichlorohydrin is generally less than or equal to 0.3 g of these compounds per kg of epichlorohydrin, usually less than or equal to 0.2 g/kg and commonly less than or equal to 0.1 g/kg. In this epichlorohydrin, the content of organic compounds having a boiling point under a pressure of 1 bar absolute greater than or equal to the boiling point of epichlorohydrin is generally less than or equal to 0.7 g of these compounds per kg of epichlorohydrin, usually less than or equal to 0.5 g/kg and commonly less than or equal to 0.3 g/kg.

In this fourth embodiment, the first cut obtained at the end of the treatment from step c) may constitute the product according to the invention. This first cut preferably constitutes the product according to the invention.

BRIEF DESCRIPTION OF THE FIGURES

FIG. 1 shows a first scheme of an installation used for obtaining the product according to the invention.

Figure 1:
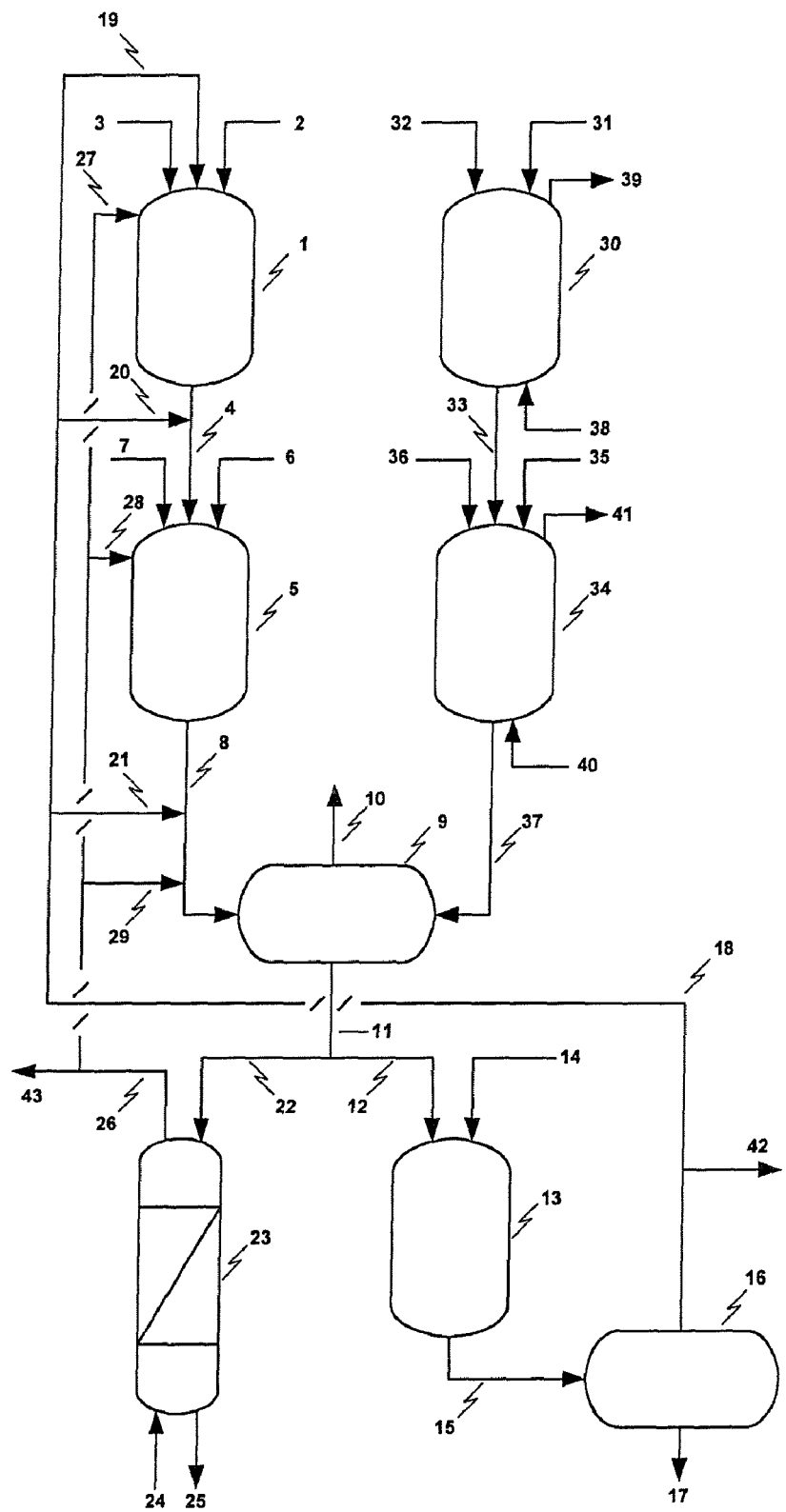
FIG. 1: first scheme of an installation used for obtaining the product according to the invention

In a first variant of this first scheme, a first reactor (1) is supplied with a first stream of dichloropropanol via the line (2) and a first stream of basic compound via the line (3). Drawn off from the reactor (1) via the line (4) is a stream comprising epichlorohydrin, salt, dichloropropanol and basic compound which have not reacted, and a second reactor (5) is supplied with this stream. The reactor (5) is supplied with a second stream of dichloropropanol via the line (6) and with a second stream of basic compound via the line (7). Drawn off from the second reactor (5) via the line (8) is a stream comprising epichlorohydrin and salt, and a first settling tank (9) is supplied with this stream. In the first settling tank (9), a first fraction containing most of the epichlorohydrin contained in the stream (8) and a second fraction containing most of the salt which was contained in the stream (8) are separated. The second fraction is drawn off from the settling tank (9) via the line (10) and the first fraction via the line (11). A first part of the first fraction drawn off from the line (11) supplies a first extractor (13) via the line (12). The first extractor (13) is also supplied with water via the line (14). Vigorous stirring is carried out in the first extractor (13). A stream is drawn off from the extractor (13) via the line (15) and a second settling tank (16) is supplied with this stream. Drawn off from the second settling tank (16) via the line (17) is a third fraction containing most of the epichlorohydrin contained in the stream (15) and a fourth fraction containing water and the salts via the line (18).

In various aspects of this first variant of this first scheme, a portion of the fourth fraction containing water and the salts, drawn off via the line (18), is respectively recycled to the first reactor (1) via the line (19) and/or between the first reactor (1) and the second reactor (5) via the line (20) and/or between the second reactor (5) and the first settling tank (9) via the line (21).

In a second variant of this first scheme, the procedure from the first variant is followed except that the first fraction drawn off from the first settling tank (9) via the line (11) no longer supplies the extractor (13) but supplies an extraction column (23) via the line (22). The extraction column (23) is supplied countercurrently with water via the line (24). Drawn off from the column (23) is a fifth fraction containing most of the epichlorohydrin contained in the stream (22), via the line (25), and a sixth fraction containing water and the salts, via the line (26).

In various aspects of this second variant of this first scheme, a portion of the second fraction containing water and the salts, drawn off via the line (26), is respectively recycled to the first reactor (1) via the line (27) and/or to the second reactor (5) via the line (28) and/or between the second reactor (5) and the first settling tank (9) via the line (29).

In third and fourth variants of this first scheme, the procedure from the first variant or from the second variant respectively is followed, and in addition, a third reactor (30) is supplied with a third stream of dichloropropanol via the line (31) and a third stream of basic compound via the line (32). Drawn off from the reactor (30) via the line (33) is a stream comprising epichlorohydrin, salt, dichloropropanol and basic compound which have not reacted, and a fourth reactor (34) is supplied with this stream. The fourth reactor (34) is supplied with a fourth stream of dichloropropanol via the line (35) and with a fourth stream of basic compound via the line (36). Drawn off from the fourth reactor (34) via the line (37) is a stream comprising epichlorohydrin and salt, and the first settling tank (9) is supplied with this stream.

In various aspects of these third and fourth variants of this embodiment, the third reactor (30) is supplied with steam via the line (38) and drawn off from the third reactor (30), via the line (39), is a stream containing water and epichlorohydrin, and/or the fourth reactor (34) is supplied with steam via the line (40) and drawn off from the fourth reactor (34), via the line (41), is a stream containing water and epichlorohydrin.

In these various variants, part of the streams (18) and/or (26) may supply a purge via the lines (42) and (43) respectively.

Without being bound by any theory, one believes that in the a mixture of dichloropropanol containing 1,3-dichloro-2-propanol and 2,3-dichloro-1-propanol, the 1,3-dichloro-2-propanol isomer is mainly converted into epichlorohydrin in the first reactors (1) and/or (30), while the 2,3-dichloro-1-propanol isomer is mainly converted into epichlorohydrin in the second reactors (5) and/or (34).

Figure 2:
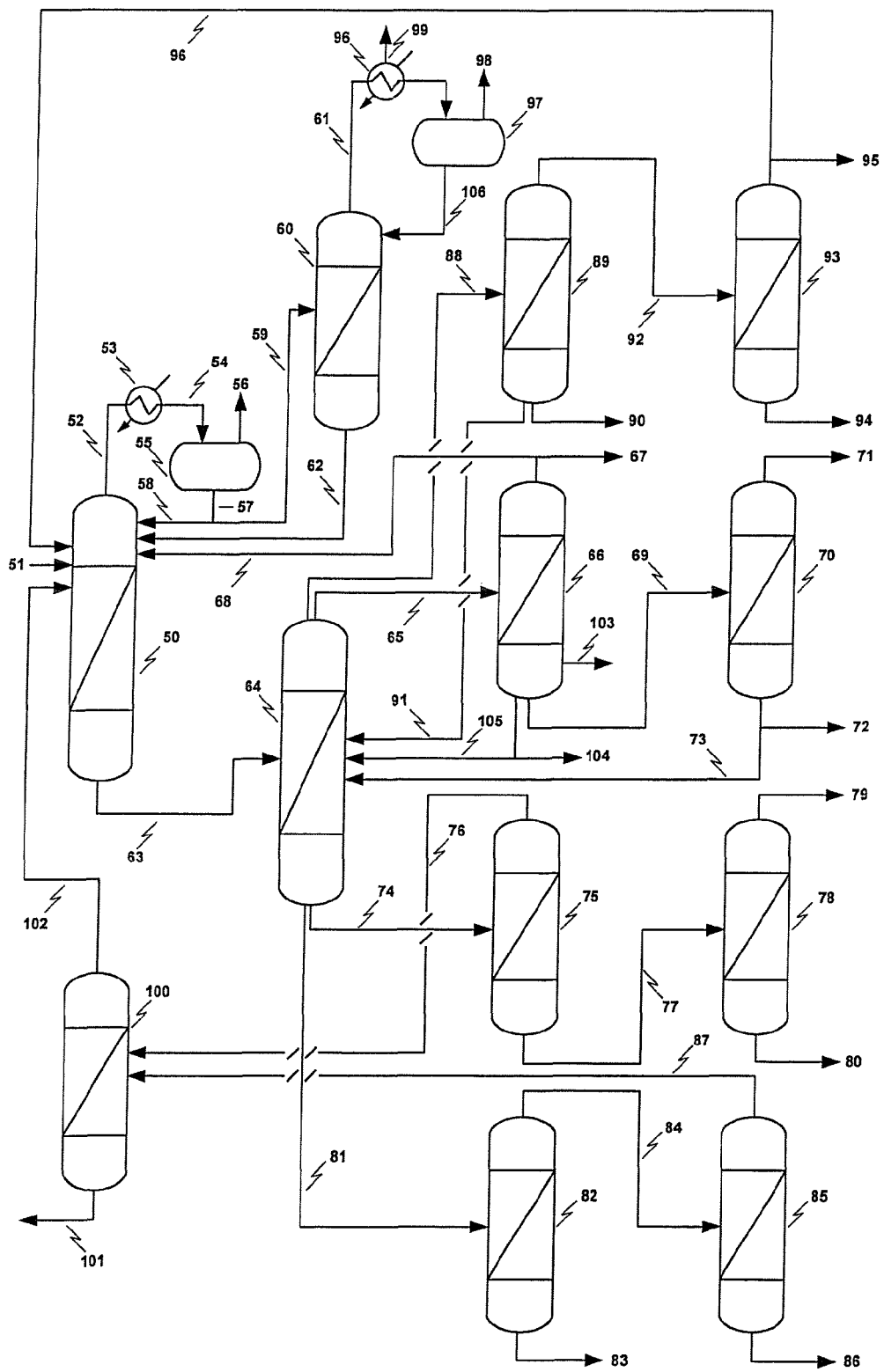
FIG. 2: second scheme of an installation used for obtaining the product according to the invention

FIG. 2 shows a second scheme of an installation used for obtaining the product according to the invention.

In a first variant of this second scheme, an azeotropic drying column (50) is supplied with a stream containing epichlorohydrin via the line (51). This stream comes from one or more lines of the installation described in FIG. 1, i.e. the lines (17), (25) and also the organic fraction of the lines (39) and (41). This stream contains, besides epichlorohydrin, light products, that is to say of which the boiling point under a pressure of 1 bar absolute is below the boiling point of epichlorohydrin, such as acetaldehyde and acrolein, water, heavy products, that is to say of which the boiling point under a pressure of 1 bar absolute is above the boiling point of epichlorohydrin and below the boiling point of dichloropropanol, such as glycidol, 2-chloro-2-propen-1-ol, hydroxyacetone, chloroacetone, 1,3-dichloropropane, 1,3-dichloropropene, 1,2,3-trichloropropane, 2-methyl-2-cyclopenten-1-one, cyclopentanone, 2-chloroethanol and chloropropanol, and super-heavy products, that is to say of which the boiling point under a pressure of 1 bar absolute is above the boiling point of dichloropropanol, such as monochloropropanediol and partially chlorinated and/or esterified glycerol oligomers.

Drawn off from the column (50) via the line (52) is a stream containing water, epichlorohydrin, light products and heavy products that form an azeotrope with water, and a first condenser (53), then a first settling tank (55), are supplied with this stream via the line (54). Drawn off from the first settling tank (55) is a water phase, via the line (56), and epichlorohydrin saturated with water, via the line (57). The water phase can be further sent to a High Temperature Oxidation treatment Unit. A first part of the stream drawn off via the line (57) optionally supplies the distillation column (50) via the line (58). A second part of the stream drawn off via the line (57) supplies a second distillation column (60) via the line (59). Drawn off from the second column (60) via the line (61) is a stream which essentially contains light products and a second condenser (96), then a second settling tank (97), are supplied with this stream via the line (61). Drawn off from the second settling tank (97) is a gas phase containing light products, via the line (99) which can be further sent to a High Temperature Oxidation treatment Unit. Drawn off from the second settling tank (97) is a water phase, via the line (98) which can be further sent to a High Temperature Oxidation treatment Unit. A part of the liquid contained in the settling tank (97), preferably of the organic phase, can be returned to the top of the distillation column (60) via the line (106). Drawn off from the second distillation column (60) via the line (62) is a stream containing mainly epichlorohydrin, and the first distillation column (50) is supplied with this stream.

Drawn off from the column (50) via the line (63) is a stream scrubbed of water, and a third distillation column (64) is supplied with this stream.

Drawn off from the third column (64) via the line (65) is a stream containing epichlorohydrin, light products and heavy products. This stream supplies a fourth distillation column (66) drawn off from which, via the line (67), is a stream that essentially contains light products. One part of this stream may be returned to the first distillation column (50) via the line (68). Drawn off from the fourth distillation column (66) via the line (69) is a stream depleted of light compounds, and a fifth distillation column (70) is supplied with this stream. Drawn off from the fifth distillation column (70) via the line (71) is purified epichlorohydrin and via the line (72) a stream comprising heavy products of which one part may be conveyed to the third distillation column (64) via the line (73).

Drawn off from the third column (64) via the line (74) is a stream comprising epichlorohydrin, heavy products, dichloropropanol and super-heavy products, and a sixth distillation column (75) is supplied with this stream. Drawn off from the sixth distillation column (75) via the line (76) is a stream containing epichlorohydrin and heavy products, and a twelfth distillation column (100) is supplied with this stream and drawn off from the sixth distillation column (75) via the line (77) is a stream containing dichloropropanol and super-heavy products, and a seventh distillation column (78) is supplied with this stream.

Drawn off from the twelfth distillation column (100) via the line (102) is a stream containing epichlorohydrin and that stream is recycled back to the first distillation column (50). Drawn off from the twelfth distillation column (100) via the line (101) is a stream containing heavy products and that stream can be further treated in a High Oxidation Temperature Unit.

Drawn off from the seventh distillation column (78) via the line (79) is a stream of dichloropropanol, and via the line (80) a stream containing super-heavy products. The stream of dichloropropanol collected via the line (79) may be conveyed to one or more of the reactors (1), (5), (30) and (34) of the installation described in FIG. 1. The stream containing super-heavy products can be sent for further treatment a High Temperature Oxidation Unit.

In a second variant of the second scheme, the procedure from the first variant is followed except that the lines and columns (74) to (80) are absent and drawn off from the third column (64) via the line (81) is a stream comprising epichlorohydrin, heavy products, dichloropropanol and super-heavy products, and an eighth distillation column (82) is supplied with this stream. Drawn off from the eighth distillation column (82) via the line (83) is a stream containing super-heavy products, which can be further treated in a High Temperature Oxidation Unit and via the line (84) a stream containing epichlorohydrin, heavy products and dichloropropanol, and a ninth distillation column (85) is supplied with this stream.

Drawn off from the ninth distillation column (85) via the line (86) is a stream of dichloropropanol, and via the line (87) a stream containing epichlorohydrin and heavy products, and the twelfth distillation column 100 is supplied with this stream. The stream of dichloropropanol collected via the line (86) may be conveyed to one or more of the reactors (1), (5), (30) and (34) of the installation described in FIG. 1.

In a third variant of this second scheme, the procedure from the first variant is followed except that the lines and columns (65) to (73) are absent.

Drawn off from the third column (64) via the line (88) is a stream containing epichlorohydrin, light products and heavy products. This stream supplies a tenth distillation column (89) drawn off from which, via the line (90), is a stream that contains heavy products. One part of this stream may be returned to the third distillation column (64) via the line (91). Drawn off from the tenth distillation column (89) via the line (92) is a stream containing epichlorohydrin and light products, and an eleventh distillation column (93) is supplied with this stream. Drawn off from the eleventh distillation column (93) via the line (94) is a stream of purified epichlorohydrin, and via the line (95) a stream containing light compounds. One part of this stream may be conveyed to the first distillation column (50) via the line (96).

In a fourth variant of this second scheme, the procedure from the second variant is followed except that the lines and columns (65) to (73) are absent.

Drawn off from the third column (64) via the line (88) is a stream containing epichlorohydrin, light products and heavy products. This stream supplies a tenth distillation column (89) drawn off from which, via the line (90), is a stream that contains heavy products. One part of this stream may be returned to the third distillation column (64) via the line (91). Drawn off from the tenth distillation column (89) via the line (92) is a stream containing epichlorohydrin and light products, and an eleventh distillation column (93) is supplied with this stream. Drawn off from the eleventh distillation column (93) via the line (94) is a stream of purified epichlorohydrin, and via the line (95) a stream containing light compounds. One part of this stream may be conveyed to the first distillation column (50) via the line (96).

In a fifth variant of this second scheme, the procedure from the first variant is followed except that the lines and columns (69) to (73) are absent.

Drawn off from the third column (66) via the line (103) is a stream containing epichlorohydrin, via line (104) a stream containing heavy products a part of which can be recycled to the third distillation column (64) via line (105).

Figure 3:
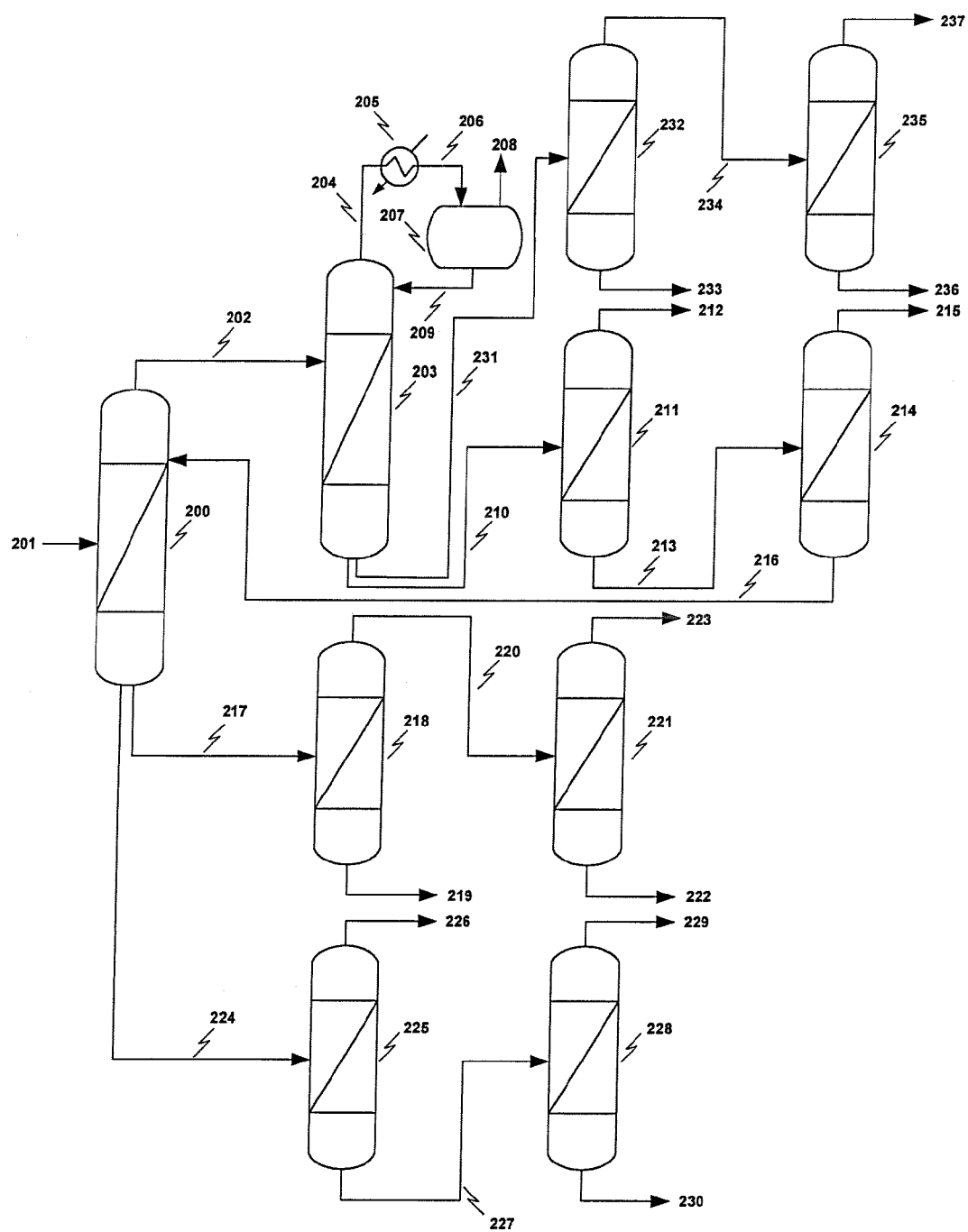
FIG. 3: third scheme of an installation used for obtaining the product according to the invention

FIG. 3 shows a third scheme of an installation used for obtaining the product according to the invention.

In a first variant of this third scheme, a first distillation column (200) is supplied with a stream containing epichlorohydrin via the line (201). This stream comes from one or more lines of the installation described in FIG. 1, i.e. the lines (17) and (25), and the organic fraction of lines (39) and (41). This stream contains, besides epichlorohydrin, light products, that is to say of which the boiling point under a pressure of 1 bar absolute is below the boiling point of epichlorohydrin, such as acetaldehyde and acrolein, water, heavy products, that is to say of which the boiling point under a pressure of 1 bar absolute is above the boiling point of epichlorohydrin and below the boiling point of dichloropropanol, such as glycidol, 2-chloro-2-propen-1-ol, hydroxyacetone, chloroacetone, 1,3-dichloropropane, 1,3-dichloropropene, 1,2,3-trichloropropane, 2-methyl-2-cyclopenten-1-one, cyclopentanone, 2-chloroethanol and chloropropanol, dichloropropanol and super-heavy products, that is to say of which the boiling point under a pressure of 1 bar absolute is above the boiling point of dichloropropanol, such as monochloropropanediol and partially chlorinated and/or esterified glycerol oligomers.

Drawn off from the distillation column (200) via the line (202) is a stream containing epichlorohydrin, water, light compounds and heavy compounds, and an azeotropic drying column (203) is supplied with this stream. Drawn off from the drying column (203) via the line (204) is a stream containing epichlorohydrin and water that is conveyed to a settling tank (207) via a condenser (205) and via the line (206). Drawn off from the settling tank (207) via the line (208) is a stream mostly containing water and, via the line (209) a stream mostly containing epichlorohydrin that is conveyed to the distillation column (200).

Drawn off from the azeotropic drying column (203) via the line (210) is a stream containing epichlorohydrin, light compounds and heavy compounds, and a second distillation column (211) is supplied with this stream. Drawn off from the second distillation column (211) via the line (212) is a stream containing light compounds, and via the line (213) a stream containing epichlorohydrin and heavy compounds, and a third distillation column (214) is supplied with this stream. Drawn off from the column (214) via the line (215) is a stream composed of purified epichlorohydrin, and via the line (216) a stream containing heavy compounds that are recycled to the first distillation column (200).

Drawn off from the first distillation column (200) via the line (217) is a stream containing dichloropropanol, heavy compounds and super-heavy compounds, and a fifth distillation column (218) is supplied with this stream. Drawn off from the column (218) via the line (219) is a stream containing super-heavy products, and via the line (220) a stream containing dichloropropanol and heavy products, and a sixth distillation column (221) is supplied with this stream. Drawn off from the column (221) via the line (222) is a stream mostly containing dichloropropanol, and via the line (223) a stream essentially containing heavy products.

The stream of dichloropropanol collected via the line (222) may be conveyed to one or more of the reactors (1), (5), (30) and (34) of the installation described in FIG. 1.

In a second variant of the third scheme, the procedure from the first variant is followed except that the lines and columns (217) to (223) are absent and drawn off from the first column (200) via the line (224) is a stream comprising heavy products, dichloropropanol and super-heavy products, and a seventh distillation column (225) is supplied with this stream. Drawn off from the seventh distillation column (225) via the line (226) is a stream containing heavy products, and via the line (227) a stream containing super-heavy products and dichloropropanol, and an eighth distillation column (228) is supplied with this stream.

Drawn off from the eighth distillation column (228) via the line (229) is a stream of dichloropropanol, and via the line (230) a stream containing super-heavy products. The stream of dichloropropanol collected via the line (229) may be conveyed to one or more of the reactors (1), (5), (30) and (34) of the installation described in FIG. 1.

In a third variant of the third scheme, the procedure from the first variant is followed except that the lines and columns (210) to (216) are absent.

Drawn off from the drying column (203) via the line (231) is a stream containing epichlorohydrin, light products and heavy products. This stream supplies a ninth distillation column (232) drawn off from which, via the line (233), is a stream that contains heavy products. Drawn off from the ninth distillation column (232) via the line (234) is a stream containing epichlorohydrin and light products, and a tenth distillation column (235) is supplied with this stream. Drawn off from the tenth distillation column (235) via the line (236) is a stream of purified epichlorohydrin, and via the line (237) a stream containing light compounds.

In a fourth variant of the third scheme, the procedure from the second variant is followed except that the lines and columns (210) to (216) are absent.

Drawn off from the drying column (203) via the line (231) is a stream containing epichlorohydrin, light products and heavy products. This stream supplies an eighth distillation column (232) drawn off from which, via the line (233), is a stream that contains heavy products. Drawn off from the eighth distillation column (232) via the line (234) is a stream containing epichlorohydrin and light products, and a ninth distillation column (235) is supplied with this stream. Drawn off from the ninth distillation column (235) via the line (236) is a stream of purified epichlorohydrin, and via the line (237) a stream containing light compounds.

Other variants of the various embodiments can easily be envisaged.

The invention also relates to the use of the epichlorohydrin-based product described above as a reactant in a process for manufacturing epoxy resins, synthetic glycerol, polyamide-epichlorohydrin resins, chemical formulations for water treatment, such as polyacrylamides, polyamines and quaternary ammonium salts, epichlorohydrin elastomers, such as epichlorohydrin homopolymers, epichlorohydrin/ethylene oxide copolymers and epichlorohydrin/ethylene oxide/allyl glycidyl ether terpolymers, glycidyl ethers, such as cresyl glycidyl, butyl, decyl or dodecyl ethers, surfactants, flame retardants, such as phosphorylated flame retardants, resins for the production of water-resistant paper and glycidyl acrylates and methacrylates.

The presence of impurities in epichlorohydrin may prove troublesome in some of these applications for various reasons. Some halogenated hydrocarbons for instance are or are suspected to be carcinogenic, are suspected to have development toxicity, reproductive toxicity, cardiologic toxicity, endocrine toxicity, immunotoxicity and toxicity to the liver, the kidneys, the nerves, the respiratory tract and to the skin. They can remain in the final products and possibly degrade with a concomitant deterioration of the properties of the final products. They can exhibit or degrade in compounds exhibiting some toxicity leading to safety issues especially when the final products are intended to be in contact with food and drink. Moreover, they can accumulate in and contaminate industrial waters such as wastewaters for instance or water containing pulp that is recycled in the pulp and paper industry. In the latter case, their higher concentration can increase contamination of the paper made using the recycled water.

A further goal of the invention is to solve those problems by providing a product containing epichlorohydrin and a reduced level of impurities which can be used in the manufacture of epoxy derivatives, of products which will be used in food and drink applications, of cationization agents, of flame retardants, of products which will be used as detergent ingredients, and of epichlorohydrin elastomers.

The invention is therefore also related to the use of the product according to the invention in the manufacture of epoxy resins or glycidyl esters or glycidyl ethers or glycidyl amides or glycidyl imides or coagulants or wet-strength resins or cationization agents or flame retardants or detergent ingredients or epichlorohydrin elastomers.

1. Epoxy Derivatives 1.1. General

Epoxy derivatives are for example, epoxy resins, glycidyl ethers, glycidyl esters and glycidyl amides and imides. Examples of glycidyl esters are glycidyl acrylate and glycidyl methacrylate.

By epoxy resin, one intend to denote a polymer, the chemical formula of which contains at least one oxirane group, preferably one 2,3-epoxypropyloxy group.

By polymer, one intends to denote molecules with many units joined to each other through chemical covalent bonds, often in a repeating manner, those units being referred as repeat units. The number of repeat units is higher than zero. A polymer contains at least one type of repeat units. When the polymer contains only one type of repeat units, it is called a homopolymer. When the polymer contains more than one type of repeat units, it is called a copolymer. The copolymers can be of the random type, of the alternating type or of the block type, such as described in "Polymer Science Dictionary, M.S.M., Elsevier Applied Science, London and New York 1989, page 86".

Figure 4:
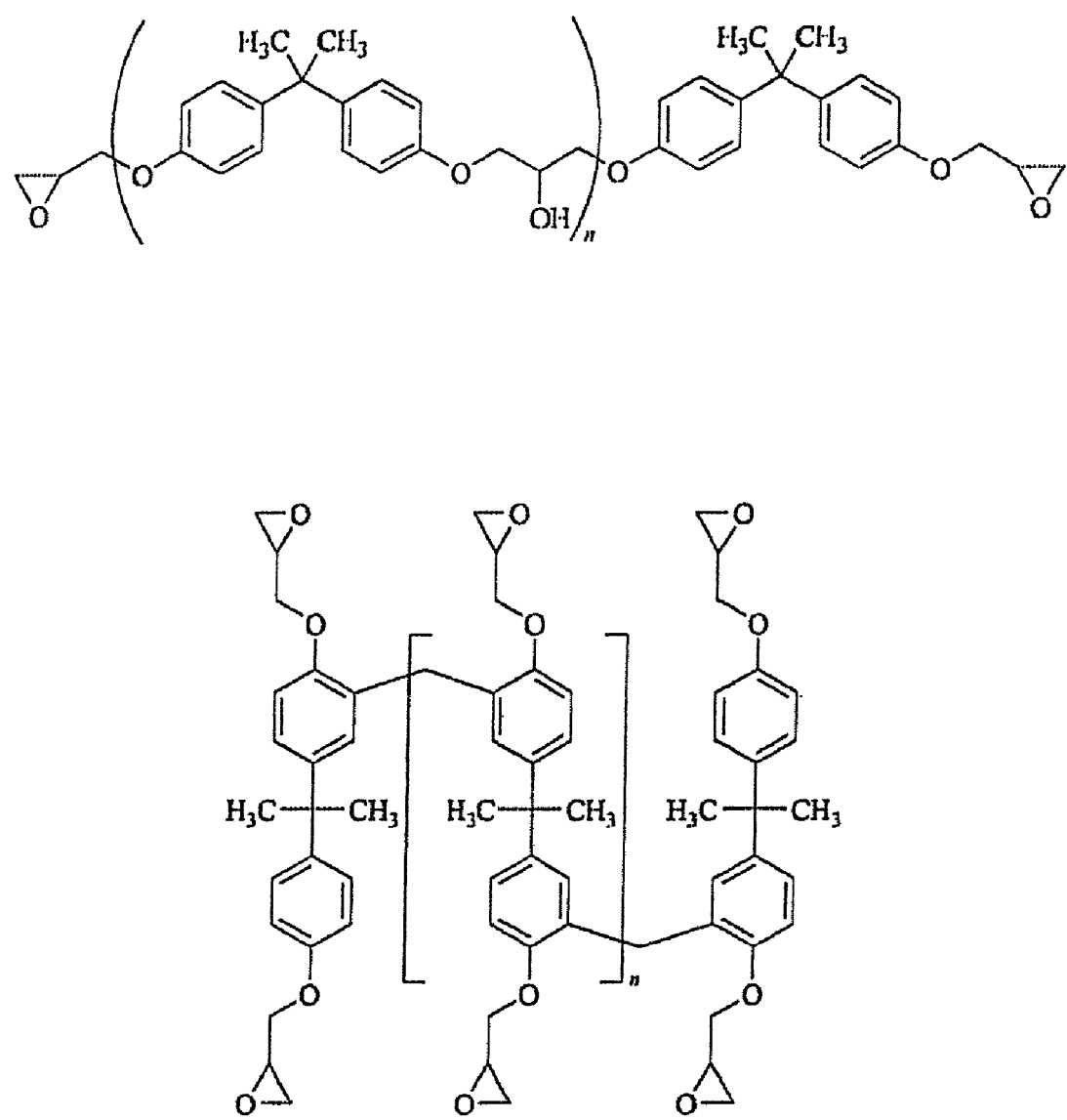
FIG. 4: examples of chemical formula of epoxy resins

Examples of chemical formulas of epoxy resins are presented in FIG. 4, where n is not zero.

By glycidyl ether, one intends to denote an ether, the chemical formula of which contains at least one glycidyl (2,3-epoxypropyl) group and which is not a polymer. Examples of glycidyl ethers are N-butyl glycidyl ether, $C_{12}$-$C_{14}$ aliphatic glycidyl ethers, o-Cresol glycidyl ether, neopentylglycol diglycidyl ether and butanediol diglycidyl ether.

By glycidyl ester, one intends to denote an ester, the chemical formula of which contains at least one glycidyl (2,3-epoxypropyl) group and which is not a polymer. Examples of glycidyl ester are diglycidyl ester of hexahydrophthalic acid, glycidyl ester of neodecanoic acid, glycidyl acrylate and glycidyl methacrylate.

By glycidyl amides and imides, one intends to denote an amide or an imide, the chemical formula of which contains at least one glycidyl (2,3-epoxypropyl) group and which is not a polymer. Examples of glycidyl amide and imide 1,3,5-tris (2,3-epoxypropyl)-1,3,5-perhydrotriazine-2,4,6-trione and 5,5-dimethyl-1,3-bis(2,3-epoxypropyl)-2,4-imidazolidinedione.

1.2. Co-Reactants

When, the product containing epichlorohydrin according to the invention is used in the manufacture of epoxy derivatives, the product containing epichlorohydrin is usually subjected to a reaction with at least one compound containing at least one active hydrogen atom, preferably at least two active hydrogen atoms, followed by dehydrochlorination as described in Ullmann's Encyclopedia of Industrial Chemistry, 5th Edition, 1987, Vol. A9, pp. 547-553).

The compound containing one active hydrogen atom can be selected from mono alcohol, preferably from 1-butanol, a $C_{12}$ to $C_{14}$ primary alcohol or a cresol, and mixtures thereof, mono carboxylic acids, like for instance neodecanoic acid, acrylic acid, methacrylic acid, or mixtures thereof.

The compound containing at least two active hydrogen atoms can be selected from polyols, polyamines, amino alcohols, polyimides and amides, polycarboxylic acids, and mixtures thereof.

The polyols can be aromatic or aliphatic. Aromatic polyols are preferred.

Preferred aliphatic polyols are aliphatic diols, more preferably selected from butanediol, neopentyl glycol, hydrogenated Bisphenol A (4,4'-dihydroxy-2,2-dicyclohexylpropane), and aliphatic triols, preferably glycerol, poly (oxypropylene) glycol, and mixtures thereof.

Aromatic polyols can be selected from polyhydroxy benzenes, polyphenolic compounds, and mixtures thereof.

Poly hydroxybenzenes are preferably selected from dihydroxy benzenes, trihydroxy benzene, and mixtures thereof. Dihydroxy benzenes are more preferably selected from 1,2-, 1,3-, 1,4-dihydroxy benzenes and mixture thereof.

Trihydroxy benzene is preferably 1,3,5-trihydroxy benzene.

Polyphenolic compounds are generally compounds the molecule of which contains at least one aromatic hydroxyl group.

Figure 5:
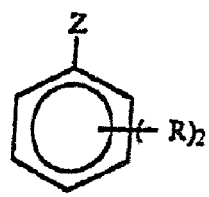
FIG. 5: examples of chemical formula of compounds having at least one aromatic hydroxyl group
Figure 5:
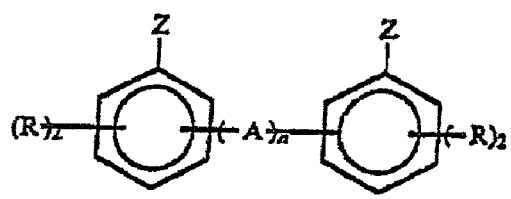
Figure 5:
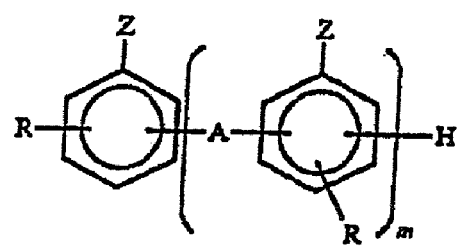
Figure 5:
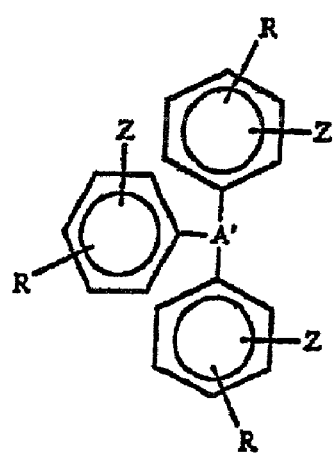
Figure 5:
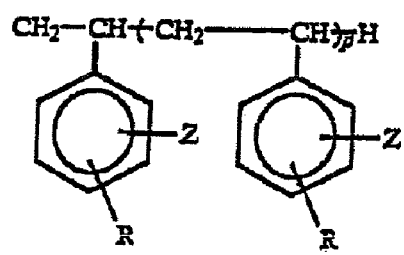

Suitable compounds having at least one aromatic hydroxyl group which can be employed herein are such as described in U.S. Pat. No. 4,499,255, the content of which is incorporated herein by reference and include, for example, phenols, bisphenols, novolac resins, polyvinyl phenols, the corresponding amine compounds and the like, such as those represented by the formulas I to V of FIG. 5 wherein, each A is independently a divalent hydrocarbon group having from 1 to about 12, preferably from 1 to about 6 carbon atoms, —O—, —S—, —S—S—, —(S=O)$_2$—, —(S=O)— or —(C=O)—, A' is a trivalent hydrocarbon group having from 1 to about 12, preferably from 1 to about 6, carbon atoms; each R is independently hydrogen, a hydrocarbyl group having from 1 to about 10, preferably from 1 to about 4, carbon atoms, a halogen atom, preferably chlorine or bromine or a hydroxyl group or an amino group; each Z is independently —OH or NH2; p has a value of from about 1 to about 100, preferably from about 2 to about 50; m has a value from about 1.00 to about 6 and n has a value of zero or 1.

Figure 6:
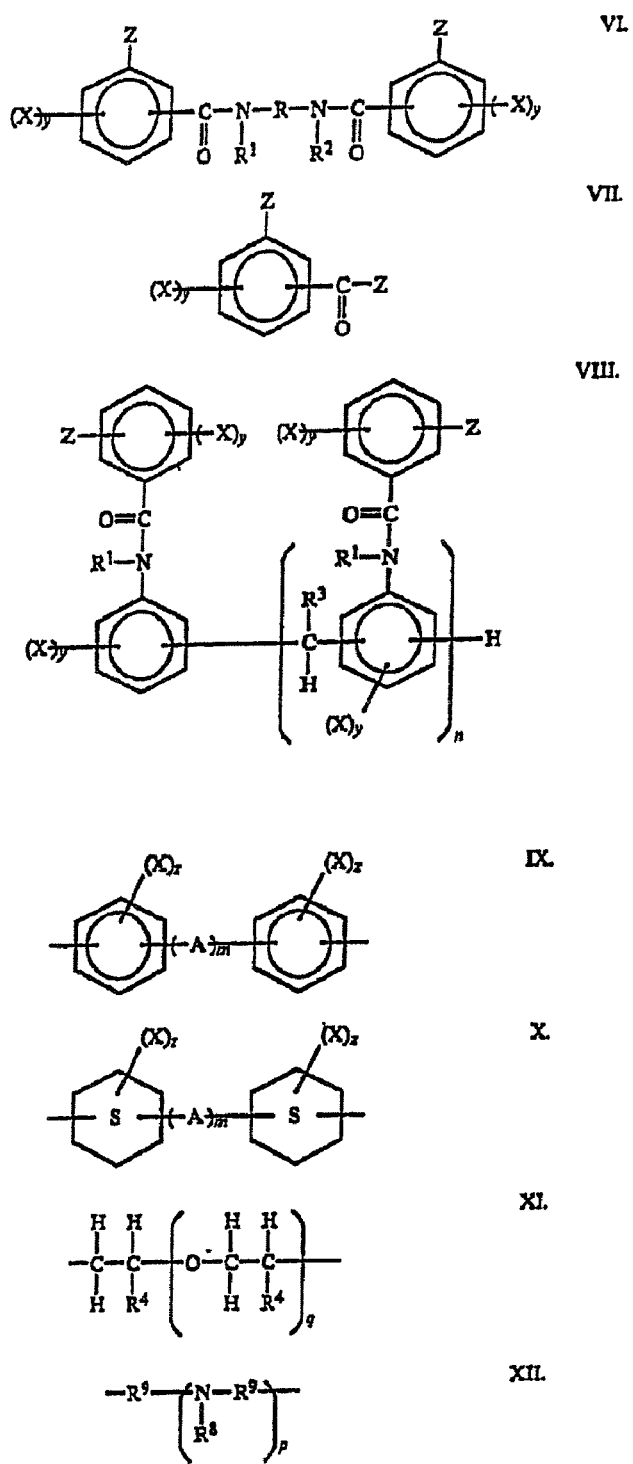
FIG. 6: examples of chemical formula of compounds having at least one aromatic hydroxyl or aromatic amine group per molecule

Also suitable as compounds having at least one aromatic hydroxyl or aromatic amine group per molecule are those represented by the formulas VI to VIII of FIG. 6, wherein each R is a divalent hydrocarbyl group having from 1 to about 18, preferably from about 2 to about 12 and most preferably from about 2 to about 6 carbon atoms, a group represented by the formulas IX, X, XI or XII of FIG. 6, or R can combine with $R^1$ so as to form a stable heterocyclic ring with the nitrogen atoms; each A is independently a divalent hydrocarbyl group having from 1 to about 10, preferably from 1 to about four carbon atoms, —O—, —S—, —S—S—, —(S=O)$_2$—, —(S=O)— or —(C=O)—, each $R^1$ is independently hydrogen, a 2,3-epoxypropyl group, a 2-alkyl-2,3-epoxypropyl group, a monovalent hydrocarbyl group or a hydroxyl substituted monovalent hydrocarbyl group, said hydrocarbyl groups having from 1 to about 9 carbon atoms, said alkyl having from 1 to about 4, preferably 1 to about 3 carbon atoms; each $R^2$ is independently hydrogen or an alkyl group having from 1 to about 4, preferably 1 to about 3 carbon atoms; each $R^3$ is independently hydrogen or an alkyl group having from 1 to about 4 carbon atoms; each $R^4$ is independently hydrogen, a hydrocarbyl or halogen substituted hydrocarbyl group having from 1 to about 9, preferably from 1 to about 2 carbon atoms; each $R^8$ is independently selected from the group represented by formula XIV or the same groups as $R^1$ except that $R^8$ cannot be a hydrogen; each $R^9$ is independently a divalent hydrocarbyl group having from 2 to about 4, preferably 2 carbon atoms; each Z is independently —OH or —NH2; each X is independently hydrogen, chlorine, bromine or a hydrocarbyl or a hydrocarbyloxy group having from 1 to about 9, preferably 1 to about 6 carbon atoms; each m independently has a value of zero or 1; n has an average value of from about 0.01 to about 6, preferably 0.1 to about 4; p has an average value of from 1 to about 10, preferably from 1 to about 3; q has an average value of at least 1, preferably from 1 to about 150, most preferably from 1 to about 100 and usually from 1 to about 10 and each y and z independently has a value of 1 or 2.

Figure 7:
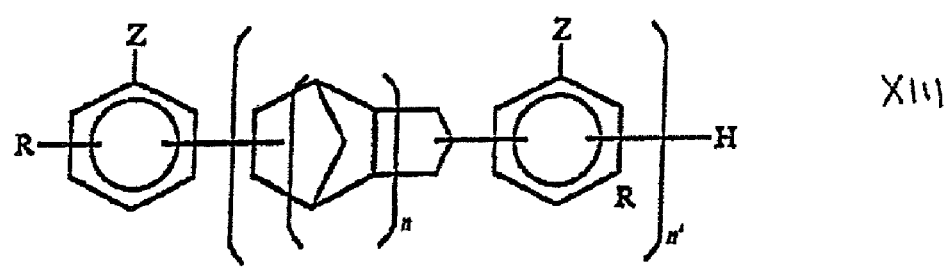
FIG. 7: examples of chemical formula of polycyclopentadiene polyphenols or aromatic polyamines

Also suitable are polycyclopentadiene polyphenols or aromatic polyamines represented by the formula XIII of FIG. 7, wherein Z is —OH or —NH2 and n has a value from 1 to about 5; n' has a value of from about 1 to about 10, preferably from 3 to about 6; each R is independently hydrogen, a hydrocarbyl group having from 1 to about 10, preferably from 1 to about 4 carbon atoms, a halogen atom, preferably chlorine or bromine or a hydroxyl group or an amino group.

Suitable such polycyclopentadiene polyphenols and methods for their preparation can be found in U.S. Pat. No. 4,390,680 issued to Donald L. Nelson on Jun. 28, 1983 which is incorporated herein by reference. The polycyclopentadiene aromatic polyamines can be prepared in a similar manner by substituting an aromatic amine for the phenolic compound.

Also suitable are compounds containing both at least one aromatic hydroxyl group and at least one aromatic amine group such as, for example, hydroxy aniline, aminoxylenol and the like.

The polyphenolic compound is preferably selected from Bisphenol A (4,4'-dihydroxy-2,2-diphenylpropane, 4,4'-isopropylidenediphenol), tetrabromo Bisphenol A (4,4'-isopropylidenebis(2,6-dibromophenol)), Bisphenol AF (4,4'-[2,2,2-trifluoro-1-(trifluoromethyl)ethylidene]bisphenol)= hexafluorobisphenol A (4,4'-dihydroxy-2,2-diphenyl-1,1,1,3,3,3-hexafluoropropane), 1,1,2,2-tetra(p-hydroxyphenyl) ethane, hexafluorobisphenol A, tetramethylbisphenol (4,4'-dihydroxy-3,3',5,5'-tetramethyl bisphenol), 1,5-dihydroxynaphthalene, 1,1',7,7'-tetrahydroxy-dinaphthyl methane, 4,4'-dihydroxy-a-methylstilbene, a condensation product of Bisphenol A with formaldehyde (Bisphenol A novolac), a condensation product of phenol with formaldehyde, preferably Bisphenol F (mixture of o,o', o,p' and p,p' isomers of dihydroxy diphenylmethane), a condensation product of cresol with formaldehyde (mixtures of o,o', o,p' and p,p' isomers of methyl hydroxy diphenylmethane), an alkylation product of phenol and dicyclopentadiene (2,5-bis [(hydroxy phenyl)octahydro-4,7-methano-5H-indene), a condensation product of phenol and glyoxal (tetrakis(4-hydroxyphenyl)ethane), a condensation product of phenol and a hydroxybenzaldehyde (e.g., tris(4-hydroxyphenyl)methane), 1,1,3-tris-(p-hydroxyphenyl)-propane, and mixtures thereof.

The polyamines can be aliphatic or aromatic. Aromatic diamines are preferred, like for instance 4,4'-diamino diphenyl methane.

The amino alcohol can be aliphatic or aromatic. Aromatic amino alcohol are preferred like for instance, p-aminophenol.

The imides and amides can be aliphatic or aromatic. Heterocyclic imides and amides are preferred, like for instance 1,3,5-triazinetriol and imidazolidine-2,4-dione.

Polycarboxylic acids can be aliphatic or aromatic. An example of dimeric fatty acid is linoleic dimer acid. The polycarboxylic acid is preferably an aromatic dicarboxylic acid like for instance hexahydrophthalic acid.

1.3. Processes for Making Epoxy Derivatives

The process for making epoxy resins, glycidyl ethers and glycidyl esters generally involve a reaction of the product containing epichlorohydrin and the compound containing at least one active hydrogen atom, followed by dehydrochlorination with a basic agent The process for making epoxy resin usually involves two steps: the preparation of an uncured epoxy resin followed by a curing step.

1.3.1. Uncured ER

The reaction between the product containing epichlorohydrin and the compound containing at least one, preferably two active hydrogen atoms can be carried out by any process known in the art like for instance the Caustic Coupling Process and the phase-transfer catalyst process, for making Liquid Epoxy Resins (LER), the Taffy and the Advancement or Fusion process for making Solid Epoxy Resins (SER).

Caustic Coupling Process

In the caustic process, caustic is used as a catalyst for the nucleophilic ring-opening (coupling reaction) of the epoxide group on the primary carbon atom of epichlorohydrin by the phenolic hydroxyl group and as a dehydrochlorinating agent for conversion of the chlorohydrin to the epoxide group. Caustic (NaOH) can however be substituted by any basic compound.

The epichlorohydrin and the compound with active hydrogen atom, preferably an aromatic hydroxyl or aromatic amine compound, are employed in a molar ratio of from about 2:1 to about 10:1, preferably from about 2:1 to about 6:1, respectively.

The basic compound may be an organic or inorganic basic compound. Organic basic compounds are for example amines, phosphines and ammonium, phosphonium or arsonium hydroxides. Inorganic basic compounds are preferred. The expression "inorganic compounds" is understood to mean compounds which do not contain a carbon-hydrogen bond. The inorganic basic compound may be chosen from alkali and alkaline-earth metal oxides, hydroxides, carbonates, hydrogencarbonates, phosphates, hydrogenphosphates and borates, and mixtures thereof. Alkali and alkaline-earth metal oxides and hydroxides are preferred. Preferred alkali metal hydroxides which can be employed herein include, for example, sodium hydroxide, potassium hydroxide, lithium hydroxide or mixtures thereof. Sodium hydroxide is especially preferred.

In the process according to the invention, the basic compound may be in the form of a liquid, an essentially anhydrous solid, a hydrated solid, an aqueous and/or organic solution or an aqueous and/or organic suspension. The basic compound is preferably in the form of an essentially anhydrous solid, a hydrated solid, an aqueous solution or an aqueous suspension. It is preferred to use a solution or a suspension, preferably a solution of the basic compound, preferably sodium hydroxide, in water.

The content of the basic agent in the solution or suspension is generally higher than or equal to 5% by weight, preferably higher than or equal to 10% by weight, preferably higher than or equal to 20% by weight, and most preferably higher than or equal to 30% by weight. That content is usually lower than or equal to 70% by weight, preferably lower than or equal to 60% by weight, preferably lower than or equal to 50% by weight, and most preferably lower than or equal to 40% by weight.

The alkali metal hydroxide is preferably employed as an aqueous solution, usually at a concentration of from about 20 to about 50, preferably from about 40 to about 50 percent by weight.

The amount of basic compound, preferably alkali metal hydroxide, which is employed in the process of the present invention is from about 0.80 mole to about 1.2 mole of basic agent, preferably from about 0.90 mole to 1.0 mole per each, preferably aromatic, hydroxyl group and, preferably aromatic, amine hydrogen.

The basic agent, epichlorohydrin and the compound containing active hydrogen atom can be mixed in any order. It is preferred to add the basic compound to a mixture of the two other reactants. The basic agent, preferably, alkali metal hydroxide can be added either continuously or incrementally, but never is all of the alkali metal hydroxide added in one increment.

The reaction can be carried out in a solvent. Suitable solvents which can be employed include any solvent which does not react with any component in the reaction mixture. Preferably such solvent is partially or wholly miscible with water, forms a codistillate with the epichlorohydrin and water and the distillate has a boiling point below that of the lowest boiling component of the reaction mixture at the pressure employed. Suitable such solvents include primary and secondary alcohols such as, for example, 1-methoxy-2-hydroxy propane, 1-butoxy-2-hydroxy ethane, cyclohexanol. The secondary alcohols are preferred.

When a solvent is used, the amount of solvent which is employed will depend on the particular solvent and the compound containing active hydrogen atom being employed. The solvent generally ranges from about 5 to about 50 weight percent, preferably from about 10 to about 40 weight percent based on the total weight of reactants.

The pressure can be equal to 1 bar absolute, lower than 1 bar absolute or higher than 1 bar absolute. When a solvent is used, suitable pressures which can be employed are those which will provide the codistillate with a boiling point of from about 45° C. to about 80° C., preferably from about 55° C. to about 70° C.

The temperature of the reaction is usually greater than or equal to 25° C., preferably greater than or equal to 50° C., more preferably greater than or equal to 90° C., and most preferably greater than or equal to 95° C. The temperature of the reaction is usually lower than or equal to 200° C., preferably lower than or equal to 150° C., more preferably lower than or equal to 125° C., and most preferably lower than or equal to 120° C.

The reaction is usually conducted for a length of time such that the quantity of groups containing active hydrogen atom remaining in the reaction mixture is not greater than about 0.5, preferably not greater than about 0.2 percent by weight. That time is usually greater than or equal to 0.5 h, frequently greater than or equal to 1.0 h, often greater than or equal to 2.0 h, and most particularly greater than or equal to 3.0 h. The time of reaction is usually lower than or equal to 20 h, often lower than or equal to 10 h, frequently lower than or equal to 5 h, and most particularly lower than or equal to 4 h.

Upon completion of the reaction, the resultant epoxy resin is finished in any of the methods normally employed. The excess epichlorohydrin is usually removed by distillation and the salt removed by filtration, centrifugation and/or water washing.

The epichlorohydrin distillation is generally carried out in two steps. The first step is carried out generally at atmospheric pressure (1 bar absolute), at a temperature usually greater than or equal to 100° C., preferably greater than or equal to 120° C., more preferably greater than or equal to 130° C., and most preferably greater than or equal to 145° C. and usually lower than or equal to 200° C., preferably lower than or equal to 180° C., more preferably lower than or equal to 175° C., and most preferably lower than or equal to 155° C. The second step is carried out usually at a subatmospheric pressure, usually lower than or equal to 0.1 bar absolute, preferably lower than or equal to 0.01 bar, more preferably lower than or equal to 0.005 bar, and most preferably lower than or equal to 0.002 bar, at a temperature usually greater than or equal to 150° C., preferably greater than or equal to 170° C., more preferably greater than or equal to 190° C., and most preferably greater than or equal to 195° C. and usually lower than or equal to 300° C., preferably lower than or equal to 250° C., more preferably lower than or equal to 220° C., and most preferably lower than or equal to 215° C.

The salt which is formed can be separated from the crude product through addition of a solvent, e.g. toluene, followed by filtration and distillation to remove the solvent.

Phase-Transfer Catalytic Process

Alternatively, in the Phase-Transfer Catalyst Process, the coupling reaction and dehydrochlorination can be performed separately by using phase-transfer coupling catalysts, such as quaternary ammonium salts, which are not strong enough bases to promote dehydrochlorination. Once the coupling reaction is completed, caustic is added to carry out the dehydrochlorination step. Via this method, higher yields of for example the monomeric diglycidyl ether of Bisphenol A (DGEBA) (>90%) are readily available.

Batch methods and preferably continuous or semi continuous processes can be used.

Taffy Process

The Taffy method is used to prepare higher molecular weight solid resins. It is directly from epichlorohydrin, the compound containing active hydrogen atoms, and a stoichiometric amount of NaOH. This process is very similar to the caustic coupling process used to prepare liquid epoxy resins. Lower epichlorohydrin to compound containing active hydrogen atoms ratios are used to promote formation of high molecular weight resins. Upon completion of the polymerization, the mixture consists of an alkaline brine solution and a water-resin emulsion. The product is recovered by separating the phases, washing the resin with water, and removing the water under vacuum.

The epichlorohydrin and the compound with active hydrogen atom, preferably an aromatic hydroxyl or aromatic amine compound, are employed in a molar ratio of from about 1:1 to about 2:1, preferably from about 1.3:1 to about 1.8:1, respectively.

The alkali metal hydroxide is preferably employed as an aqueous solution, usually at a concentration of from about 1 to about 20, preferably from about 5 to about 15 percent by weight.

The amount of basic compound, preferably alkali metal hydroxide, which is employed in the process of the present invention is from about 0.05 mole to about 2 mole of basic agent, preferably from about 0.1 mole to 0.5 mole per each, preferably aromatic, hydroxyl group and, preferably aromatic, amine hydrogen.

The temperature of the reaction is usually greater than or equal to 25° C., preferably greater than or equal to 50° C., more preferably greater than or equal to 90° C., and most preferably greater than or equal to 95° C. The temperature of the reaction is usually lower than or equal to 200° C., preferably lower than or equal to 150° C., more preferably lower than or equal to 125° C., and most preferably lower than or equal to 120° C.

The time of reaction is usually greater than or equal to 0.1 h, frequently greater than or equal to 0.5 h, often greater than or equal to 1.0 h, and most particularly greater than or equal to 1.5 h. The time of reaction is usually lower than or equal to 20 h, often lower than or equal to 10 h, frequently lower than or equal to 5 h, and most particularly lower than or equal to 4 h.

The basic agent, epichlorohydrin and the compound containing active hydrogen atom can be mixed in any order. It is preferred to add epichlorohydrin to a mixture of the two other reactants.

The reaction is usually carried out under vigorous agitation.

At the end of the reaction, the mixture separates into two layers. The heavier aqueous layer is drawn off and the molten, taffy-like product is washed with hot water until the wash water is neutral. The taffy-like product is dried at a temperature generally higher than or equal to 100° C., preferably higher than or equal to 120° C.

Alternatively, epichlorohydrin and water can be removed by distillation at temperatures up to 180° C. under vacuum. The crude resin/salt mixture can then be dissolved in a secondary solvent to facilitate water washing and salt removal. The secondary solvent can then be removed via vacuum distillation to obtain the product.

The advancement or fusion process is an alternative method for making solid epoxy resin and is based on the chain-extension reaction of liquid epoxy resin (for example, crude DGEBA) with bisphenol A.

1.3.2. Curing Agents

The curing of Epoxy Resins can be carried out using classical curing agents. The cure can be done with coreactive curing agents, or it can be catalytic or photoinitiated cationic.

The coreactive curing agents can be selected from amine functional curing agents, carboxylic functional polyester and anhydride curing agents, phenolic-terminated curing agents, melamine-, urea-, and phenol-formaldehyde resins, mercaptans (polysulfides and polymercaptans) curing agents, cyclic amidines curing agents, isocyanate curing agents and cyanate ester curing agents The amine functional curing agents can be primary and secondary amines, polyamides, amidoamines and dicyandiamide.

The amines can be aliphatic, cycloaliphatic, aromatic amines or arylyl amines.

The aliphatic amines can be selected from liquid aliphatic polyamines, such as polyethylene polyamines, hexamethylene diamine, polyether amines (polyglycol-based polyamines), ketimines (reaction products of ketones and primary aliphatic amines), mannich base adducts (reaction products of amine, phenol and formaldehyde), polyetheramines (reaction product of polyols derived from ethylene or propylene oxide with amines) and mixtures thereof.

The cycloaliphatic amines can be selected from isophorone diamine, bis(4-amino-cyclohexyl)methane, 1,2-diamino-cyclohexane, trihexylmethylene diamines, metaxylylenediamine, and mixtures thereof.

The aromatic amines can be selected from meta-phenylenediamine, methylene dianiline, alkyl (tetraethyl-)-substituted methylene dianiline, 4,4'-diaminodiphenylmethane, 4,4'-diamino diphenyl sulfone, diethylenetoluenediamine The arylyl amines can be selected from meta xylylenediamine, 1,3-bis(aminomethyl cyclohexane).

The amine can be more specifically selected from diethylenetriamine, triethylenetetramine, Poly(oxypropylene diamine), poly(oxypropylene triamine), poly(glycol amine), N-aminoethylpiperazine, isophorone diamine, 1,2-diaminocyclohexane, bis(4-aminocyclohexyl)methane, 4,4-diaminodiphenylmethane, 4,4-diaminodiphenyl sulfone, m-phenylenediamine, diethyltoluenediamine, meta-xylene diamine, 1,3-bis(aminomethyl cyclohexane, and mixtures thereof.

The polyamides can be obtained by reaction of dimerized and trimerized vegetable oil fatty acids (9,12 and 9,11-linoleic acids) with polyamines (diethylene triamine) or from polyamines and phenolic-containing carboxylic acids (phenalkamines).

The amidoamines can be obtained by reaction of mono functional acid like tall-oil fatty acid with a polyamine such diethylenediamine.

The carboxylic functional polyester can be obtained by reaction of terphthalic acid, trimellitic anhydride and neopentyl alcohol The acid anhydrides can be phthalic anhydride, tetrahydrophthalic anhydride, methyltetrahydrophthalic anhydride, methyl hexahydrophthalic anhydride, hexahydrophthalic anhydride, nadic methyl anhydride or methyl himic anhydride, benzophenonetetracarboxylic dianhydride, tetrachlorophthalic anhydride, and mixtures thereof.

The phenolic-terminated curing agents are products that can be obtained by reaction of phenol, creseol or bisphenol a with formaldehydes.

The mercaptans (polysulfides and polymercaptans) curing agents generally contain terminal thiols.

The cyclic amidines curing agents can be for instance 2-phenyl imidazolidine.

The cyanate ester curing agents can be for instance bisphenol a dicyante ester.

The catalytic cure can be carried out with Lewis bases or Lewis acids.

The Lewis bases are for instance tertiary amine, like 2-diethylaminomethylphenol, 2,4,6-tris(dimethylaminomethyl) phenol and imidazoles such as 2-methylimidazole and 2-phenylimidazole, cyclic amidines like 2-phenylimidazoline, substituted ureas like 3-phenyl-1,1-dimethylurea and quaternary ammonium salt like tetralkyl- and alkyl-triphenyl phosphonium salts.

The Lewis acid can be slected from boron trilhalides, preferably boron trifluoride.

The Photoinitiated Cationic Cure can be carried out with photoinitiators like aryldiazonium salts, diaryldiazonium salts, diaryldiionium salts and onium salts of Group VIa elements, such as triarylsulfonium salt, dialkylphenacyl sulfonium salts.

1.4 Uses of Epoxy Resins

The epoxy resins can be used in coating applications and in structural applications. The coating applications can be in the fields of marine and industrial maintenance (corrosion-resistant coatings for ships, shipping containers, offshore oil rigs and platforms, transportation infrastructures such as bridges, rail car coatings, coatings for industrial storage tanks, and primers for light industrial and agricultural equipment), metal container (aluminum and steel food and beverage cans) and coil coatings (metal can ends, can bodies, building products, appliance panels, transportation, and metal furniture applications), automotive coatings (primer surface coatings) and inks and resists. Coating can be done using various technologies like low solids solventborne coating, high solid solventborne coating, solvent-free coating, waterborne coating, powder coating and radiation-curable coating.

The structural applications can be in the field of structural composites (fiber reinforcing materials based on glass, boron, graphite and aromatic polyaramides), of civil engineering, flooring (floor paints, self-leveling floors, trowelable floors, and pebble-finished floors) and construction, of electrical laminates, of electrical laminates (printed wiring boards and printed circuit boards), of other electrical and electronic applications, like casting, potting, encapsulation (switchgear components, transformers, insulators, high voltage cable accessories, and similar devices) and transfer molding (encapsulation of electronic components such as semiconductor chips, passive devices, and integrated circuits), of adhesives (cohesion between similar and dissimilar materials such as metals, glass, ceramics, wood, cloth, and many types of plastics) and of tooling (prototypes, master models, molds and other parts for aerospace, automotive, foundry, boat building, and various industrial molded items).

1.5 Uses of Glycidyl Ethers and Esters

These products are used for applications such as coatings, adhesives and reactive diluents.

1.6 Uses of Glycidyl Amides and Imides

These products are used for applications such as outdoor powder coatings with polyesters, or in applications in which a non-yellowing epoxy resin is desirable.

2. Products for Food-Drink Applications—Coagulants 2.1. General

The product containing epichlorohydrin according to the invention can be used for the manufacture of products that will be used in applications where they will come in contact with food and drink, more specifically for the manufacture of synthetic organic coagulants.

Coagulation refers to the reduction or elimination of electrostatic repulsion forces between particles via addition of certain coagulants, and in technical terms, the first phase of floc formation after chemical mixing and destabilization, but before dosing of flocculants.

Coagulants are generally polymers with a high cationic charge density to neutralize negative charges of colloids and initiate the formation of flocs. They generally exhibit a relatively low molecular weight in order to permit a good diffusion of the charges around the particles and a low viscosity to allow a good distribution of the polymer in the effluents.

By coagulant, one intends to denote a polymer, comprising at least one repeat unit containing at least one 2-hydroxypropyldialkylammonium group.

Figure 8:
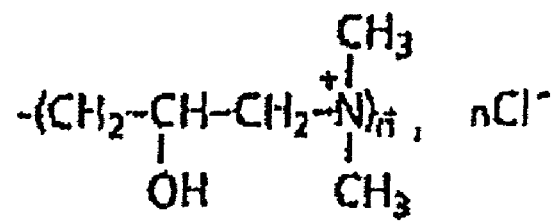
FIG. 8: example of chemical formula of a coagulant molecule

An example of a coagulant molecule is presented in FIG. 8.

2.2. Co-Reactants

In the application according to the invention, the product containing epichlorohydrin is usually subjected to a reaction with ammonia, an amine, a polyaminoamide or a polyimine.

The amine can be a mono-, a di- or a polyamine. The amine can be aliphatic, alicyclic or aromatic, saturated or unsaturated, linear or substituted. The amine has preferably at least one, more preferably at least two primary amino hydrogens.

The amine can be represented by the general formula:

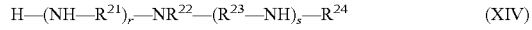

$$H—(NH—R^{21})_r—NR^{22}—(R^{23}—NH)_s—R^{24} \qquad (XIV)$$

wherein $R^{22}$ and $R^{24}$ can be equal, except when equal to H, or different and can independently be selected from H, alkyl or alkenyl radical, linear, branched or carbocyclic, having from 1 to 30 carbon atoms, $R^{21}$ and $R^{23}$ can be equal or different, preferably equal, divalent aliphatic radical aromatic radicals having from 2 to 12 carbon atoms, each of r and s is an integer of from 0 to 6, r plus s equals 0 to 6.

Amines include lower alkyl and lower alkenyl primary monoamines, such as methylamine, ethylamine, isopropylamine, tertbutylamine, mixed amylamines, n-octylamine, branched-chain nonylamine, secondary amines such as dimethylamine, ethylmethylamine, diethylamine, propylmethylamine, propylethylamine, dipropylamine, dibutylamine, propylbutylamine, ethylbutylamine, methylbutylamine, pentylethylamine, pentylethylamine, and pentylpropylamine, tertiary amines, as well as alkylenediamines, triamines and polyamines, with or without an alkenyl or alkyl substituent bonded to nitrogen, such as ethylenediamine, propylenediamine, butylenediamine, pentylenediamine, hexylenediamine, octylenediamine, dodecylenediamine, cyclohexylenediamine, diethylenetriamine, dipropylenetriamine, dipentylenetriamine, triethylene tetramine, tributylenetetramine, trihexylenetetramine, tetraethylenepentamine, tetrapropylenepentamine, pentahexylenehexamine, pentapropylenehexamine, N-ethyl-1,2-ethylenediamine, N-(2-propenyl)-1,3-propanediamine, N-hexyl-1,4-butanediamine, N-2-ethylhexyl-1,3-propanediamine, N-(5-octenyl)-1,6-hexanediamine, N-butyltriethylenetriamine, N-hexyltripropylenetetramine, N-nonyltetrabutylenepentamine and N-(oleyl)-heaxethyleneheptamine, N-alkyl-1,3-diaminopropane, butane and hexane, where the radical alkyl can be hexyl, heptyl, octyl, nonyl, decyl, undecyl, dodecyl, tridecyl, tetradecyl, pentadecyl, hexadecyl, heptadecyl, nonadecyl, eicosyl, heneicosyl, docosyl, tricosyl, and tetracosyl.

The monoamine is preferably a secondary amine, more preferably dimethylamine.

The diamine is more preferably selected from 1,2-diaminoethane, 1,2-diaminopropane, 1,3-diaminopropane, a N-substituted diaminopropane, more preferably, 1-amino-3-dimethylaminopropane, 1-amino-3-diethylaminopropane, 1-amino-3-cyclohexylaminopropane, N,N,N',N'-tetramethyl-1,3-propanediamine, 1,3-diaminobutane, 1,5-diaminopentane, 1,8-diaminooctane, 1,10-diaminodecane, 1,12-diaminododecane, 2-(diethylamino)ethylamine, 1-diethylamino-4-aminopentane, 3-aminomethyl-3,5,5-trimethylcyclohexylamine and N,N,N',N'-tetramethyl-1,6-hexanediamine.

Polyaminoamides are generally obtained from polyamide, preferably polyacrylamide, formaldehyde and an amine, preferably a secondary amine. Poly[N-(dialkylaminoalkyl) acrylamide] is particularly preferred.

Polyimines are usually obtained by ring opening polymerization of alkylene imine, preferably ethylene imine.

2.3. Processes

The reaction between the product containing epichlorohydrin and the compound containing at least one, preferably two primary amino hydrogens can be carried out by any process known in the art.

The reaction is generally carried out in the liquid phase, possibly in the presence of a solvent. The solvent may be selected from water, an organic solvent, preferably miscible with water, or mixtures thereof. Water is preferred. Monoalcohols, like methanol, ethanol, n-propanol, isopropanol and butanol are preferred organic solvents When a solvent is used, the ammonia or amine content in the solvent-ammonia or amine mixture is usually higher than or equal to 5% by weight (% wt), preferably higher than or equal to 10 wt %, more preferably higher than or equal to 20 wt % and most preferably higher than or equal to 45 wt %. That content is usually lower than or equal to 90 wt %, preferably lower than or equal to 75 wt %, more preferably lower than or equal to 60 wt %, and most preferably lower than or equal to 55 wt %.

The molar ratio between epichlorohydrin and ammonia or amine is generally higher than or equal to 0.1, preferably higher than or equal to 0.5, more preferably higher than or equal to 0.75 and most preferably higher than or equal to 1. That ratio is usually lower than or equal to 10, preferably lower than or equal to 5, more preferably lower than or equal to 3, and most preferably lower than or equal to 2.

The temperature at which the reaction is carried out is generally higher than or equal to 10° C., preferably higher than or equal to 25° C., more preferably higher than or equal to 50° C. and most preferably higher than or equal to 60° C. That temperature is usually lower than or equal to 120° C., preferably lower than or equal to 110° C., more preferably lower than or equal to 100° C., and most preferably lower than or equal to 90° C.

The pressure at which the reaction is carried out is generally higher than or equal to 0.1 bar absolute, preferably higher than or equal to 0.2 bar, more preferably higher than or equal to 0.5 bar and most preferably higher than or equal to 1 bar. That pressure is usually lower than or equal to 20 bar, preferably lower than or equal to 10 bar, more preferably lower than or equal to 5 bar, and most preferably lower than or equal to 2 bar.

The duration of the reaction is generally higher than or equal to 10 min absolute, preferably higher than or equal to 20 min, more preferably higher than or equal to 30 min and most preferably higher than or equal to 60 min. That duration is usually lower than or equal to 10 h, preferably lower than or equal to 5 h, more preferably lower than or equal to 3 h, and most preferably lower than or equal to 2 h.

The manufacturing procedure usually involves the dissolution of the amines or ammonia in the solvent, followed by a slow addition of the epichlorohydrin, itself possibly dissolved in a solvent, possibly cooling in order to keep the temperature of the reaction between 10 and 50° C., often between 25 and 40° C., then after the epichlorohydrin addition is complete, raising the temperature to between 60 and 90° C.

The reaction product can be recovered as an aqueous solution, or a solid after further treatments, e.g. distillation of the solvents under vacuum, treatment of the solution with an acid or a base.

These reactions lead to the formation of the monomer. For example a reaction between epichlorohydrin and dimethylamine produces the epichlorohydrin dimethylamine monomer. This is then homopolymerized to the corresponding quaternary ammonium compound which is a low molecular weight cationic polymer used as a coagulant. Such polymerization usually takes place under alkaline conditions.

The monomer can also be copolymerized with acrylamide to produce higher molecular weight polymers also used for water treatment.

2.4. Products Characteristics

The obtained polymers usually exhibit a molecular weight that is higher than or equal to 5 000, often higher than or equal to 10 000, and frequently higher than or equal to 50 000. That molecular weight is usually lower than or equal to 500 000, often lower than or equal to 400 000, and frequently lower than or equal to 300 000. They can be obtained as aqueous solution containing from 40 to 50% by weight of polymers and exhibiting viscosities from 40 to 11 000 centipoise.

2.5. Uses

These polymers can be used for treatment of raw water for conversion to drinking water, for recycling paper of water in Pulp & Paper Industry, for paint detackification, for breaking oil emulsions, for oil and grease removal, and for sludge dewatering. They can also be used for sugar refining.

3. Products for Food-Drink Applications—Wet-Strength Resins 3.1. General

The product containing epichlorohydrin according to the invention can be used for the manufacture of products that will be used in applications where they will come in contact with food and drink, more specifically for the manufacture of wet-strength resins.

By wet-strength resin one intends to denote a polyaminoamide polymer, the chemical formula of which contains at least one group selected from 2,3-epoxypropylamine, 2,3-epoxypropylammonium, 3-chloro-2-hydroxypropylamine, 3-chloro-2-hydroxypropylammonium, 3-hydroxyazetidinium, and any combination of at least two of them.

Figure 9:
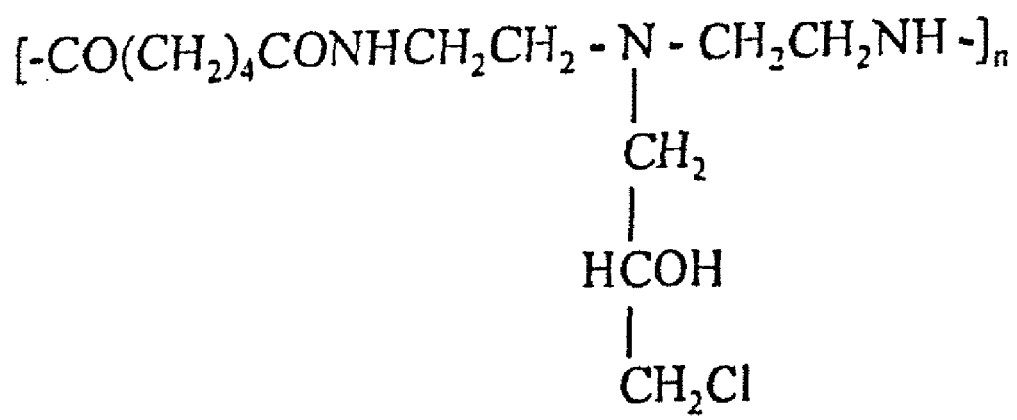
FIG. 9: example of chemical formula of wet-strength resin polymers
Figure 9:
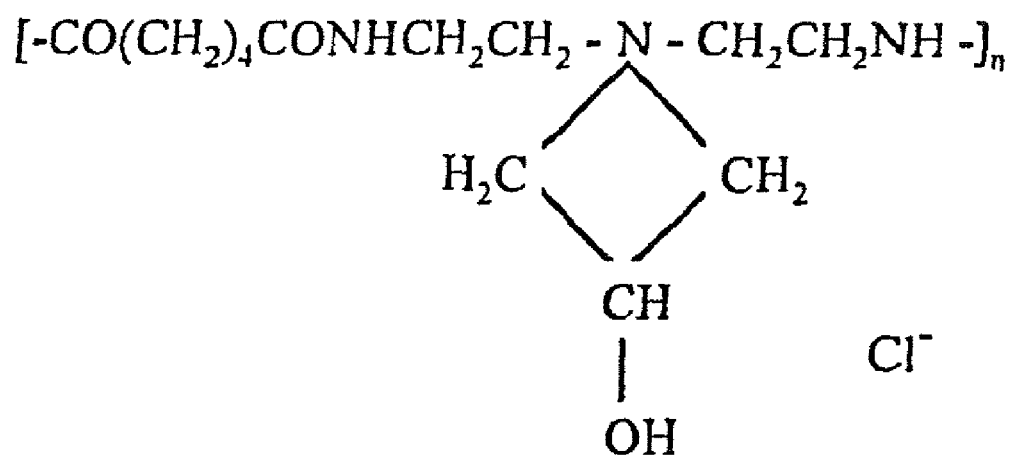

Examples of chemical formulas of such a polymer are presented in FIG. 9.

3.2. Co-Reactants

In the application according to the invention, the product containing epichlorohydrin is usually subjected to a reaction with a polyamine or a polyamide.

The polyamine and the reactions conditions are as described above for the manufacture of coagulants.

The polyamide is usually obtained by reacting an amine, preferably a polyalkylene polyamine (in this case the polyamide is generally referred as a polyaminamide) and a dicarboxylic acid, preferably a saturated aliphatic dicarboxylic acid, as described in U.S. Pat. No. 865,727, the content of which is incorporated herein by reference. The polyamide may be represented by the general formula

$$-NH-(R^{21})_r-NR^{22}-(R^{23}-NH)_s-COR^{24}CO- \quad (XV)$$

where $R^{21}$, $R^{22}$, $R^{23}$, r and s are as described above, and $R^{24}$ is the divalent hydrocarbon radical of the dibasic carboxylic acid, preferably selected from phenylene, naphthalene, methylene, ethylene, propylene, butylenes, pentylene, hexylene, octylene and nonylene.

Preferably, the polyamide may be represented by the general formula

$$-NH(C_tH_{2t}HN)_x-COR^{24}CO- \quad (XVI)$$

wherein t and x are each 2 or more and wherein
the —NH($C_tH_{2t}$HN)$_x$— group is derived from the polyamines described above, preferably containing from 2 to 8 alkylene groups, more preferably from diethylenetriamine, triethylenetetramine, tetraethylenepentamine, dipropylenetriamine and N-bis(aminopropyl)methylamine
the —COR$^{24}$CO— group is derived from dibasic carboxylic acid containing from 2 to 12 carbon atoms, preferably selected from phenylene, naphthalene, methylene, ethylene, propylene, butylenes, pentylene, hexylene, octylene and nonylene. The acid is more preferably selected from malonic, succinic, glutaric, adipic, diglycolic, sebacic or azelaic acid, and mixtures thereof.

3.3. Processes

The reaction between the polyamide and epichlorohydrin is usually carried out at a temperature generally higher than or equal to 45° C. That temperature is usually lower than or equal to 100° C., preferably lower than or equal to 70° C. The temperature at which the reaction is conducted is preferably selected in two stages. In the first stage, the reaction mixture is maintained at 30° C.-50° C., preferably 39°-41° C. Reaction time for the first stage is preferably about 90-190 minutes to form an intermediate polyaminochlorohydrin. Then the reaction temperature is gradually increased to 55°-75° C. such that the intermediate polyaminochlorohydrin is controllably cross-linked to a determined level. The second stage is continued until the viscosity of the reaction mixture reaches the desired level (preferably level M to N on a Gardner-Holdt viscosity scale).

Broadly speaking, the reaction can be carried out neat or in an aqueous solution of up to 57 wt % in water. Preferably, the polyaminoamide is reacted with epichlorohydrin in an aqueous solution of 52-57 wt % in water that is, a solution of 43-48 wt % total solids (the weight percentage of the solution that is solubilized solid material), more preferably about 45 wt % total solids. Reaction time varies depending on the temperature, with lower temperatures taking longer times. The typical composition of these resins is 12.5% (10-40% solids). However, due to the cost of transporting water, companies have tried to produce resin solutions of higher concentration. It appears that at least one of the main issues making such concentrated solutions difficult to prepare is their high content of dichloropropanol so the level of this impurity is exceeded in the final application.

Reaction is preferably carried out until all, or substantially all of the available amine groups on the polyaminoamide are reacted with epichlorohydrin. Generally, reaction times vary between about 1 and 19 hours, preferably between 3 and 6 hours. Because the reaction is exothermic, the epichlorohydrin is added slowly over time to the polyaminoamide to allow for more effective heat transfer from the reaction medium. Heat transfer from the reaction medium can be accomplished according to known procedures, such as immersing the reaction vessel in a refrigerated environment, e.g., an ice bath, or passing refrigerated coils inside the reaction vessel.

The reaction is usually carried out in aqueous solution to moderate the reaction. The pH adjustment is usually not necessary but since the pH decreases during the reaction, it may be desirable in some cases, to add alkali to combine with at least some of the acid formed.

In the reaction, it is preferred to use sufficient epichlorohydrin to convert the entire secondary amine group to tertiary amine groups. The molar ratio between epichlorhydrin and the secondary amine groups is usually higher than or equal to 0.1, preferably higher than or equal to 0.5, and more preferably higher than or equal to 1. That molar ratio is usually lower than or equal to 10, preferably lower than or equal to 5, and more preferably lower than or equal to 2.

The reaction between the polyamide and epichlorohydrin can also be carried in the presence of a quaternizing agent, the conditions of reaction and the reactants, except for the inclusion of the quaternizing agent, being essentially the same as described above. In a preferred procedure, the epichlorhydrin is first added to an aqueous solution of the polyamide at a temperature from 45 to 55° C. The reaction mixture is then heated to a temperature from about 60 to 100° C., and preferably from about 50 to 80° C., depending on the rate of the polymerization desired. After a suitable time at that temperature, i.e., 0 to 100 min, a time after which the epoxy group of the epichlorohydrin have reacted with the secondary amine groups of the polyamide, the quaternizing agent is added and the reaction mixture heated, preferably at a temperature from 60° C. to 80° C. The pH of the reaction mixture is then reduced to 4, preferably between 2 and 3 with any suitable acid such as sulphuric, hydrochloric formic and the like. The amount of quaternizing agent should be sufficient to convert from 25% to 75%, preferably 50% of the tertiary amine group to quaternary group.

The quaternizing agent may be any compound capable of quaternizing a tertiary nitrogen atom in an aqueous medium. In general these compounds are characterized by having as a principal part of their structure an alkyl group or substituted alkyl group which is readily available for alkylation under the conditions herein described. These include the lower alkyl esters of mineral acids such the halides, sulfates and phosphates, and substituted alkyl halides. Illustrative of these compounds which may be used are dimethyl, diethyl and dipropylsulfate, methyl chloride, methyl iodide, methyl bromide, ethyl bromide, propyl bromide, the mono-, di- or trimethyl, ethyl and propyl phosphates, 1,3-dichloropropanol-2 and 1-chloroglycerol. Certain aromatic compounds may also be used like benzyl chloride and methyl p-toluene sulfonate.

The above products resulting from the reaction between epichlorohydrin and the polyamide can be further cross polymerized by treatment with a sodium carbonate or sodium hydroxide solution at a pH between 10.5 and 12.

3.4. Uses

These resins are used in papers that will get wet such as paper towels, tea bags, coffee filters, milk cartons, meat wrapping, wallpaper. They can also be used in the production of high fructose corn syrup and to prevent wool from shrinking

4. Cationization Agents

4.1. General

The product containing epichlorohydrin according to the invention can be used for the manufacture of cationization agents.

By cationization agent, one intends to denote a quaternary ammonium salt, the chemical formula of which contains at least one group selected from 2,3-epoxypropyl, 3-chloro-2-hydroxypropyl, and their combination, and which is not a polymer.

Cationization agents are often quaternary ammonium salt containing a glycidyl or a 3-chloro-2-hydroxypropyl group attached to the nitrogen atom. The cationization agent can be isolated as solids or as solution in water or in organic solvents.

Examples of cationization agents are 3-chloro-2-hydroxypropyl trimethylammonium chloride and glycidyl trimethyl ammonium chloride.

4.2. Co-Reactants

In the application according to the invention, the product containing epichlorohydrin is usually subjected to a reaction with an amine, an amine salt, or a mixture thereof.

The amine is preferably a tertiary amine and the amine salt is preferably a tertiary amine salt.

The tertiary amine salt is for instance a salt obtained by treating an amine with an acid, preferably an inorganic acid, like for instance hydrochloric or sulphuric acid.

The tertiary amine may be represented by the formula

$$R^{31}—N(R^{32})—R''\qquad (XVII)$$

wherein $R^{31}$, $R^{32}$ and $R^{33}$ can be selected from the group consisting of alkyl, cycloalkyl, alkene, aryl, aralkyl, alkylaryl, two of them being possibly joined to form a ring and containing from 1 to 25 carbon atoms. The group attached to the nitrogen can be linear or substituted, saturated or unsaturated.

If all three of $R^{31}$, $R^{32}$ and $R^{33}$ are the same, they preferably each should not contain more than 4 carbon atoms. If all three of $R^{31}$, $R^{32}$ and $R^{33}$ are not the same and if $R^{33}$ contains up to 18 carbon atoms, the $R^{31}$ and $R^{32}$ should preferably be of the group consisting of methyl and ethyl. If $R^{31}$ and $R^{32}$ are joined to form a ring, then $R^{33}$ should preferably be from the group consisting of methyl and ethyl.

Examples of suitable tertiary amines are triethylamine, N-methyl and N-ethylmorpholine, N-ethyl and N-methylpiperidine and methyl diallylamine, trimethylamine, dimethylbenzylamine, dimethyldodecylamine, dimethylstearylamines, dimethylaniline, tri-npropylamine.

It is particularly preferred that the tertiary amine possess two methyl groups attached to the nitrogen, like for instance, trimethylamine, dimethylbenzylamine, dimethyldodecylamine, dimethylstearylamine, and dimethylaniline.

The amine salt is preferably a salt obtained by reaction between the above described amines with hydrochloric or sulfuric acid, preferably with hydrochloric acid.

4.3. Processes

The reaction between the product containing epichlorohydrin and the amine or the amine salt can be carried out by any process known in the art such as those described in U.S. Pat. No. 2,876,217 the content of which is incorporated herein by reference.

The reaction is generally carried out in the liquid phase, possibly in the presence of a solvent. The solvent may be selected from water, an organic solvent e.g. an alcohol, a ketone, an ester or an aliphatic hydrocarbon, preferably miscible with water, or mixtures thereof. Water is preferred. Monoalcohols, like methanol, ethanol, n-propanol, isopropanol and butanol are preferred organic solvents, with methanol being particularly preferred.

The content of epichlorohydrin in the solvent is usually higher than or equal to 0.1 mol/l, often higher than or equal to 0.5 mol/l, frequently higher than or equal to 1.0 mol/l, particularly higher than or equal to 2 mol/l, specifically higher than or equal to 5 mol/l and sometimes higher than or equal to 10 mol/l. That epichlorohydrin content is usually lower than 20 mol/l.

The content of amine or amine salt in the solvent is usually higher than or equal to 0.1 mol/l, often higher than or equal to 0.5 mol/l, frequently higher than or equal to 1.0 mol/l, particularly higher than or equal to 2 mol/l, specifically higher than or equal to 5 mol/l and sometimes higher than or equal to 10 mol/l. That amine or amine salt content is usually lower than 20 mol/l.

The molar epichlorohydrine/amine or amine salt ratio is usually higher than or equal to 0.1, preferably higher than or equal to 0.5, more preferably higher than or equal to 1 and most preferably higher than or equal to 1.2. That ratio is usually lower than or equal to 10, more preferably lower than or equal to 5 and lost preferably lower than or equal to 2.

The temperature at which the reaction is carried out is generally higher than or equal to 0° C., preferably higher than or equal to 10° C., more preferably higher than or equal to 25° C. and most preferably higher than or equal to 40° C. That temperature is usually lower than or equal to 100° C., preferably lower than or equal to 80° C., more preferably lower than or equal to 60° C., and most preferably lower than or equal to 50° C.

The pressure at which the reaction is carried out is generally higher than or equal to 0.1 bar absolute, preferably higher than or equal to 0.2 bar, more preferably higher than or equal to 0.5 bar and most preferably higher than or equal to 1 bar. That pressure is usually lower than or equal to 20 bar, preferably lower than or equal to 10 bar, more preferably lower than or equal to 5 bar, and most preferably lower than or equal to 2 bar.

The duration of the reaction is generally higher than or equal to 10 min absolute, preferably higher than or equal to 20 min, more preferably higher than or equal to 30 min and most preferably higher than or equal to 60 min. That duration is usually lower than or equal to 72 h, preferably lower than or equal to 60 h, more preferably lower than or equal to 48 h, and most preferably lower than or equal to 10 h.

When an amine salt or a mixture of an amine and of an amine salt is used, the pH of the reaction is usually at least 5, and preferably at least 6. That pH is usually at most 9, preferably at most 8.

In a first embodiment, the manufacturing procedure usually involves the mixing of the amine, epichlorohydrin and water, followed by heating at the desired temperature for the desired duration. The aqueous solution is further concentrated by vacuum distillation. The temperature of distillation is as described for the reaction. The distillation pressure is usually lower than or equal to 100 mbar absolute, preferably lower than or equal to 75 mbar and most preferably lower than or equal to 50 mbar. That pressure is usually higher than or equal to 1 mbar absolute.

In a second embodiment, an aqueous solution of the amine is first added to hydrochloric acid until a pH between 8 and 9 is obtained. Epichlorohydrin is further added to the resulting solution and the mixture stirred at the desired temperature for the desired duration. The solution is further distilled under vacuum to the solid 3-chloro-2-trialkylammonium chloride. The solid can be used as such or further cyclized into the glycidyl derivative by reaction with sodium hydroxide in aqueous solution.

In a third embodiment, an amine hydrochloride is dispersed in water. Sufficient sodium hydroxide is added to raise de pH from around 3 to around 8. Epichlorohydrin is further added to the resulting solution and the mixture stirred at the desired temperature for the desired duration. The chlorohydrin group is further cyclized into the glycidyl derivative by reaction with sodium hydroxide in aqueous solution.

In the various embodiments, the aqueous solution obtained at the end of the reaction can be further concentrated by vacuum evaporation or distillation at a temperature of less than 50° C. in order to obtain a slurry containing at least 90% by weight of solid, preferably at least 95% by weight. A water miscible alcohol having 3 to 4 carbon atoms, such as isopropanol, n-propanol, and tert-butanol, preferably isopropanol, is added to the slurry, such as to obtain an alcohol content from 10 to 70% wt, preferably from 25 to 50% wt, based on the total weight of the resulting alcohol-water slurry. The precipitated solids are then recovered by filtration or by other means suitable for removing solids from liquid. The solid may optionally be washed with additional volumes of alcohol or another non-solvent and/or dried to remove any trace of water and alcohol.

The reaction product can be recovered as an aqueous solution, or a solid after further treatments, e.g. distillation of the solvents under vacuum, treatment of the solution with an acid or a base.

4.4. Uses

Cationization agents are mainly used in the cationization of starch to be utilized by the paper industry for processing of high quality paper grades or for cationization of textile for dye fixing.

5. Flame Retardants 5.1. General

The product containing epichlorohydrin according to the invention can be used for the manufacture of flame retardants additives.

The product containing epichlorohydrin according to the invention can preferably be used for the manufacture of phosphorus containing flame retardants additives.

By phosphorus containing flame retardants, one intends to denote a compound, the chemical formula of which contains at least one phosphorus atom and at least one group selected from 2,3-epoxypropyloxy, 3-chloro-2-hydroxypropyl, and the combination of at least two of them.

Figure 10:
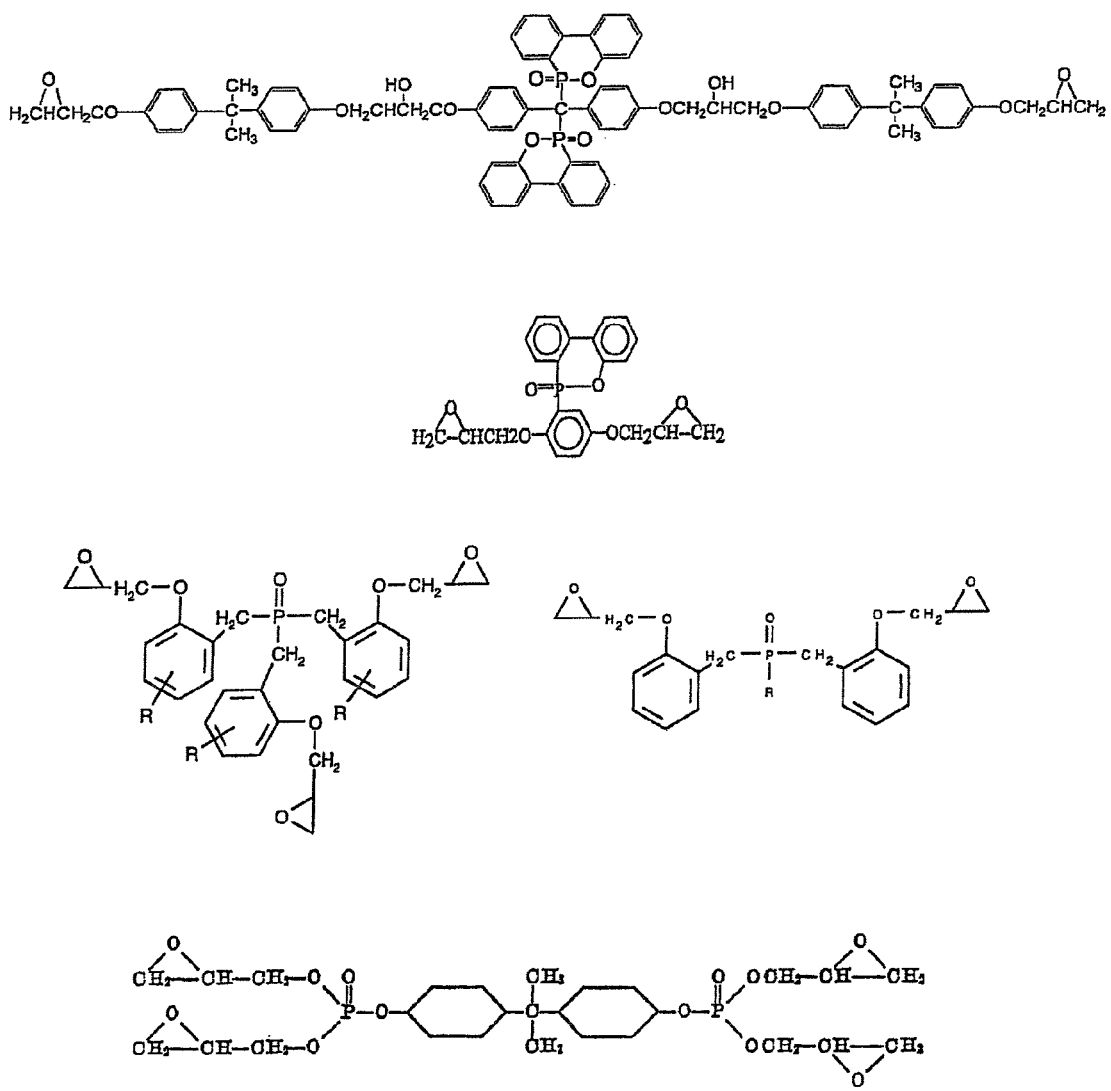
FIG. 10: example of chemical formula of compounds used as phosphorus containing flame retardants.

Examples of chemical formulas for such compounds are presented in FIG. 10.

5.2. Co-Reactants

In the application according to the invention, the product containing epichlorohydrin is usually subjected to a reaction with an inorganic or organic compound containing phosphorus. Such inorganic compounds are for instance a phosphoric acid (ortho, pyro and polyphosphoric acid), a phosphoric acid salt and a phosphorus oxychloride. Examples of organic compounds containing phosphorus are for instance phosphoric acid esters (of ortho, pyro and polyphosphoric acid), phosphonic acids, their esters or their salts, phosphinic acids, their esters or their salts and phosphine oxides.

The compounds containing phosphorus may be represented by the general formula

$$O=P(X^1)(X^2)(X^3) \qquad \text{(XVIII)}$$

or

$$P(X^1)(X^2)(X^3) \qquad \text{(XIX)}$$

wherein $X^1$, $X^2$, $X^3$ can independently be selected from a halogen, H, OH, $OR^{41}$, $R^{41}$, $OR^{42}(OH)_n$ and $R^{42}(OH)_n$ wherein the halogen is preferably selected from bromine and chlorine and is preferably chlorine wherein $R^{41}$ is an alkyl, an aryl, an alkylaryl, an arylalkyl, a cycloalkyl radical containing from 1 to 20 carbon atoms, often from 3 to 12 carbon atoms wherein $R^{42}$ is an alkylene, arylene, alkylarylene, arylalkylene, cycloalkylene radical containing from 1 to 20 carbon atoms, often from 3 to 12 carbon atoms wherein n is an integer equal to 1 or 2 wherein at least two of $X^1$, $X^2$, $X^3$ can be joined to form a ring, preferably with the phosphorus atom.

Examples of phosphorus containing compounds are tris(1,3-dichloro-2-propyl) phosphate, tris(1-chloro-2-propyl) phosphate, tris(2,3-dichloropropyl) phosphate, isobutylbis(hydroxypropyl)phosphine oxide, 10-(2',5'-dihydroxyphenyl)-9,10-dihydro-9-oxa-10-phosphaphenanthrene-10-oxide (DHQEP), 9,10-dihydro-9-oxa-10-phosphaphenanthrene-10-oxide (DOPO), the reaction products of DOPO and 4,4'-dihydroxybenzophenone (DOPO2OH and 2DOPO-PhOH,II as represented in Liu Y. L., Journal of Polymer Science: Part A: Polymer Chemistry, 2002, Vol. 40, 359-368 and Journal of Applied Polymer Science, 2002, Vol. 83, 1697-1701).

5.3. Processes

The reaction between the product containing epichlorohydrin and the phosphorus containing compound is carried out by any process known in the art such as those described in Journal of Applied Polymer Science, 2002, Vol. 83, 1697-1701).

The reaction is generally carried out in the liquid phase, possibly in the presence of a solvent. The solvent may be selected from water, an organic solvent e.g. an alcohol, or mixtures thereof. An alcohol is preferred. Monoalcohols, like methanol, ethanol, n-propanol, isopropanol and butanol are preferred organic solvents, with ethanol being particularly preferred.

The content of epichlorohydrin in the reaction mixture is usually higher than or equal to 0.1 mol/l, often higher than or equal to 1.0 mol/l, frequently higher than or equal to 2 mol/l and particularly higher than or equal to 5 mol/l. That epichlorohydrin content is usually lower than 20 mol/1.

The content of the phosphorus containing compound in the reaction mixture is usually higher than or equal to 0.1 mol/l, often higher than or equal to 0.2 mol/l and frequently higher than or equal to 0.5 mol/l. That content is usually lower than 2 mol/l.

The molar epichlorohydrin/phosphorus containing compound ratio is usually higher than or equal to 1, preferably higher than or equal to 2, more preferably higher than or equal to 5 and most preferably higher than or equal to 10. That ratio is usually lower than or equal to 50, more preferably lower than or equal to 30 and most preferably lower than or equal to 20.

The temperature at which the reaction is carried out is generally higher than or equal to 0° C., often higher than or equal to 5° C., frequently higher than or equal to 10° C., particularly higher than or equal to 20° C. and more specifically higher than or equal to 50° C. That temperature is usually lower than or equal to 100° C., preferably lower than or equal to 80° C., more preferably lower than or equal to 60° C., and most preferably lower than or equal to 30° C.

The pressure at which the reaction is carried out is generally higher than or equal to 0.1 bar absolute, preferably higher than or equal to 0.2 bar, more preferably higher than or equal to 0.5 bar and most preferably higher than or equal to 1 bar. That pressure is usually lower than or equal to 20 bar, preferably lower than or equal to 10 bar, more preferably lower than or equal to 5 bar, and most preferably lower than or equal to 2 bar.

The duration of the reaction depends on the temperature at which the reaction is carried out. That duration is generally higher than or equal to 10 min absolute, preferably higher than or equal to 1 h, more preferably higher than or equal to 10 min and most preferably higher than or equal to 24 h. That duration is usually lower than or equal to 72 h, preferably lower than or equal to 60 h, more preferably lower than or equal to 48 h, and most preferably lower than or equal to 30 h.

A basic compound, e.g., potassium hydroxide can be present in the reaction medium. This is generally the case when the phosphorus containing compound includes OH groups in the molecule. The molar basic compound/phosphorus containing compound ratio is usually higher than or equal to 0.1, preferably higher than or equal to 0.15, and most preferably higher than or equal to 0.2. That ratio is usually lower than or equal to 5, more preferably lower than or equal to 3 and lost preferably lower than or equal to 1.

An onium salt, preferably a quaternary ammonium or phosphonium salt, more preferably a quaternary ammonium chloride, like for instance benzyltrimethylammonium chloride, can be present in the reaction medium. This is generally the case when the phosphorus containing compound is a phosphine oxide. The onium/phosphorus containing compound ratio is usually higher than or equal to 0.01, preferably higher than or equal to 0.05, and most preferably higher than or equal to 0.1. That ratio is usually lower than or equal to 1, more preferably lower than or equal to 0.5 and most preferably lower than or equal to 0.2.

The product of the reaction can be recovered by any means, e.g., filtration and submitted to washing operations before being submitted to evaporation under reduced pressure.

5.4. Uses

Flame retardants are usually used to inhibit the evolution of combustible gases in various materials such as polymers, in particular in polyurethane foams.

6. Detergent Ingredients 6.1. General

The product containing epichlorohydrin according to the invention can be used for the manufacture of detergent ingredients. By detergent ingredient, one intends to denote a compound, the chemical formula of which contains at least one 3-sulfonate-2-hydroxy-propyloxy group. The compound can be an oligomer or a polymer. An oligomer is a polymer with a number of repeat units in each polymer molecule of less than 20.

By detergent ingredient, one intends to denote a polymer, at least one repeat unit of which comprises at least one 2-hydroxypropylammonium group, preferably a 2-hydroxypropylimidazolidium group.

The product containing epichlorohydrin according to the invention can preferably be used for the manufacture of cationic monomers, polymers or oligomers, anionic surfactants, for instance sulfonates based surfactants, preferably alkyl glyceryl ether sulfonate surfactants, monomeric or oligomeric or cationic cyclic amine based polymers.

6.2. Co-Reactants

In the application according to the invention, when the detergent auxiliary is a sulfonate based surfactant, the product containing epichlorohydrin is usually subjected to a reaction with an aliphatic alcohol containing from 10 to 40 carbon atoms, preferably from 10 to 22 carbon atoms more preferably from 14 to 18 carbon atoms and most preferably from 16 to 18 carbon atoms. The alkyl chain may be branched or linear or ethoxylated, wherein when present, the branches comprise an alkyl moiety containing from 1 to 4 carbon atoms, such as methyl or ethyl.

In the application according to the invention, when the detergent ingredient is a cationic amine based polymer, the product containing epichlorohydrin is usually subjected to a reaction with an amine selected from the group consisting of linear alkylamines, branched alkylamines, cycloalkylamines, alkoxyamines, amino alcohols, cyclic amines containing at least one nitrogen atom in a ring structure, alkylenediamines, polyetherdiamines, polyalkylenepolyaminesamine.

Specific examples of the said amines are given above.

Cyclic amines containing at least one nitrogen atom in a ring structure are for example monoaminoalkylpiperazines, bis(aminoalkyl)piperazines, monoaminoalkylimidazoles, aminoalkylmorpholines, aminoalkylpiperidines and aminoalkylpyrrolidines. The monoaminoalkylpiperazines are for example 1-(2-aminoethyl)piperazine and 1-(3-aminopropyl)piperazine. Preferred monoaminoalkylimidazoles have 2 to 8 carbon atoms in the alkyl group. Examples of suitable compounds are 1-(2-aminoethyl)imidazole and 1-(3-aminopropyl)imidazole. Suitable bis(aminoalkyl)piperazines are for example 1,4-bis(2-aminoethyl)piperazine and 1,4-bis(3-aminopropyl)-piperazine. Preferred aminoalkylmorpholines are aminoethylmorpholine and 4-(3-aminopropyl)-morpholine. Other preferred compounds of this group are aminoethylpiperidine, aminopropylpiperidine and aminopropylpyrrolidine.

Cyclic amines with at least two reactive nitrogen atoms in the ring are for example imidazole, C-alkyl substituted imidazoles having 1 to 25 carbon atoms in the alkyl group such as 2-methylimidazole, 2-ethylimidazole, 2-propylimidazole, 2-isopropylimidazole and 2-isobutylimidazole, imidazoline, C-alkyl substituted imidazolines having 1 to 25 carbon atoms in the alkyl group and arylimidazolines such as 2-phenylimidazoline and 2-tolylimidazoline, piperazine, N-alkylpiperazines having 1 to 25 carbon atoms in the alkyl group such as 1-ethylpiperazine, 1-(2-hydroxy-1-ethyl)piperazine, 1-(2-hydroxy-1-propyl)piperazine, 1-(2-hydroxy-1-butyl)piperazine, 1-(2-hydroxy-1-pentyl)piperazine, 1-(2,3-dihydroxy-1-propyl)piperazine, 1-(2-hydroxy-3-phenoxyethyl)piperazine, 1-(2-hydroxy-2-phenyl-1-ethyl)piperazine, N,N'-dialkylpiperazines having 1 to 25 carbon atoms in the alkyl group for example 1,4-dimethylpiperazine, 1,4-diethylpiperazine, 1,4-dipropylpiperazine, 1,4-dibenzylpiperazine, 1,4-bis(2-hydroxy-1-ethyl)piperazine, 1,4-bis(2-hydroxy-1-propyl)piperazine, 1,4-bis(2-hydroxy-1-butyl)piperazine, 1,4-bis(2-hydroxy-1-pentyl)piperazine, and 1,4-bis(2-hydroxy-2-phenyl-1-ethyl)piperazine. Other cyclic amines with at least two reactive nitrogen atoms are melamine and benzimidazoles such as 2-hydroxybenzimidazole and 2-aminobenzimidazole.

6.3. Processes

The reaction between the product containing epichlorohydrin and the alcohol is carried out by any process known in the art such as those described in U.S. Pat. No. 5,567,359 and US 2006/0079433, the contents of which are incorporated herein by reference.

The reaction is usually carried out at a temperature between 65 and 90° C.

Typical molar ratios of alcohol:epichlorohydrin range from 1:1.24 to 1:4.02.

A catalyst is usually used when carrying out the reaction, for instance stannic chloride. The mass ratio of initial alcohol:stannic chloride is generally of 100:0.67.

The duration of the reaction is usually between 0.25 and 1 h.

The epichlorohydrin/alcohol ratio and the duration can be adapted to the required degree of oligomerisation Epichlorhydrin is usually slowly added to the alcohol-catalyst mixture.

The product of the reaction is a monomeric or oligomeric alkyl chloroglyceryl ether.

The alkyl chloroglyceryl ether is further converted into an alkyl glycidyl ether by reaction with a basic compound, preferably sodium hydroxide. That reaction is usually carried out with a 35% aqueous solution of sodium hydroxide at a temperature higher than 90° C. and for a molar ratio alcohol:NaOH of 1:1.5.

The alkyl glycidyl ether is further converted into an alkyl glyceryl surfactant by reaction usually with a mixture of sodium bisulfite and sodium sulfite, generally obtained by combining sodium meta-bisulfite with sodium hydroxide.

The reaction between the product containing epichlorohydrin and the amine is carried out by any process known in the art such as those described in U.S. Pat. No. 6,740,633 and US 2006/0052272, the contents of which are incorporated herein by reference.

The reaction is usually carried out at a temperature between 25 and 90° C., in two steps the first one at a temperature between 40 and 60° C. and the second one between 90 and 100° C.

Typical molar ratios of amine:epichlorohydrin range from 1:1 to 1:1.4.

The duration of the reaction is usually between 0.25 and 1 h.

The condensation product between the amine and epichlorohydrin is usually further quaternarized using alkyl halides, epoxides, chloroacetic acid, 2-chloroethanesulfonic acid, chloropropionic acid, epoxysuccinic acid, propane sulfone, 3-chloro-2-hydroxypropanesulfonic acid, dimethyl sulfate and/or diethyl sulfate, or oxidized by oxidation of the tertiary nitrogen atoms of the condensation products to N-oxides.

6.4. Uses

Examples of detergent ingredients are surfactants or surface deposition enhancing materials. They are usually used as components of cleaning compositions for instance dishwashing, laundry compositions, shampoos and synbars.

7. Epichlorhydrin Elastomers 7.1. General

The product containing epichlorohydrin according to the invention can be used for the manufacture of epichlorohydrin elastomers.

By epichlorohydrin elastomer, one intends to denote a polymer, containing at least one type of repeat units, at least one type of repeat units containing at least one 2-chloromethylethoxy group. The polymer can a homopolymer or a copolymer.

Examples of epichlorohydrin elastomers are homopolymers of epichlorohydrin, copolymers of epichlorohydrin with an alkylene or phenylene oxide, and terpolymers of epichlorohydrin with an alkylene or phenylene oxide, and a glycidyl ether.

The alkylene oxide can be selected from styrene oxide, propylene oxide, ethylene oxide, butene-1 oxide, dodecene-1-oxide, and is preferably ethylene oxide.

The glycidyl ether can be selected from alkyl and haloalkyl glycidyl ethers, for instance, 2-chloroethyl glycidyl ether and allyl glycidyl ether.

7.2. Co-Reactants

In the application according to the invention, the product containing epichlorohydrin is usually subjected to a reaction with an alkylene or phenylene oxide or with an alkylene or phenylene oxide and a glycidyl ether or the epichlorohydrin is homopolymerized.

7.3. Processes

The reaction is carried out by any process known in the art such as those described in U.S. Pat. No. 3,135,705, U.S. Pat. No. 3,158,580, U.S. Pat. No. 3,158,581, U.S. Pat. No. 3,026,270 and U.S. Pat. No. 3,341,491, the contents of which are incorporated herein by reference.

The reaction is usually carried out in solution in aliphatic or aromatic hydrocarbons, chlorinated hydrocarbons, or ether.

The weight ratio between epichlorhydrin and the alkylene oxide is usually between 20:80 and 90:10.

The reaction is preferably carried out in the presence of a catalyst formed by reacting $R^{51}_3Al$ and water (thought to be $R^{51}_2Al—O—AlR^{51}_2$), where $R^{51}$ can be selected from alkyl, cycloalkylaryl or alkaryl radical. The catalyst activity can be improved by the addition of acetylacetone. Some combinations of organozinc and organomagnesium compounds, as well as other additives and chelating agents in combination with alkylaluminum compounds, are also effective catalysts.

The reaction can be carried out in a continuous process using a back-mixed reactor.

The temperature at which the reaction can be carried out is usually comprised between −80° C. and 250° C., preferably between −80 and 150° C., more preferably between −30 and 100° C. A temperature between 25 and 50° C. is particularly convenient The homopolymer of epichlorohydrin and the copolymers can be further cross-linked, e.g., by further reacting with a polyamine, or an amine in the presence of at least one agent from the group of sulfur, dithiocarbamates, thiuram sulfides and thiazoles, or with a metal compound selected from the group consisting of salts of aromatic carboxylic acids, aliphatic carboxylic acids, carbonic acid, phosphorous acid, silicic acid, and oxides of the metals of Groups IIA, IIB and IVA of the periodic Table and at least one heterocyclic compound selected from the group consisting of 2-mercaptoimidazolines and 2-mercaptopyrimidine.

7.4. Uses

The epichlorohydrin elastomers are generally used in specialty applications, like for instance automotive components (fuel pump diaphragms, emission control hoses, motor mounts, gaskets, seals and portable fuel tanks), in the aircraft industry, for specialty roofing membranes, coated fabrics, solvent storage containers, paper mill and printing roll and in a variety of oil specialties. −80° C. and 250° C., preferably between −80 and 150° C., more preferably between −30 and 100° C. A temperature between 25 and 50° C. is particularly convenient The homopolymer of epichlorohydrin and the copolymers can be further cross-linked, e.g., by further reacting with a polyamine, or an amine in the presence of at least one agent from the group of sulfur, dithiocarbamates, thiuram sulfides.

A further goal of the invention is to provide epichlorohydrin which can be used in various applications, obtained from a starting material different from propylene. The invention therefore further relates to the use of epichlorohydrin obtained from glycerol in the manufacture of glycidyl amides or glycidyl imides or coagulants or wet-strength resins or cationization agents or flame retardants, or detergent ingredients.

EXAMPLES

Five epichlorohydrin (ECH) samples have been used. Their compositions obtained by gas chromatography analysis are presented in Table 1.

The polymerization of epichlorohydrin (ECH) has been carried out in the presence of the system tetraoctylammonium bromide($Noct_4Br$)/triisobutyl aluminum (TiBA).

The epichlorohydrin has been dried over calcium hydride under vacuum for 24 h at 25° C. and further distilled.

The polymerization reactions have been carried out in pyrex vessels fitted with polytetrafluorethylene valves. The vessels have been evacuated under flame heating to remove residual moisture. After cooling to room temperature, the vessels have been cooled to −30° C. (ethanol/liquid nitrogen

TABLE 1

| Component (g/kg) | ECH 1 | ECH 2 | ECH 3 | ECH 4 | ECH5 |
|---|---|---|---|---|---|
| acetaldehyde | 0.004 | n.d | n.d | n.d. | n.d. |
| acrolein | <0.001 | 0.003 | 0.003 | n.d. | n.d. |
| 2-propanol | <0.001 | n.d. | n.d. | n.d. | n.d. |
| 3-chloro-1-propene | n.d. | n.d. | n.d. | n.d. | n.d. |
| allyl alcohol | 0.001 | <0.001 | <0.001 | n.d. | 0.003 |
| hydroxyacetone | 0.094 | 0.018 | 0.018 | 0.006 | 0.006 |
| chloroacetone + (3,3-dichloro-1-propene) | 0.033 | 0.038 | 0.040 | n.d. | 0.024 |
| 1,2-dichloropropane | 0.042 | n.d. | n.d. | 0.001 | n.d. |
| 2,3-dichloro-1-propene | 0.005 | n.d. | n.d. | 0.004 | n.d. |
| 1-chloro-2,3-epoxypropane (*) | >998.464 | >999.474 | >999.045 | >999.503 | >999.865 |
| 1,3-dichloro-1-propene cis maj. + ($C_6H_{14}O$ min.) | 0.219 | 0.008 | 0.008 | 0.032 | 0.004 |
| 2-chloro-2-propene-1-ol | 0.348 | 0.016 | 0.016 | 0.14 | 0.012 |
| 1,3-dichloro-1-propene trans | 0.035 | 0.010 | 0.010 | 0.008 | 0.009 |
| $C_5H_{10}O/C_4H_7ClO$ | n.d. | n.d. | n.d. | 0.014 | 0.001 |
| $C_6H_{12}O$ | n.d. | n.d. | n.d. | 0.011 | <0.001 |
| 1,3-dichloropropane | 0.002 | 0.34 | 0.34 | 0.005 | 0.030 |
| Cyclopentanone | 0.001 | 0.004 | 0.004 | n.d. | 0.004 |
| dibromochloromethane | 0.004 | n.d. | n.d. | 0.084 | n.d. |
| $C_6H_{10}O$ iso 1 | 0.003 | n.d. | n.d. | 0.009 | <0.001 |
| $C_6H_{10}O$ iso 2 | 0.012 | n.d. | n.d. | 0.009 | 0.001 |
| 1,2-epoxyhexane + (1,2,2-trichloropropane) | 0.030 | 0.002 | 0.002 | n.d. | 0.001 |
| $C_6H_{10}O$ iso 3 | 0.004 | n.d. | n.d. | 0.031 | 0.001 |
| dichloroepoxypropane | 0.003 | n.d. | n.d. | 0.006 | n.d. |
| 1,3,3-trichloro-1-propene cis + 1,1,3-trichloropropene | 0.012 | n.d. | n.d. | 0.004 | n.d. |
| 1,1,2-trichloropropane | 0.211 | 0.001 | 0.001 | 0.025 | 0.007 |
| chlorobenzene | 0.011 | <0.001 | <0.001 | 0.001 | 0.007 |
| 1,3,3-trichloro-1-propene trans | 0.015 | n.d. | n.d. | 0.012 | 0.001 |
| 1,2,3-trichloropropene trans | 0.016 | <0.001 | <0.001 | 0.003 | 0.001 |
| 1,3-dichloro-2-propanol | 0.111 | 0.023 | 0.024 | 0.017 | 0.008 |
| 1,2,3-trichloropropane | 0.014 | n.d. | n.d. | 0.024 | n.d. |
| 1,2,3-trichloropropene cis | 0.002 | n.d. | n.d. | n.d. | n.d. |
| 3-chloro-1,2-propanediol + 2,3-dichloro-1-propanol | 0.13 | <0.001 | 0.001 | n.d. | 0.001 |
| $C_6H_{13}Br$ | n.d. | n.d. | n.d. | 0.005 | n.d. |
| $C_6H_{10}Cl_2$ iso 1 | n.d. | n.d. | n.d. | 0.005 | n.d. |
| $C_6H_{10}Cl_2$ iso 2 | n.d. | n.d. | n.d. | 0.004 | n.d. |
| methyl glycidyl ether | 0.007 | 0.054 | 0.48 | n.m. | n.m. |
| Unknowns (sum) | 0.170 | 0.007 | 0.008 | 0.087 | 0.024 | n.d.: not detected,
n.m.: not measured
(*) 1-chloro-2,3-epoxypropane amount calculated on the basis of the total content of other organic components Examples 1 to 10

Homopolymerization of ECH

The tests have been carried out according to the following procedure with epichlorohydrin sample ECH1 (examples 1 to 3), ECH 2 (examples 4 to 6) and ECH 3 (examples 7 to 10). The quantities of chemicals are indicated in Table 2.

cooling bath) and toluene and epichlorohydrin, have been added under vacuum. After those additions, argon has been introduced in the vessel and tetraoctylammonium bromide and triisobutyl aluminum have been added to the vessel. This addition constituted the time zero of the reaction. After a given time under magnetic stirring at −30° C., the reaction has been stopped by adding 1-2 ml of ethanol to the vessel. Half of the volume of the reaction medium has then been submitted to evaporation after which the polymer has been recovered from the vessel.

The conversion has been obtained by comparing the weight of recovered polymer with the weight of added epichlorohydrin.

The theoretical molar weight (Mn th.) has been calculated on the basis of the quantity of tetraoctylammonium bromide.

The measured polymer molar weight (Mn exp) and the molar weight dispersion have been obtained by Gel Permeation Chromatography.

The tacticity of the polymer has been obtained by $^{13}$C and $^{1}$H NMR.

The results of the tests are summarized in Table 3.

TABLE 2

| Example n° | ECH (ml) | Toluene (ml) | Noct$_4$Br (ml) | TiBA (ml) |
|---|---|---|---|---|
| 1 | 4 | 10.2 | 2.15 | 0.71 |
| 2 | 4 | 10.2 | 2.15 | 0.71 |
| 3 | 3.4 | 9.9 | 0.91 | 0.30 |
| 4 | 4 | 10.2 | 2.15 | 0.71 |
| 5 | 4 | 10.2 | 2.15 | 0.71 |
| 6 | 4 | 11.6 | 1.08 | 0.35 |
| 7 | 4 | 10.2 | 2.15 | 0.71 |
| 8 | 4 | 10.2 | 2.15 | 0.71 |
| 9 | 3.6 | 11.4 | 0.97 | 0.43 |
| 10 | 4 | 11.6 | 1.08 | 0.35 |

TABLE 3

| Example | Reaction time (h) | Conversion (mol %) | Mn th. (g/mol) | Mn exp. (g/mol) | Dispersion | Tacticity |
|---|---|---|---|---|---|---|
| 1 | 1 | 100 | 10000 | 10700 | 1.17 | atactic |
| 2 | 1 | 100 | 10000 | 10100 | 1.23 | n.m. |
| 3 | 2 | 100 | 20000 | 20200 | 1.17 | n.m. |
| 4 | 1 | 100 | 10000 | 16400 | 1.22 | n.m. |
| 5 | 1 | 100 | 10000 | 11200 | 1.20 | atactic |
| 6 | 1 | 100 | 20000 | 77700 (20%) | 1.40 | n.m. |
|   |   |   |   | 22200 (80%) | 1.20 |   |
| 7 | 1 | 80 | 8000 | 6800 | 1.17 | n.m. |
| 8 | 2 | 95 | 9500 | 12100 | 1.17 | atactic |
| 9 | 2 | 90 | 18000 | 24700 | 1.18 | n.m. |
| 10 | 6 | 94 | 18800 | 17650 | 1.17 | n.m. | n.m.: not measured

Examples 13 to 15

Homopolymerization of ECH

The tests have been carried out according to the following procedure with epichlorohydrin sample ECH1 (example 13), ECH 2 (example 14) and ECH 3 (example 15). The quantities of chemicals are indicated in Table 4.

The polymerization of epichlorohydrin (ECH) has been carried out in the presence of the system water/triethyl aluminum (TEA).

The procedure of example 1 has been followed except that TEA in solution in toluene and water have been added under argon to the vessel first evacuated and dried, left under magnetic stirring under vacuum for 30 min, before ECH in toluene has been added (time zero of the reaction). The polymerization has been carried out at a temperature of 25° C. for 12 h. The results have been summarized in Table 5

TABLE 4

| Example n° | ECH (ml) | Toluene (ml) | H$_2$O (µl) | TEA (ml) |
|---|---|---|---|---|
| 13 | 4 | 10 | 23 | 0.67 |
| 14 | 4 | 10 | 23 | 0.67 |
| 15 | 4 | 10 | 23 | 0.67 |

TABLE 5

| Example | Reaction time (h) | Conversion (mol %) | Mn exp. (g/mol) | Dispersion | Tacticity |
|---|---|---|---|---|---|
| 13 | 12 | 47 | 216000 | 2.02 | n.m. |
|   |   |   | 7000 | 1.04 |   |
| 14 | 12 | 50 | 285200 | 3.51 | atactic |
|   |   |   | 5850 | 1.08 |   |
| 15 | 12 | 55 | 357600 | 3.45 | atactic |
|   |   |   | 8100 | 1.31 |   | n.m.: not measured

Example 16

Preparation of a Product Consisting Predominantly in Diglycidyl Diether of Bisphenol A according to U.S. Pat. No. 2,811,227

The apparatus employed was a thermostatised flask equipped with a mechanical stirrer, with a jacket containing a thermocouple and with a Dean-Stark separator surmounted by a water-cooled condenser. A pump was used to inject a caustic soda aqueous solution at a constant rate in the flask.

The reaction flask was initially charged with a mixture of bisphenol A (68.4 g, 0.3 mol) and the epichlorohydrin sample ECH4 coming from a propylene-chlorine plant (277.5 g, 3.0 mol). The analysis of the epichlorhydrin is given in Table 1. The trichloropropane content is of 0.049 g/kg. The mixture was heated at reflux under stirring to a temperature of 111° C. A 40% aqueous solution of caustic soda (60.8 g, 0.6 mol) was introduced at a rate of 12 ml/h during 3.5 hour. The temperature of the mixture in the flask was maintained in the range 100° C.-115° C. in order to assure a constant reflux. The epichlorohydrin rich organic phase decanted during the reaction as a lower phase in the separator was recycled regularly in the reaction flask and the aqueous rich phase collected as an upper phase in the separator was regularly drawn off. The heating was maintained for 15 min after the total introduction of the caustic soda solution to achieve the collect of the water phase in the decantor. 29.7 g of aqueous phase was collected with a composition given in Table 6.

The epichlorohydrin in excess was removed from the reaction mixture by distillation under a vacuum of 30 mbar and by a progressive heating of the mixture to 109° C. 156.1 g (1.7 mol) of epichlorohydrin was recovered in this step. The composition of the distillate is given in Table 6.

The salt was separated from the crude product (45.5 g) after addition of 567.2 g of toluene under agitation and by filtration. The cake of filtration was washed with 124.4 g of toluene. The toluene solutions were mixed and evaporated at 185° C. under a pressure of 1 mbar.

659.4 g of toluene was recovered as the condensate of the evaporated fraction with a composition given in Table 6. The residual product of the evaporation (100.5 g) contained the diglycidyl ether of bis-phenol A as a major product and no trace of unconverted bis-phenol A (<5 mg/kg). The residue contained 4.98 mol epoxy per kg and 1.52% of hydrolysable chlorine.

Example 17

The trial was realized in the apparatus described in example 16.

The reaction flask was initially charged with a mixture of bisphenol A (68.4 g, 0.3 mol) and epichlorohydrin sample ECH 5 (277.5 g, 3.0 mol). The analysis of the epichlorhydrin is given in Table 1. The trichloropropane content is of 0.007 g/kg. The mixture was heated at reflux under stirring to a temperature of 119° C. A 40% aqueous solution of caustic soda (60.8 g, 0.6 mol) was introduced at a rate of 12 ml/h during 3.5 hour. The temperature of the mixture in the flask was maintained in the range 102° C. –119° C. in order to assure a constant reflux. The epichlorohydrin rich organic phase decanted during the reaction as a lower phase in the separator was recycled regularly in the reaction flask and the aqueous rich phase collected as an upper phase in the separator was regularly drawn off. The heating was maintained for 15 min after the total introduction of the caustic soda solution to achieve the collect of the water phase in the decantor. 54.5 g of aqueous phase was collected with a composition given in Table 6.

The epichlorohydrin in excess was removed from the reaction mixture by distillation under a vacuum of 30 mbar and by a progressive heating of the mixture to 118° C. 148.2 g (1.5 mol) of epichlorohydrin was recovered in this step. The composition of the distillate is given in Table 6.

The salt was separated from the crude product (47.8 g) after addition of 228.4 g of toluene under agitation and by filtration. The cake of filtration was washed with 97.3 g of toluene. The toluene solutions were mixed and evaporated at 180° C. under a pressure of 1 mbar.

305.0 g of toluene was recovered as the condensate of the evaporation with a composition given in Table 6. The residual product of the evaporation (99.8 g) contained the diglycidyl ether of bis-phenol A as a major product and no trace of unconverted bis-phenol A (<5 mg/kg). The residue contained 4.93 mol epoxy per kg and 0.49% of hydrolysable chlorine.

The High Performance Liquid Chromatography analyses of the residual products obtained in examples 16 and 17 are similar.

TABLE 6

| | Example 16 | | | Example 17 | | |
| --- | --- | --- | --- | --- | --- | --- |
| Component | Epichlorohydrin evaporated (g/kg) | Water evaporated (mg/l) | Toluene evaporated (g/kg) | Epichlorohydrin evaporated (g/kg) | Water evaporated (mg/l) | Toluene evaporated (g/kg) |
| acetaldehyde | n.d. | 2.9 | n.d. | n.d. | 1.3 | n.d. |
| acrolein | n.d. | 0.58 | n.d. | 0.002 | 0.42 | n.d. |
| 2-propanol | n.d. | <0.05 | n.d. | n.d. | 0.3 | n.d. |
| 3-chloro-1-propene | 0.001 | n.d. | n.d. | n.d. | n.d. | n.d. |
| allyl alcohol | n.d. | n.d. | n.d. | 0.001 | 0.2 | n.d. |
| hydroxyacetone | 0.016 | n.d. | n.d. | 0.002 | n.d. | n.d. |
| chloroacetone + (3,3-dichloro-1-propene) | 0.003 | 0.65 | n.d. | 0.002 | 0.53 | n.d. |
| 1,2-dichloropropane | | | n.d. | n.d. | n.d. | n.d. |
| 2,3-dichloro-1-propene | 0.005 | 0.07 | n.d. | n.d. | n.d. | n.d. |
| 1-chloro-2,3-epoxypropane | principal product | (45 g/kg) | 1.6 | principal product | (46 g/kg) | 3.3 |
| 1,3-dichloro-1-propene cis maj. + (C6H14O min.) | 0.026 | 0.36 | n.d. | 0.003 | n.d. | n.d. |
| 2-chloro-2-propene-1-ol | 0.19 | 0.12 | n.d. | 0.016 | <0.05 | n.d. |
| 1,3-dichloro-1-propene trans | 0.007 | <0.05 | n.d. | 0.008 | n.d. | n.d. |
| $C_5H_{10}O/C_4H_7ClO$ | 0.019 | 0.05 | n.d. | 0.001 | n.d. | n.d. |
| $C_6H_{12}O$ | 0.022 | 0.28 | n.d. | 0.021 | n.d. | n.d. |
| 1,3-dichloropropane | 0.001 | n.d. | n.d. | 0.03 | <0.05 | n.d. |
| Cyclopentanone | n.d. | n.d. | n.d. | 0.006 | n.d. | n.d. |
| dibromochloromethane | 0.080 | n.d. | n.d. | n.d. | n.d. | n.d. |
| $C_6H_{10}O$ iso 1 | 0.033 | 0.11 | n.d. | 0.038 | n.d. | n.d. |
| $C_6H_{10}O$ iso 2 | 0.040 | 0.31 | n.d. | 0.001 | n.d. | n.d. |
| 1,2-epoxyhexane + (1,2,2-trichloropropane) | n.d. | n.d. | n.d. | 0.001 | n.d. | n.d. |
| $C_6H_{10}O$ iso 3 | 0.036 | 0.21 | n.d. | 0.002 | n.d. | n.d. |
| dichloroepoxypropane | 0.006 | n.d. | n.d. | n.d. | n.d. | n.d. |
| 1,3,3-trichloro-1-propene cis + 1,1,3-trichloropropene | 0.006 | n.d. | n.d. | n.d. | n.d. | n.d. |
| 1,1,2-trichloropropane | 0.005 | n.d. | n.d. | | n.d. | n.d. |
| chlorobenzene | 0.001 | n.d. | n.d. | 0.008 | n.d. | n.d. |
| 1,3,3-trichloro-1-propene trans | 0.009 | n.d. | n.d. | n.d. | n.d. | n.d. |
| 1,2,3-trichloropropene trans | 0.003 | n.d. | n.d. | 0.001 | n.d. | n.d. |
| 1,3-dichloro-2-propanol | 3.4 | 143 | 0.38 | 2.5 | 111 | 0.074 |
| 1,2,3-trichloropropane | 0.022 | n.d. | 0.002 | n.d. | n.d. | n.d. |
| 1,2,3-trichloropropene cis | n.d. | n.d. | n.d. | n.d. | n.d. | n.d. |
| 3-chloro-1,2-propanediol + 2,3-dichloro-1-propanol | 0.13 | 5.9 | 0.064 | 0.071 | 4.1 | 0.033 |
| $C_6H_{13}Br$ | n.d. | <0.05 | 0.005 | n.d. | <0.05 | |
| $C_6H_{10}Cl_2$ iso 1 | 0.009 | n.d. | n.d. | n.d. | n.d. | n.d. |

TABLE 6-continued

| | Example 16 | | | Example 17 | | |
|---|---|---|---|---|---|---|
| Component | Epichlorohydrin evaporated (g/kg) | Water evaporated (mg/l) | Toluene evaporated (g/kg) | Epichlorohydrin evaporated (g/kg) | Water evaporated (mg/l) | Toluene evaporated (g/kg) |
| $C_6H_{10}Cl_2$ iso 2 | 0.007 | n.d. | n.d. | n.d. | n.d. | n.d. |
| methyl glycidyl ether | n.m. | n.m. | n.m. | n.m. | n.m. | n.m. |
| Unknowns (sum) | 0.299 | 10.00 | 1.31 | 0.213 | 1.3 | 1.373 | n.d.: not detected,
n.m.: not measured

Example 18

A glass thermostated jacketed reactor having a working volume of 305 ml was supplied continuously with 47.2 wt % sodium hydroxide and with an aqueous mixture of dichloropropanol, a mixture prepared from glycerol and concentrated hydrochloric acid in the presence of an organic acid according to the International Application WO 2005/054167 filed by Solvay SA. The mixture contained 575 g of water/kg, 404.6 g of 1,3-dichloro-2-propanol/kg, 20.1 g of 2,3-dichloro-1-propanol/kg, 0.14 g of acrolein/kg, 0.13 g of epichlorohydrin/kg, 0.04 g of 1,2,3-trichloropropane/kg, 0.04 g of chloroacetone/kg and 0.03 g of an ether of crude formula $C_6H_{10}O_2Cl_2$/kg. The sodium hydroxide was introduced at a flow rate of 262 g/h and the aqueous dichloropropanol mixture was introduced at a flow rate of 1180 g/h. The reaction medium was constantly maintained at 25° C. with vigorous stirring. The liquid mixture exiting the reactor by continuous overflow was collected and then separated in batch mode in a glass funnel so as to obtain a first separated fraction and a second separated fraction. 3753 g of first separated fraction (MEL1) were subjected to a batch distillation under a vacuum of 193 mbar. The batch distillation was carried out using a round-bottomed flask equipped with a magnetic stirrer bar, a thermocouple to measure the temperature of the liquid and a plate distillation column surmounted by a device enabling part of the distillate to be refluxed at the top of the column. The glass plate column comprised 5 plates having a diameter of 30 mm, pierced by an internal aperture 10 mm diameter central hole for the flow of liquid and three rows of small holes having a diameter of around 0.8 mm, spaced at regular intervals of less than 1 mm between each hole, placed in an arc over three quarters of the circumference. The spacing between the plates was 30 mm. The column was adiabatic (glass jacket under vacuum). A thermocouple placed in the top of the distillation column enabled the temperature of the gas phase distilled to be measured. The distillate was collected in a funnel with a stopcock. A first distillation fraction was collected between 49° C. and 67° C. and gave, after separation, 425 g of an organic phase (D1 org) and 159 g of an aqueous phase (D1 aq). The organic phase (D1 org) was combined with the contents of the boiler to give the mixture (MEL2) which was then distilled at a temperature of 187° C. A second distillation fraction was collected between 66° C. and 67° C. and resulted, after separation, in 244 g of an organic phase (D2 org) and 11.5 g of an aqueous phase (D2 aq). A main distillate of 2082 g of epichlorohydrin at 999.5 g/kg was then collected (D3) at a temperature of 67° C. The mixture constituting the final boiler (MEL3) weighed 1226 g and only contained a very low fraction of epichlorohydrin implemented. The organic phase D2 org and the boiler MEL3 could be recycled to the distillation operations in order to recover, for enhanced value, epichlorohydrin and a mixture of 1,3-dichloro-2-propanol and 2,3-dichloro-1-propanol respectively. The compositions (g/kg) used and obtained in the distillation operations are described in Table 7.

TABLE 7

| | MEL1 | D1 org | D1 aq | MEL2 | D2 org | D2 aq | D3 | MEL3 |
|---|---|---|---|---|---|---|---|---|
| Acrolein | 0.2 | 0.61 | 0.13 | 0.076 | 0.99 | 0.12 | 0.050 | 0.006 |
| Acetone | 0.006 | 0.024 | 0.02 | <0.005 | 0.027 | 0.01 | <0.01 | <0.005 |
| Isopropanol | 0.032 | 0.124 | n.d. | 0.014 | 0.15 | n.d. | <0.005 | n.d. |
| 2-Chloropropane | 0.047 | 0.021 | n.d. | <0.005 | 0.012 | n.d. | n.d. | n.d. |
| Allyl alcohol | | 0.003 | n.d. | n.d. | 0.003 | n.d. | n.d. | n.d. |
| 2,3-Epoxybutane | <0.005 | 0.008 | n.d. | n.d. | 0.010 | n.d. | n.d. | n.d. |
| $C_4H_8O$ | <0.005 | 0.010 | n.d. | n.d. | 0.012 | n.d. | n.d. | n.d. |
| 2-Butanone | <0.005 | 0.003 | n.d. | n.d. | 0.005 | n.d. | n.d. | n.d. |
| Hydroxyacetone | n.d. | | n.d. | n.d. | 0.001 | n.d. | n.d. | n.d. |
| Chloroethanol | n.d. | 0.005 | n.d. | n.d. | 0.001 | n.d. | n.d. | n.d. |
| Chloroacetone | 0.039 | 0.025 | n.d. | 0.039 | 0.034 | 0.03 | 0.05 | 0.019 |
| Epichlorohydrin | 653 | 982 | 46 | 666 | 989 | 36 | 999.5 | 29 |
| Glycidol | 0.06 | 0.000 | n.d. | 0.07 | n.d. | n.d. | n.d. | 0.24 |
| 2-chloro-2-propen-1-ol | <0.005 | 0.005 | 0.16 | <0.005 | 0.008 | 0.04 | <0.01 | 0.005 |
| cis-1,3-Dichloropropene | n.d. | 0.003 | 0.03 | <0.005 | 0.003 | 0.02 | <0.01 | <0.005 |
| trans-1,3-Dichloropropene | n.d. | 0.005 | n.d. | <0.005 | 0.009 | n.d. | <0.01 | <0.005 |
| 1,1,1-Trichloropropane | <0.005 | n.d. | n.d. | <0.005 | n.d. | n.d. | n.d. | 0.002 |
| Cyclopentanone | 0.021 | n.d. | n.d. | 0.023 | n.d. | n.d. | <0.01 | 0.021 |
| 3-Chloro-1-propanol | 0.013 | 0.000 | n.d. | 0.020 | n.d. | n.d. | n.d. | 0.016 |
| cis-1,3,3-Trichloropropene | n.d. | n.d. | n.d. | n.d. | n.d. | n.d. | n.d. | <0.005 |
| $C_4H_7ClO_2$ | n.d. | 0.000 | n.d. | n.d. | n.d. | n.d. | n.d. | <0.005 |
| Ethylbenzene | <0.005 | 0.000 | n.d. | n.d. | n.d. | n.d. | n.d. | <0.005 |
| 1,3-Dichloropropan-2-ol | 251 | 0.364 | 0.27 | 271 | 0.013 | 0.82 | 0.010 | 789 |
| 2-Methyl-2-cyclopenten-1-one | n.d. | n.d. | n.d. | <0.005 | n.d. | n.d. | n.d. | <0.005 |

TABLE 7-continued

| | MEL1 | D1 org | D1 aq | MEL2 | D2 org | D2 aq | D3 | MEL3 |
|---|---|---|---|---|---|---|---|---|
| 1,2,3-Trichloropropane | 0.16 | n.d. | n.d. | 0.018 | n.d. | n.d. | n.d. | 0.015 |
| 2,3-Dichloro-1-propanol + 3-chloro-1,2-propanediol | 56 | 1.94 | 36.42 | 61 | 0.046 | 21 | n.d. | 174 |
| Phenol | 0.011 | n.d. | n.d. | 0.012 | n.d. | n.d. | n.d. | 0.035 |
| $C_6H_8O_2$ | <0.005 | n.d. | n.d. | <0.005 | n.d. | n.d. | <0.01 | 0.008 |
| $C_6H_{12}OCl_2$ | 0.056 | n.d. | n.d. | 0.060 | n.d. | n.d. | n.d. | 0.051 |
| 3,5-Dimethyl-2-cyclohexen-1-one | 0.011 | n.d. | n.d. | 0.012 | n.d. | n.d. | n.d. | 0.035 |
| $C_6H_9Cl_3O_2$ | 0.031 | n.d. | n.d. | 0.034 | n.d. | n.d. | n.d. | 0.102 |
| 1-Phenoxy-2-propanone | 0.88 | n.d. | n.d. | 0.078 | n.d. | n.d. | n.d. | 1.754 |
| $C_6H_{10}Cl_2O_2$ | 0.076 | 0.002 | n.d. | 0.101 | n.d. | n.d. | n.d. | 0.325 |
| $C_9H_9Cl_3$ | <0.005 | n.d. | n.d. | <0.005 | n.d. | n.d. | n.d. | 0.012 |
| $C_6H_{11}O_2Cl_3$ | 0.74 | n.d. | n.d. | 0.81 | n.d. | n.d. | n.d. | 2.95 |
| $C_9H_{15}O_2Cl_2 + C_9H_{17}O_4Cl_3$ | <0.005 | n.d. | n.d. | <0.005 | n.d. | n.d. | n.d. | 0.56 |
| Sum of unknowns | 0.27 | 0.07 | 0.16 | 0.31 | 0.08 | n.d. | n.d. | 1.07 |
| Methyl glycidyl ether | 0.02 | n.d. | n.d. | 0.03 | 0.03 | n.d. | 0.04 | |
| $H_2O$ | 37 | 14.0 | n.d. | 2.32 | 9.9 | n.d. | 0.32 | 0.33 | n.d. = not detected

The invention claimed is:

1. A product comprising greater than 900 g of epichlorohydrin per kg of product and trichloropropane, wherein the amount of trichloropropane is from at least 0.001 mg-less than 0.01 g of trichloropropane per kg of product.

2. The product according to claim 1, further comprising at least one of the following compounds:
   (A) halogenated hydrocarbon compounds different from trichloropropane selected from the group consisting of chloropropene, trichloropropene, chloropropanol, chloropropenol, dichloropropene, dichloropropane, dichloropropanol, monochloropropanediol, chloroethers, monochlorobenzene, and any mixture of at least two of them, and/or
   (B) compounds selected from the group consisting of acrolein, methyl glycidyl ether, chloroacetone, glycerol, hydroxyacetone, glycidol, cyclopentanone, and any mixture of at least two of them.

3. The product according to claim 1, wherein the trichloropropane is selected from the group consisting of 1,2,3-trichloropropane, 1,1,1-trichloropropane, 1,1,3-trichloropropane, 1,1,2-trichloropropane, and any mixtures of at least two of them.

4. The product according to claim 1, comprising more than 990 g of epichlorohydrin per kg of product.

5. A process for manufacturing the product according to claim 1, comprising:
   a) in a liquid reaction medium, a mixture of dichloropropanol containing 1,3-dichloro-2-propanol and 2,3-dichloro-1-propanol, in which the 1,3-dichloro-2-propanol content, relative to the sum of the 1,3-dichloro-2-propanol and 2,3-dichloro-1-propanol contents, is at least 10 wt %, is reacted with at least one basic compound in order to form epichlorohydrin and at least one salt;
   b) at least one part of the liquid reaction medium from a) is subjected to a settling operation in which a first fraction containing most of the epichlorohydrin which was contained in the part of the reaction medium from step a) before the settling operation is separated from a second fraction containing most of the salt which was contained in the part of the reaction medium from a) before the settling operation; and
   c) the first fraction separated in b) is subjected to at least one supplementary treatment chosen from dilution, concentration, evaporation, distillation, stripping, liquid/liquid extraction and adsorption operations, alone or in combination.

6. The process according to claim 5, wherein the reaction from a) is carried out in at least two reaction zones, in which the volumes are assembled in a single jacket, and in which each of the reaction zones is supplied with the dichloropropanol mixture and/or with the basic compound.

7. The process according to claim 5, wherein, in c), the first fraction separated in b) is subjected to at least one of the treatments selected from the group consisting of:
   a treatment comprising at least one liquid/liquid extraction operation with an aqueous composition, and in which a first part containing most of the epichlorohydrin which was contained in the first fraction separated in b) before the extraction operation, is separated from a second part containing most of the water;
   a treatment comprising at least two distillation operations, of which at least one is an operation for drying by azeotropic distillation, and, at the end of the treatment, at least a first portion containing most of the epichlorohydrin which was contained in the first fraction before the distillation operations is obtained; and
   a treatment which comprises at least one adsorption operation and at least one distillation operation, and, at the end of the treatment, at least a first cut containing most of the epichlorohydrin which was contained in the first fraction before the treatment is obtained.

8. The process according to claim 5, wherein the first fraction separated in b) contains dichloropropanol and said fraction is subjected to at least one of the treatments selected from the group consisting of:
   a treatment comprising at least one liquid/liquid extraction operation with an aqueous composition, and in which a first part containing most of the epichlorohydrin which was contained in the first fraction separated in b) before the extraction operation, is separated from a second part containing most of the water;
   a treatment comprising at least two distillation operations, preferably at least two distillation operations of which at least one is an operation for drying by azeotropic distillation, and, at the end of the treatment, at least a first portion containing most of the epichlorohydrin which was contained in the first fraction before the distillation operations, and at least a second portion containing most of the dichloropropanol which was contained in the first fraction before the distillation operations, are obtained; and a treatment which comprises at least one adsorption operation and at least one distillation operation, and, at the end of the treatment, at least a first cut containing most of the epichlorohydrin which was contained in the first fraction before the treatment, and at least a second cut containing most of the dichloropropanol which was contained in the first fraction before the treatment, are obtained.

9. The product according to claim 1, wherein the amount of trichloropropane is less than or equal to 0.008 g per kg of product.

10. The product according to claim 1, wherein the amount of trichloropropane is less than or equal to 0.004 g per kg of product.

11. The product according to claim 1, comprising at least 999 g of epichlorohydrin per kg of product.

12. The product according to claim 10, comprising at least 999 g of epichlorohydrin per kg of product.

* * * * *